US006602700B1

(12) United States Patent
Li et al.

(10) Patent No.: US 6,602,700 B1
(45) Date of Patent: Aug. 5, 2003

(54) PHENOLIC ACID ESTERASES, CODING SEQUENCES AND METHODS

(75) Inventors: Xin-Liang Li, Athens, GA (US); Lars G. Ljungdahl, Athens, GA (US); Michael J. Azain, Watkinsville, GA (US); Edward T. Davies, Athens, GA (US); Ashit K. Shah, Athens, GA (US); David L. Blum, San Diego, CA (US); Irina Kataeva, Athens, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 0 days.

(21) Appl. No.: 09/603,311

(22) Filed: Jun. 21, 2000

Related U.S. Application Data

(63) Continuation-in-part of application No. 09/390,234, filed on Sep. 3, 1999, now Pat. No. 6,365,390.
(60) Provisional application No. 60/099,136, filed on Sep. 4, 1998.

(51) Int. Cl.[7] ............................ C12N 9/16; C12N 15/79; C12Q 1/44; C07R 17/00; C07H 21/04

(52) U.S. Cl. ................. 435/267; 435/19; 435/320.1; 435/196; 435/136; 530/350; 536/23.2

(58) Field of Search ............... 435/19, 196, 320.1, 435/267, 136; 530/350; 536/23.2

(56) References Cited

U.S. PATENT DOCUMENTS

| | | | | |
|---|---|---|---|---|
| 5,591,619 A | 1/1997 | Xin-Liang et al. | .......... | 435/201 |
| 5,720,971 A | 2/1998 | Beauchemin et al. | ....... | 424/438 |
| 5,824,533 A | 10/1998 | Li et al. | ............... | 435/209 |
| 5,882,905 A | 3/1999 | Saha et al. | ............... | 435/105 |

FOREIGN PATENT DOCUMENTS

| | | | | |
|---|---|---|---|---|
| EP | 0513140 B1 | 9/1995 | ............ | D21C/9/10 |
| GB | 2301103 | * 11/1996 | ............ | C12N/9/18 |
| WO | 98/46768 | 10/1998 | ............ | C12N/15/55 |
| WO | 00/14243 | 3/2000 | ........... | C12N/15/31 |

OTHER PUBLICATIONS

Fontes et al., Swiss Prot accession No. P51584, Oct. 1, 1996; Biochem. J. 307:151–158, 1995.*
Arakaki et al., Pir accession No. S58235, Mar., 1997.*
Grepinet et al., Swiss Prot accession No. P10478, Jul., 1989; J. Bacteriology 170:4582–4588, 1988.*
Li et al., Appl. Environ. Microbiol. 63:628–635, 1997.*
Bork, Genome Research, 10:348–400, 2000.*
Broun et al., Science 282:1315–1317, 1998.*
Van de Loo et al., Proc. Natl. Acad. Sci. 92:6743–6747, 1995.*
Seffernick et al., J. Bacteriol. 183(8):2405–2410, 2001.*

Barichievich and Calza (1990) "Supernatant Protein and Cellulase Activities of the Anaerobic Ruminal Fungus *Neocallimastix frontalis* EB188"; *Applied and Environmental Microbiology* 56(1):43–48.
Blum et al . (1999) "Characterization of a Feruloyl Esterase from the Anaerobic Fungus Orpinomyces sp. Strain PC–2"; Abstracts 99th General Meeting of the American Society for Microbiology, Chicago, IL. May 30–Jun. 3, 1999, vol. 99, pp. 430–431.
Borneman and Akin (1990) "Lignocellulose Degradation by Rumen Fungi and Bacteria: Ultrastructure and Cell Wall Degrading Enzymes" In: *Microbial and Plan Opportunities to Improve Lignocellulose Utilization by Ruminants*. D.E. Akin; L.G. Ljungdahl; J.R. Wilson; and P.J. Harris (Eds.) Elsevier Science Publishing Co. New York, NY. pp. 325–339.
Borneman et al. (1992) "Purification and Partial Characterization of Two Feruloyl Esterases from the Anaerobic Fungus Neocallimastix Strain MC–2" *Applied and Environmental Microbiology* 58:3762–3766.
Borneman et al. (1990) "Assay for trans–p–Coumaroyl Esterase Using a Specific Substrate from Plant Cell Walls" *Analytical Biochemistry* 190:129–133.
Castanares and Wood (1992) "Purification and Characterization of a Feruloyl/p–Coumaroyl Esterase from Solid–State Cultures of the Aerobic Fungus *Penicillium pinophilum*" *Biochemical Society Transactions* 20:275S.
Chen et al. (1995) "A Cyclophilin from the Polycentric Anaerobic Rumen Fungus Orpinomyces sp. Strain PC–2 is Highly Homologous to Vertebrate Cyclophilin B" *Proc. Natl. Acad. Sci. USA* 92:2587–2591.
Christov and Prior (1993) "Esterases of Xylan–Degrading Microorganisms: Production, Properties, and Significance" *Enzyme Microb. Technol.* 15:460–475.
Choi and Ljungdahl (1996) "Dissociation of the Cellulosome of *Clostridium thermocellum* in the Presence of Ethylenediaminetetraacetic Acid Occurs with the Formation of Truncated Polypeptides"; *Biochemistry* 35:4897–4905.

(List continued on next page.)

Primary Examiner—Rebecca E. Prouty
Assistant Examiner—Delia Ramirez
(74) Attorney, Agent, or Firm—Greenlee Winner and Sullivan, P.C.

(57) ABSTRACT

Described herein are four phenolic acid esterases, three of which correspond to domains of previously unknown function within bacterial xylanases, from XynY and XynZ of *Clostridium thermocellum* and from a feruloyl esterase of Ruminococcus. The fourth specifically exemplified phenolic acid esterase is a protein encoded within the genome of Orpinomyces PC-2. The amino acids of these polypeptides and nucleotide sequences encoding them are provided. Recombinant host cells, expression vectors and methods for the recombinant production of phenolic acid esterases are also provided. Further provided are methods for improving nutrient availability and ferulic acid availability when food or feed, or other material is treated with a phenolic acid esterase, desirably in combination with a xylanase.

36 Claims, 12 Drawing Sheets

OTHER PUBLICATIONS

Dalrymple and Swadling (1997) "Expression of a *Butyrivibrio fibrisolvens* E14 Gene (cinB) Encoding an Enzyme with Cinnamoyl Ester Hydrolase Activity is Negatively Regulated by the Product of an Adjacent Gene (cinR)" *Microbiology* 143:1203–1210.

Dalrymple et al. (1996) "Cloning of a Gene Encoding Cinnamoyl Ester Hydrolase from the Ruminal Bacterium *Butyrivibrio fibrisolvens* E14 by a Novel Method" *FEMS Microbiology Letters* 143:115–120.

De Vries et al. (1997) "The faeA Genes from *Aspergillus niger* and *Aspergillus tubingensis* Encode Ferulic Acid Esterases Involved in Degradation of Complex Cell Wall Polysaccharides" *Applied and Environmental Microbiology* 63:4638–4644.

Faulds and Williamson (1991) "The Purification and Characterization of 4–Hydroxy–3–Methoxycinnamic (Ferulic) Acid Esterase from *Streptomyces olivochromogenes*" *Journal of General Microbiology* 137:2339–2345.

Felix and Ljungdahl (1993) "The Cellulosome: The Exocellular Organelle of Clostridium" *Annu. Rev. Microbiol.* 47:791–819.

Ferreira et al. (1993) "A Modular Esterase from *Pseudomonas fluorescens* subsp. *cellulosa* Contains a Non–Catalytic Cellulose–Binding Domain" *Biochemical Journal* 294:349–355.

Flint et al. (1993) "A Bifunctional Enzyme, with Separate Xylanase and $\beta(1,3-1,4)$–Glucanase Domains, Encoded by the xynD Gene of *Ruminococcus flavefaciens*" *Journal of Bacteriology* 175:2943–2951.

Fontes et al. (1995) "Evidence for a General Role for Non–Catalytic Thermostabilizing Domains in Xylanases from Thermophilic Bacteria" *Biochem. J.* 307:151–158.

Genbank Accession No. AF047761, *Clostridium thermocellum* xylanase V and U, 1998.

Genbank Accession No. L48074, *Aspergillus fumigatus* dipeptidyl peptidase, 1997.

Genbank Accession No. M22624, *Clostridium thermocellum* xylanase Z, 1993.

Genbank Accession No. P31471, *Escherichia coli* 44.1 kD protein 1993.

Genbank Accession No. P51584, *Clostridium thermocellum* xylanase Y, 1996.

Genbank Accession No. S58235, Ruminococcus sp. xylanase, 1997.

Genbank Accession No. X83269, *Clostridium thermocellum* xylanase Y, 1995.

Genbank Accession No. Z49970, Ruminococcus sp. DNA for Xynl gene, 1995.

Grépinet et al. (1988) "Nucleotide Sequence and Deletion Analysis of the Xylanase Gene (xynZ) of *Clostridium thermocellum*" *Journal of Bacteriology* 170:4582–4588.

Kirby et al. (1998) "Plant Cell Wall Degrading Enzyme Complexes from the Cellulolytic Rumen Bacterium *Ruminococcus flavefaciens*" *Biochemical Society Transactions* 26:S169.

MacKenzie and Bilous (1988) "Ferulic Acid Esterase Activity from *Schizophyllum commune*" *Applied and Environmental Microbiology* 54:1170–1173.

McDermid et al. (1990) "Esterase Activities of *Fibrobacter succinogenes* subsp. succinogenes S85" *Applied and Environmental Microbiology* 56:127–132.

McSweeney et al. (1994) "Solubilization of Lignin by the Ruminal Anaerobic Fungus *Neocallimastix patriciarum*", *Applied and Environ. Microbiol.* 60(8):2985–2989.

McSweeney et al. (1998) "Butyrivibrio spp. and Other Xylanolytic Microorganisms from the Rumen have Cinnamoyl Esterase Activity" *Anaerobe* 4:57–65.

Ralph et al. (1995) "Lignin–Ferulate Cross–Links in Grasses: Active Incorporation of Ferulate Polysaccharide Esters Into Ryegrass Lignins" *Carbohydrate Research* 275:167–178.

Rogers et al. (1992) "Anaerobic Degradation of Lignocellulosic Substrates by a 1,4–$\beta$–Xylanolytic Clostridium species novum", *Int. Biodeterioration & Biodegradation* 29:3–17.

Sakka et al. (1996) "Identification and Characterization of Cellulose–Binding Domains in Xylanase A of *Clostridium stercorarium*" *Ann. NY Acad. Sci.* 782:241–251.

Sakka et al. (1993) "Nucleotide Sequence of the *Clostridium stercorarium* xynA Gene Encoding Xylanase A: Identification of Catalytic and Cellulose Binding Domains" *Biosci. Biotech. Biochem.* 57:273–277.

Tomme et al. (1995) "*Cellulose–Binding Domains: Classification and Properties*" In Enzymatic Degradation of Insoluble Carbohydrates, J.N. Saddler, M.H. Panner (Eds.), ACS Symposium Series, American Chemical Society, Washington, DC, pp. 142–163.

van Peij et al. (1998) "The Transcriptional Activator XlnR Regulates Both Xylanolytic and Endoglucanase Gene Expression in *Aspergillus niger*"; *Appl. & Environ. Microbiol.* 64(10):3615–3619.

Blum et al. (2000) "Feruloyl Esterase Activity of the *Clostridium thermocellum* Cellulosome Can Be Attributed to Previously Unknown Domans of XynY and XynZ"; *J. of Bacteriology* 182(5):1346–1351.

\* cited by examiner

Signal peptide

FAE domain

Unknown domain

PHENOLIC ACID ESTERASES, CODING SEQUENCES AND METHODS

CROSS REFERENCE TO RELATED APPLICATIONS

This application is a Continuation-in-part of U.S. patent application No. 09/390,234, filed Sep. 3, 1999, now U.S. Pat. No. 6,365,390 which application claims priority from U.S. Provisional Application No. 60/099,136, filed Sep. 4, 1998.

ACKNOWLEDGMENT OF FEDERAL RESEARCH SUPPORT

This invention was made, at least in part, with funding from the United States Department of Energy (Grant No. DE-FG05 93ER 20127). Accordingly, the United States Government has certain rights in this invention.

BACKGROUND OF THE INVENTION

The field of the present invention is the area of enzymes which degrade plant cell walls, and certain other substrates, in particular, the phenolic acid esterases, feruloyl esterases and/or coumaroyl esterase, and methods for using them in food compositions, feed compositions and supplements, nutriceuticals and in pulping.

Plant cell wall material is one of the largest sources of renewable energy on earth. Plant cell walls are composed mainly of cellulose, hemicelluloses, lignin and pectin. Arabinoxylan is one of the main constituents of hemicelluloses. It is composed of a chain of $\beta(1\rightarrow4)$ linked xylose units that are substituted by arabinose, acetate, and glucuronic acid. The arabinose has ester linked ferulic and p-coumaric acids [Bomeman et al. (1993) In: Hemicellulose and Hemicellulases, Coughlan and Hazlewood, Eds., pp. 85–102]. Ferulic acid has been shown to link hemicellulose and lignin [Ralph et al. (1995) Carbohydrate Research 275:167–178]. Feruloyl esterases are involved in breaking the bond between the arabinose and ferulic acid, thus releasing the covalently bound lignin from hemicelluloses. Feruloyl esterases have been found in many bacteria as well as fungi, but have not been extensively studied nor is there much sequence data available [Christov and Prior (1993) Enzyme. Microb. Technol. 15(6):460–75].

Clostridium thermocellum is a gram-positive bacterium that produces a multienzymatic structure termed the cellulosome. The cellulosome is one of the most active cellulose degrading complexes described to date. The cellulosome has a multi-polypeptide structure, including a scaffolding subunit which has nine cohesins binding to nine catalytic subunits, a dockerin domain for attachment to the cell wall, and a cellulose binding domain [Felix and Ljungdahl (1993) Annu. Rev. Microbiol. 47:791–819]. The catalytic subunits include endoglucanase, cellobiohydrolase, lichenase, and xylanase, many of which have been cloned and sequenced. They all have multidomain structures that include at least a dockerin domain for binding to the scaffolding domain, a linker, and a catalytic domain. They may also contain cellulose binding domains and fibronectin-like domains. There are reports that some enzymatic components may have more than one catalytic domain. Two of these are xylanase Y [XynY, Fontes et al. (1995) Biochem. J. 307:151–158] and xylanase Z [XynZ, Grépinet et al. (1988) J. Bacteriol. 170(10):4582–8]. XynY has a C-terminal domain whereas XynZ N-terminal domain without any functions determined. Although enzymes with dual catalytic domains (xylanase and βglucanase) have been found in other bacteria [Flint et al. (1993) J. Bacteriol. 175:2943–2951] neither phenolic acid esterase nor bifunctional enzymes have been found in C. thermocellum.

There is a need in the art for phenolic acid esterases, feruloyl esterases and/or coumaroyl esterases in pure form which degrade plant cell wall materials, and certain other substrates, for DNA encoding these enzymes to enable methods of producing ferulic acid and/or coumaric acid, as well as facilitating degradation of plant cell wall materials in the context of human, animal, fish or shellfish food, the pulping industry and in the area of nutriceuticals.

SUMMARY OF THE INVENTION

The present invention provides methods for improving nutrient availability in foods, especially plant-derived feedstuffs and foodstuffs with a significant non-starch polysaccharide content and/or with poorly digestible fiber. The methods comprise the step of combining the foodstuff or feedstuff with a feruloyl esterase as provided herein, desirably together with a xylanase, for example, the xylanase (XynA) protein derived from Orpinomyces PC-2. These enzymes can be prepared from their natural sources or the recombinant enzymes can be prepared using the teachings provided herein and in United States Patent No. 5,824,533 (Li et al., 1998) for the xylanase A of Orpinomyces PC-2. A foodstuff or feedstuff is combined with feruloyl esterase at a ratio of 0.1 to 200 units per kg dry weight of foodstuff or feedstuff. Where the xylanase A protein is also added, the xylanase ratio is 100 to 25,000 units per kg. An advantageous range is 500 to 10,000.U/kg or 1000 to 5000 U/kg. Where a beverage or liquid food or feed formulation is treated with feruloyl esterase or feruloyl esterase and xylanase A, the ratios are the same, with the calculation based on the dry weight of solids in the beverage or other liquid composition for consumption by a human or an animal.

The present invention further provides methods for improved pulping of plant material or recycled fiber materials, wherein the improvement comprises the step of adding a feruloyl acid esterase to the pulping mixture and incubating under conditions allowing enzymatic action of the ésterase on the non-starch polysaccharides in the mixture. The mixtures desirably contain a combination of feruloyl esterase and xylanase A. In pulping, the esterase is present in the pulping mixture at a ratio of 0.1 to 200 U/kg dry weight of pulp or fiber, and where xylanase A is present, the xylanase is present at a ratio of from 100 to 25,000 U/kg, desirably from 500 to 10,000, or from 1000 to about 5000 U/kg fiber or pulp dry weight.

The present invention further provides compositions comprising a feruloyl esterase protein. Desirably the composition further comprises a xylanase optionally xylanase A from Orpinomyces PC-2. These compositions can be liquid (nonconcentrated solution or suspension) or dry (e.g., freeze-dried). The user then adds the liquid composition to food, feed or fiber, or the dry composition can be reconstituted before or upon addition to a food, feed or pulp.

The present invention further provides methods for improving the availability of ferulic acid from plant material for human, animal, fish or shellfish nutrition or health benefit. A feruloyl esterase composition described herein or a combination of a feruloyl esterase together with xylanase A is (are) added to a plant-derived foodstuff or feedstuff prior to consumption. Alternatively, a composition containing a feruloyl esterase digest or a feruloyl esterase—xylanase A digest of plant cell wall-containing material can be provided for use as a nutritional or nutriceutical supplement.

Herein are described novel phenolic acid esterases, having feruloyl esterase and coumaroyl esterase activities, and coding sequences for same.

One phenolic acid esterase corresponds to a domain of previously unknown function from xylanase Y of *Clostridium thermocellum*. The recombinantly expressed domain polypeptide is active and has an amino acid sequence as given in FIG. 1 as "XynY_Clotm." The nucleotide sequence encoding the esterase polypeptide is given in Table 5, nucleotides 2383–3219, exclusive of translation start and stop signals. See also SEQ ID NOs:11 and 12.

A second phenolic acid esterase corresponds to a domain of previously unknown function of xylanase Z from *C. thermocellum*. The amino acid sequence of the esterase domain, which also is active when expressed as a recombinant polypeptide, is given in FIG. 1 as "XynZ_Clotm." The nucleotide sequence encoding this polypeptide is given in Table 6, nucleotides 58–858. Further described is a phenolic acid esterase polypeptide additionally comprising a cellulose binding domain. A specifically identified cellulose binding domain has an amino acid sequence as given in Table 6, 289–400, with a corresponding coding sequence as given in Table 6, nucleotides 867–1200. See also SEQ ID NOs:13 and 14.

An additional object of the present invention is a phenolic acid esterase (i.e., a feruloyl esterase) derived from a previously uncharacterized portion of a Ruminococcus xylanase (See FIG. 1). The coding (nucleotides 2164–2895, exclusive of translation start and stop signals) and deduced amino acid sequences (amino acids 546–789) are given in Table 10. See also SEQ ID NOs:15 and 16.

A feruloyl (phenolic acid) esterase is prepared from the anaerobic fungus Orpinomyces PC-2. The coding sequence and deduced amino acid sequences of the mature esterase protein are given in Table 9, and the purification of the Orpinomyces enzyme is described herein below. See also SEQ ID NOs:17 and 18.

Recombinant production of the phenolic (especially ferulic) acid esterases is described. *Escherichia coli, Bacillus subtilis*, Streptomyces sp., *Saccharomyces cerevisiae, Aureobasidium pullulans, Pichia pastoris*, Trichoderma, *Aspergillus nidulans* or any other host cell, including plants, suitable for the production of a heterologous protein can be transfected or transformed with an expression vector appropriate for the chosen host. Compatible combinations of vectors and host cells are well known in the art, as are appropriate promoters to be used to direct the expression of a particular coding sequence of interest. The recombinant host cells are cultured under conditions suitable for growth and expression of the phenolic acid esterase, and the recombinant esterase is then collected or the recombinant host cells in which the esterase has been produced are collected. The coding sequence of the esterase can be operably linked to a nucleotide sequence encoding a signal peptide which is known in the art and functional in the desired host cell if secretion of the esterase into the culture medium is desired. In that case, the culture medium serves as the source of esterase after growth of the host cells.

It is recognized by those skilled in the art that the DNA sequences may vary due to the degeneracy of the genetic code and codon usage. All DNA sequences which encode a phenolic acid esterase polypeptide having a specifically exemplified amino acid sequence are included in this invention, including DNA sequences encoding them having an ATG preceding the coding region for the mature protein and a translation termination codon (TAA, TGA or TAG) after the coding sequence.

Additionally, it will be recognized by those skilled in the art that allelic variations may occur in the phenolic acid esterase polypeptide coding sequences which will not significantly change activity of the amino acid sequences of the polypeptides which the DNA sequences encode. All such equivalent DNA sequences are included within the scope of this invention and the definition of a phenolic acid esterase. The skilled artisan will understand that the amino acid sequence of an exemplified phenolic acid esterase polypeptide and signal peptide(s) can be used to identify and isolate additional, nonexemplified nucleotide sequences which will encode functional equivalents to the polypeptides defined by the amino acid sequences given herein or an amino acid sequence of greater than 40% identity thereto and having equivalent biological activity. All integer percents between 40 and 100 are encompassed by the present invention. DNA sequences having at least about 75% homology to any of the ferulic acid esterases coding sequences presented herein and encoding polypeptides with the same function are considered equivalent to thereto and are included in the definition of "DNA encoding a phenolic acid esterase." Following the teachings herein, the skilled worker will be able to make a large number of operative embodiments having equivalent DNA sequences to those listed herein.

Feruloyl esterase proteins are characterized by at least a portion having from at least about 40% amino acid sequence identity with an amino acid sequence as given in SEQ ID NO:18, amino acids 227 to 440 (within the feruloyl esterase protein of Orpinomyces PC-2. All integer percent identities between 40 and 100% are also contemplated. Similarly, feruloyl esterase proteins can have from about 40% to about 100% identity with an amino acid sequence from the group comprising amino acids 581 to 789 of SEQ ID NO:16, amino acids 845 to 1075 of SEQ ID NO:12, amino acids 69 to 286 of SEQ ID NO:14, amino acids 69 to 307 of SEQ ID NO:14, and amino acids 69 to 421 of SEQ ID NO:14. Specifically exemplified feruloyl esterases are characterized by amino acid sequences from the group comprising amino acids 227 to 440 of SEQ ID NO:18, amino acids 581 to 789 of SEQ ID NO:16, amino acids 845 to 1075 of SEQ ID NO:12, amino acids 69 to 286 of SEQ ID NO:14, amino acids 69 to 307 of SEQ ID NO:14, and amino acids 69 to 421 of SEQ ID NO:14. Feruloyl esterase proteins include those having the following amino acid sequences: SEQ ID NO:18, amino acids 1 to 530; SEQ ID NO:12, amino acids 795 to 1077; SEQ ID NO:16, amino acids 546 to 789; SEQ ID NO:14, amino acids 20 to 286; SEQ ID NO:14, amino acids 20 to 307; and SEQ ID NO:14, amino acids 20 to 421.

Specifically exemplified nucleotide sequences encoding the feruloyl esterase proteins include the following: SEQ ID NO:17, nucleotides 1 to 1590; SEQ ID NO:11, nucleotides 2582–3430; SEQ ID NO:15, nucleotides 2164 to 2895; SEQ ID NO:13, nucleotides 158 to 958; SEQ ID NO:13, nucleotides 158 to 1021; SEQ ID NO:13, nucleotides 158 to 1363.

The phenolic acid esterase coding sequences, including or excluding that encoding a signal peptide, can be used to express a phenolic acid esterase in recombinant fungal host cells or plant cells as well as in bacteria, including without limitation, Bacillus spp., Streptomyces sp. and *Escherichia coli*. Any host cell in which the signal sequence is expressed and processed may be used. Preferred host cells are Aureobasidium species, Aspergillus species, Trichoderma species and *Saccharomyces cerevisiae*, as well as other yeasts known to the art for fermentation, including *Pichia pastoris* [See, e.g., Sreekrishna, K. (1993) In: *Industrial Microorganisms: Basic and Applied Molecular Genetics*, Baltz, R. H., et al. (Eds.) ASM Press, Washington, D.C. 119–126].

Filamentous fungi such as Aspergillus, Trichoderma, Penicillium, etc. are also useful host organisms for expression of the DNA of this invention. [Van den Handel, C. et al. (1991) In: Bennett, J. W. and Lasure, L. L. (Eds.), *More Gene Manipulations in Fungi*, Academy Press, Inc., New York, 397–428].

BRIEF DESCRIPTION OF THE DRAWINGS

FIG. 1 shows amino acid sequence alignment of the exemplified phenolic acid esterases. Sequences are xylanase Z [XynZ_Clotm, Grépinet et al. (1988) supra], xylanase Y [XynY_Clotm, Fontes et al. (1995) supra] of *C. thermocellum*, xylanase A (XynA_Rumin) of a Ruminococcus sp, and a hypothetical 44-kDa protein of *E coli* (Genbank Accession Number P31471) (SEQ ID NO:19). Amino acid numbering was the same as in the databases. Dots represent gaps introduced to optimize alignment, and are treated as mismatched in calculations of sequence relatedness (similarity or identity). The partial amino acids are derived from SEQ ID NO:20, SEQ ID NO:12, SEQ ID NO:16, SEQ ID NO:19 and SEQ ID NO:18.

FIG. 9 shows alignment of protein sequences exhibiting homology to the Orpinomyces feruloyl esterase. Sequences are: faea_orpin, Orpinomyces sp. strain PC-2 FaeA; xyna_rumin, xylanase from Ruminococcus sp. (Genbank Accession Number S58235); yiel_ecoli hypothetical 44kDa protein from *E. coli* (Genbank Accession Number P31471); xyny_clotm, xylanase Y from *C. thermocellum* (Genbank Accession Number P51584); xynz_clotm, xylanase Z from *C. thermocellum* (Genbank Accession Number M22624); dppv_asprf, dipeptidyl peptidase from *A. fumigatus* (Genbank Accession Number L48074) (SEQ ID NO:20). The partial sequences are taken from. SEQ ID NO:18, SEQ ID NO:16, SEQ ID NO:22, SEQ ID NO:12, SEQ ID NO:14 and SEQ ID NO:20.

DETAILED DESCRIPTION OF THE INVENTION

Figure 2:
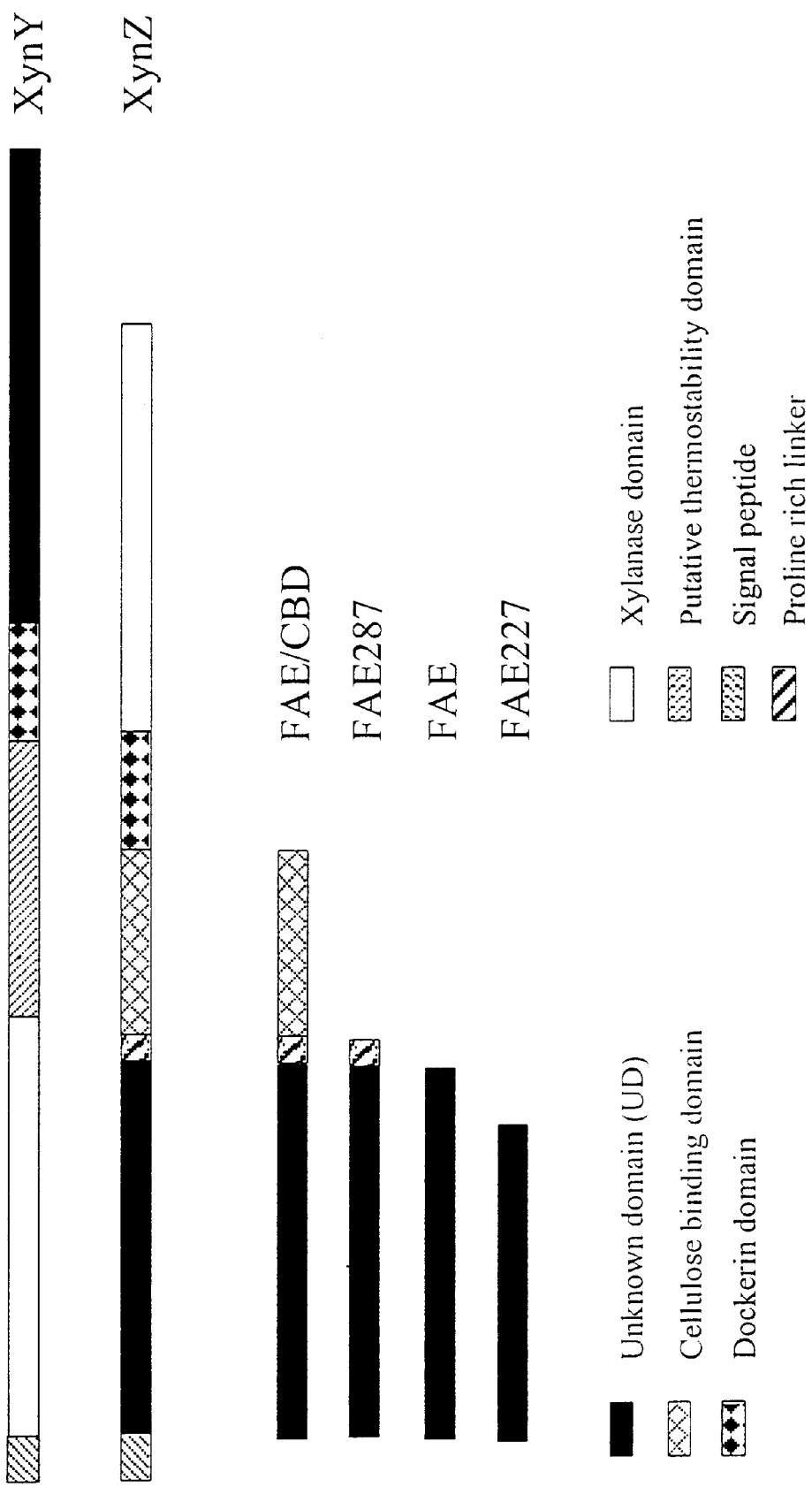
FIG. 2 shows the domain organizations of two cellulosomal components, xylanase Y and xylanase Z of *C. thermocellum*.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Trp, Tryptophan; and Y, Tyr, Tyrosine.

Additional abbreviations used in the present specification include the following: aa, amino acid(s); bp, base pair(s); CD, catalytic domain(s); GCG, Genetics Computer Group, Madison, Wiss.; CMC, carboxymethyl cellulose; FPase, filter paper-ase; HMWC, high-molecular weight complex (es); IPTG, isopropyl-β-D-thiogalactoside; OSX, oat spelt xylan; ORF, open reading frame; RBB, remazol brilliant blue; pfu, plaque forming units, FAXX, (0-{5-0-[(E)-feruloyl]-α-L-arabinofuranosyl}-(1→3)-0-β-D-xylopyranosyl-(1→4)-D-xylopyranose.

In the present context, plant-derived means material from a plant or plant part. The material can be seeds, grain, foliage, stems, woody or fibrous material, and the like.

In this application derived from a microorganism means that a nucleic acid segment or a protein is purified or taken directly from that microorganism or a culture thereof; A protein produced by genetically engineered (recombinant) using DNA sequence information from the microorganism is also considered derived from that microorganism.

Genes encoding feruloyl esterase (faeA) have been cloned from *Aspergillus niger* and *Aspergillus tubingensis* and the deduced amino acid sequences bear close similarity to lipases [de Vries et al. (1997) *Appl. Environ. Microbiol*. 63:4638–4644]. Expression of these gene products is regulated by the xlnR gene product [van Peij et al. (1998) *Appl. Environ. Microbiol*. 64:3615–3619]. Other genes include the xylD gene from *Pseudomonas fluorescens* subsp. cellulosa, the gene product of which has a higher specificity for acetyl groups than feruloyl groups [Ferreira et al. (1993) *Biochemical J*. 294:349–355] and two genes from *Butyrivibro fibrisolvens* termed cinA and cinB [Dalrymple and Swadling (1997) *Microbiology* 143:1203–1210; Dalrymple et al. (1996) *FEMS Microbiol. Lett*. 143:115–120]. These genes are believed to be regulated by the cinR gene product which may itself be regulated by FAXX [Dalrymple and Swadling (1997) supra]. Esterase activity has also been studied in

*Streptomyces olivochromogenes* [Faulds and Williamson (1991) *J. Gen. Microbiol.* 137:2339–2345], *Schizophyllum commune* [MacKenzie and Bilous (1988) *Appl. Environ. Microbiol.* 54:1170–1173], *Penicillium pinophillum* [Castanares and Wood (1992) *Biochem. Soc. Trans.* 20:275S], and *Fibrobacter succinogenes* [McDermid et al. (1990) *Appl. Environ. Microbiol.* 56:127–132].

As described herein, feruloyl esterases are found as part of xylanases from the *Clostridium thermocellum* cellulosome or as an individual enzyme, for example, from Orpinomyces sp. PC-2. Xylanases Y and Z from *C. thermocellum* are composed of a xylanase domain, a linker domain, and other domains as well as a domain to which no function has been assigned. We found partial sequence homology between these enzyme and the feruloyl esterase of Orpinomyces in the region of the previously unknown domains and demonstrated that these domains indeed encode feruloyl esterases. Herein, we also report the purification, cloning, and partial characterization of the feruloyl esterase from Orpinomyces sp. strain PC-2.

Figure 1:
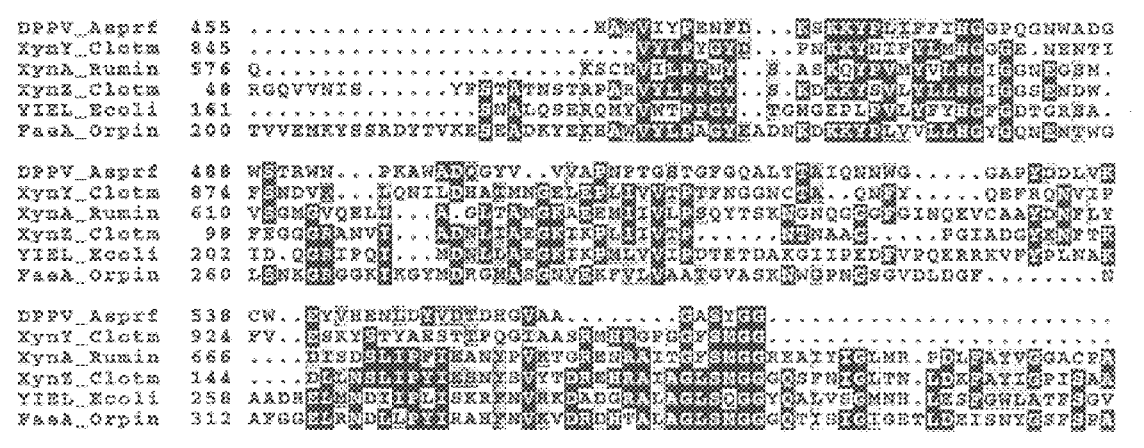

Anaerobic fungi produce high levels of phenolic esterases [Bomeman and Akin (1990) In: Microbial and Plant Opportunities to Improve Lignocellulose Utilization by Ruminants. D. E. Akin, L. G. Ljungdahl, J. R. Wilson, and P. J. Harris (Eds.). Elsevier Science Publishing Co. New York, pp. 325–340] and two feruloyl esterases of the anaerobic fungus Neocallimastix MC-2 were purified and characterized [Borneman et al. (1992) *Appl. Environ. Microbiol.* 58:3762–3766]. A cDNA coding for a feruloyl esterase (FaeA) of the anaerobic fungus Orpinomyces PC-2 was cloned and sequenced by the present inventors. FASTA and BLAST searches showed that the catalytic domain of the Orpinomyces FaeA was over 30% identical to sequences coding for unknown domains (UD) in the databases including the carboxy terminal region of XynY Fontes et al. (1995) supra], the amino terminal region of XynZ [Grépinet et al. (1988) supra], a hypothetical polypeptide of *E. coli* (Genbank Accession Number P31471), and the carboxy terminal region of a Ruminococcus xylanase [Genbank Accession No. S58235] (FIG. 1). No function had been previously assigned to the sequences homologous to the Orpinomyces FaeA. XynY consists of multiple domains including a family F xylanase domain, followed by a putative thermostability domain, a dockerin, and the UD [Fontes et al. (1995) supra]. Similarly, XynZ is also multi-domain enzyme containing the UD, a family VI cellulose binding domain, a dockerin, and a family 10 xylanase domain [Grépinet et al. (1988) supra; Tomme et al. (1995) In: *Enzymatic Degradation of insoluble Carbohydrates*. J. N. Saddler, M. H. Panner (Eds.), ACS Symposium Series, American Chemical Society, Washington, D.C., pp. 142–163]. Both XynY and XynZ are believed to be components of the cellulosome (FIG. 2). The Orpinomyces FaeA together with those homologous sequences, however, failed to show significant homology to the recently published feruloyl esterases (FaeA) of *Aspergillus niger* and *A. tubingensis* [de Vries et 5 al. (1997) supra]. The sequence analysis implies that a new type of feruloyl esterase is encoded by the Orpinomyces cDNA and the homologous sequences described above.

We have determined that *C. thermocellum* produces feruloyl esterase activity under the conditions when the cellulosome production is induced. The bacterium was cultivated on low concentration (0.2%, w/v) of Avicel, and under this growth condition, most of the substrate was consumed and cellulosomes released into culture medium, as indicated by the activities on Avicel and xylan (Table 2). Most of the feruloyl esterase activity (97.9%) was found in the culture medium (Table 2). It is well documented that cellulosomes of *C. thermocellum* are readily adsorbed to cellulose [Morag et al. (1992) *Enzyme Microb. Technol.* 14:289–292; Choi and Ljungdahl (1996) *Biochemistry* 35:4897–4905], and thus Avicel adsorption was used to assess association of the feruloyl activity with cellulosomes. As shown in Table 2, 97.1% of total feruloyl activity was removed from the culture medium by Avicel treatment, even higher than the percentages of cellulase (80.5%) and xylanase (73.3%) activities removed. These data indicate that feruloyl esterases produced by *C. thermocellum* possess cellulose-binding ability through either a cellulose-binding domain or the cellulosomes. XynZ has a family VI cellulose binding domain [Grépinet et al. (1988) supra; Tomme et al. (1995) supra] and a docking domain between the CBD and the dockerin, whereas XynY contains a docking domain.

Figure 3:
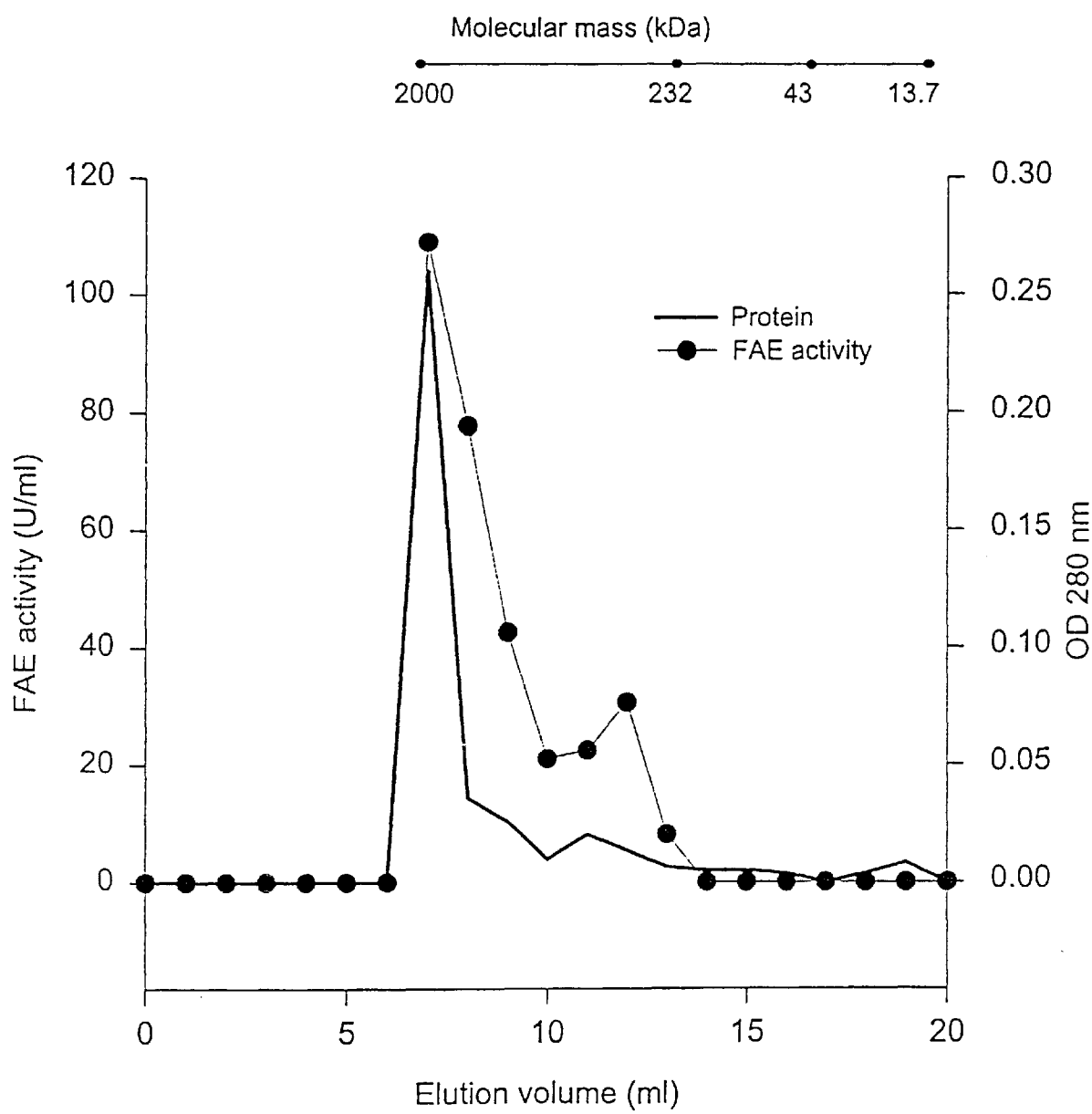
FIG. 3 illustrates the results of Superose 6 gel filtration of proteins eluted from Avicel adsorption of *C. thermocellum* culture supernatant. Fractions (0.5 ml) were collected and assayed for protein and feruloyl esterase activity. Molecular mass standards (Sigma Chemical Company, St. Louis, Mo.) including blue dextran (2,000 kDa), catalase (232 kDa), ovalbumin (43 kDa), and ribonuclease A (13.7 kDa) were run under identical conditions and their elution positions were indicated.

Cellulosomes eluted from Avicel adsorption were analyzed by gel filtration chromatography using a Superose 6 column to assess the sizes of proteins containing feruloyl esterase activity in the native state. The majority of the proteins were eluted in fractions containing molecules with sizes around 2.0 million daltons (FIG. 3), characteristic of cellulosomes eluted from gel filtration [Choi and Ljungdahl (1996) supra]. Feruloyl esterase activity in the fractions correlated well with fractions of cellulosomes. No activity was found in fractions with protein molecules less than 200 kDa, indicating that feruloyl esterase activity resides in the cellulosome.

The UD coding region of XynY and various regions of XynZ were over-expressed in *E. coli* using the pRSET system (Invitrogen, Carlsbad, Calif.). Constructs spanning the XynY UD sequence, XynZ UD alone, and UD plus the CBD sequence in PRSET gave high levels of feruloyl esterase activity whereas cell-free extracts of *E. coli* harboring the pET-21 b recombinant plasmid failed to hydrolyze FAXX. Constructs with 20 and 40 amino acid residues deleted from the C-terminus of the XynZ UD did not hydrolyze FAXX, indicating that XynZ sequence from the end of the signal peptide up to amino acid 288 was required to form an active feruloyl esterase. The heterologous protein band of the UD constructs without IPTG induction on SDS-PAGE analysis reached 40–50% of total protein. Both growth rates and levels of feruloyl activity of the constructs with the XynY and XynZ sequences were lower with IPTG induction than without induction. Without wishing to be bound by theory, it is believed that low level of T7 polymerase in *E. coli* BL21 (DE3) strain was ideal for the expression of the inserted genes in pRSET B, and over-expression of T7 polymerase gene by IPTG induction resulted in toxic levels of feruloyl esterase production.

Figure 4:
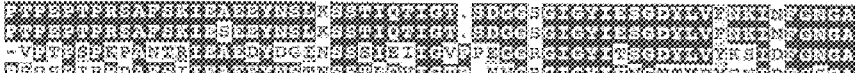
FIG. 4 presents amino acid sequence alignment of family VI cellulose binding domains. Sequences are xylanase U (XynU_Clotm), xylanase V (XynV_Clotm) (Fernandes et al., 1998, Genbank Accession Number AF047761), and xylanase Z [XynZ_Clotm, Grépinet et al. (1988) supra] of *C. thermocellum* and xylanase A [XynA Closr, Sakka et al. (1993) *Biosci. Biotech. Biochem*. 57:273–277; Sakka et al. (1996) *Ann. N.Y. Acad Sci*. 782:741–751] of *C. stercorarium*. The sequences presented are portions of those sequences presented in SEQ ID NO:12, SEQ ID NO:14 and SEQ ID NO:24.

Amino acid residues 328 to 419 of XynZ were homologous to two repeated CBDs of *C. stercorarium* XynA [Sakka et al. (1993) supra; Sakka et al. (1995) supra] (FIG. 4). This domain has been recently classified as a family VI CBD [Tomme et al. (1995) supra]. Constructs containing the UD alone and both the UD plus the putative CBD of XynZ were purified from recombinant *E. coli* cultures. The majority of feruloyl esterase activity of the polypeptide containing both domains was removed by Avicel and acid swollen cellulose adsorption but not with the UD alone, indicating that strong cellulose binding capability resides in the family VI cellulose binding domain of XynZ. Cellulose-binding ability was confirmed with native gel retardation analysis.

Figure 6A:
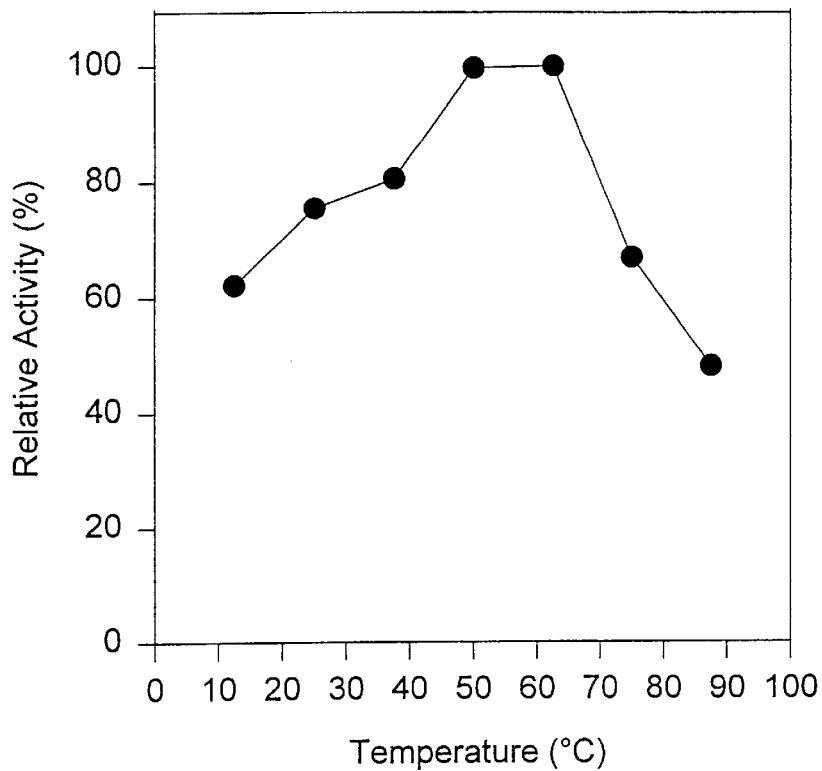
FIGS. 6A and 6B, respectively, illustrate the effects of temperature and pH on feruloyl esterase activity of the *C. thermocellum* XynZ FAE/CBD. Buffer used for evaluating temperature effects was 50 mM sodium citrate, pH 6.0. Assays mixtures with a pH range from 2 to 10 were formulated by using a universal phosphate buffer system.
Figure 6B:
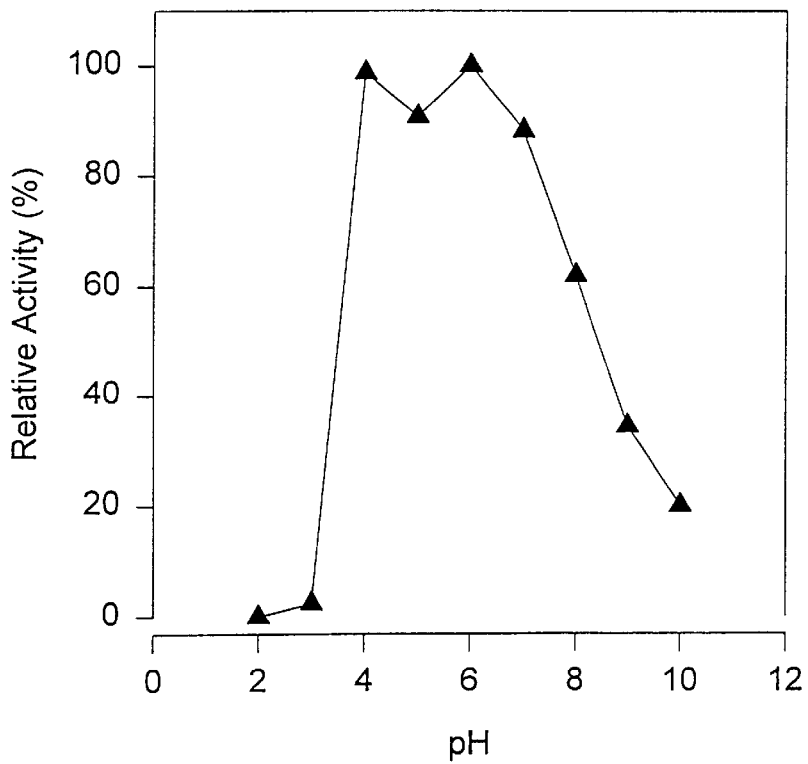

The polypeptide of the Fae domain plus CBD (FAE/CBD) has been purified from *E. coli* cell free extract to almost homogeneity after a single step of heating at 70° C. for 30 min. Over 200 milligrams of the FAE/CBD were obtained from 2.5 gram crude proteins (Table 3). The purified FAE/CBD had a mass of 45 kDa as revealed by SDS-PAGE (FIG. 6), consistent with the calculated size (46.5 kDa). This size was also consistent with what was seen on gel filtration. There was no evidence for aggregation of the recombinant polypeptides produced in *E. coli*.

The purified protein had a Vmax of 13.5 µmol ferulic acid released min-1 mg-1 and Km of 3.2 mM using $FAX_3$ as substrate. The enzyme had the highest specific activity toward FAXX, but it was almost as active as toward $FAX_3$ (Table 4). The protein released low levels of ferulic acid from ethyl ferulic acid, ground wheat bran, and Coastal Bermuda grass and p-coumaroyl acid from $PAX_3$ and ethyl-p-coumaroyl acid. The protein lacked activity toward CMC, Avicel, p-nitrophenyl (pNP)-arabinopyranoside, pNP-glucopyranoside, pNP-xylopyranoside, and pNP-acetate.

The recombinant FAE/CBD enzyme had high levels of activity between pH 3.8 and 7 and temperatures between 37 and 65° C. (FIG. 6). The FAE/CBD was stable at temperatures up at 65° C. for 6 hours.

In order to understand how microorganisms breakdown plant cell wall material, we chose to study enzymes from *Clostridium thermocellum*. In particular, XynY and XynZ from this organism were originally thought to contain a xylanase domain and second domain of unknown function. We have now demonstrated that the function of this domain is that of a feruloyl esterase, which is functional in the cellulosome or as a free protein. Feruloyl esterases are important for the complete degradation of plant cell wall material. These enzymes are produced by several organisms, but they have not been found in a bifunctional enzyme.

A feruloyl esterase from Orpinomyces PC-2 was purified and internal fragments of the enzyme were used to screen the Orpinomyces PC-2 cDNA library. A partial clone was sequenced and showed homology to XynZ. A BLAST analysis showed that this enzyme, along with XynY, had domains of unknown function.

The high temperature stability of the enzyme is surprising because no other thermophilic feruloyl esterases have been reported until the present disclosure of the *C. thermocellum* thermotolerant feruloyl esterases. The Orpinomyces PC-2 enzyme has substrate specificity for both feruloyl and p-coumaroyl esterified substrates. The clostridial enzymes are the first from bacteria to have such a dual role. Although the Orpinomyces enzyme is not a true p-coumaroyl esterase, no p-coumaric acid esterases have been found in bacteria to date.

Applications for the enzymes of the present invention include producing ferulic acid from wheat bran or agricultural byproducts, using the enzyme to treat grasses or other plant materials or other plant materials used in the pulp and paper industries, feed processing, and as a food additive. These thermostable enzymes have advantages over other enzymes since they are economically and easily purified, they have high temperature optima, good thermostability, and they are stable over a wide range of pH values.

Feruloyl esterases and xylanase act synergistically to the release of ferulic acid and reducing sugars from lignocellulosic material [Borneman et al. (1993) supra]. In *C. thermocellum* XynY and XynZ, we hypothesize that this is more efficient due to the incorporation of both enzymes into one. We believe there is a multicutting event catalyzed by these enzymes much like the multicutting event in the cellulosome itself which leads to more efficient hydrolysis of plant cell wall material. The substrate, arabinoxylan could be passed from one active site to another, which would eliminate the process of each of two enzymes having to bind to the substrate and then release it for the other enzyme to attack.

XynY and XynZ are enzymatic components of the *Clostridium thermocellum* cellulosome. These components have a multi-domain structure which includes a dockerin domain, a catalytic xylanase domain, and a domain of unknown function. The previously unknown domains in XynY and XynZ have been found to have phenolic esterase activity. These domains have some amino acid homology to that of a phenolic esterase from the anaerobic fungus Orpinomyces sp. strain PC-2. Secondly, purified cellulosomes from *C. thermocellum* hydrolyze (O-{5-O-[(E)-feruloyl]-(-L-arabinofuranosyl}-(1(3)-O-(-D-xylopyranosyl-(1(4)-D-xylopyranose) (FAXX) and {5-O-[(E)-feruloyl]-[O-(-D-xylopyranosyl-(1(2)]-O-(-L-arabinofuranosyl-[1(3)]}-O-(-D-xylopyranosyl-(1(4)-D-xylopyranose ($FAX_3$) yielding ferulic acid as a product, thus indicating the presence of a phenolic acid esterase. Intracellular and extracellular fractions lacking cellulosomes had insignificant amounts of phenolic acid esterase activity which confirmed that the activity resided with the cellulosome. The final proof was obtained by cloning the domains of XynY and XynZ into *Escherichia coli*. The domains were expressed and found to possess phenolic acid esterase activities with FAXX and $FAX_3$ as substrates.

Nucleotides corresponding to regions of DNA encoding amino acids in XynZ (Genbank Accession Number M22624) from 20–421 and in XynY (Genbank Accession Number X83269) from 795–1077 were overexpressed in *E. coli* using the pET and pRSET systems respectively. The XynZ sequence will henceforth be referred to as XynZ FAE/CBD since it incorporates the family VI CBD, and the XynY protein is XynY FAE since it only contains a catalytic domain. The cell free extracts containing the expressed proteins each hydrolyzed FAXX with release of ferulic acid (FA) which suggests that these proteins are feruloyl esterases. The expressed protein from the construct containing XynY FAE had a molecular weight of 31 kDa, consistent with the sequence data. Constructs containing XynZ FAE/CBD produced a protein with a molecular mass of 45 kDa as analyzed by SDS-PAGE. The protein was expressed without IPTG induction at a level of 8% of the total protein. Levels of feruloyl esterase activity of the constructs with the XynY FAE and XynZ FAE/CBD sequences were lower with IPTG induction than without induction. Since these proteins had similar sequences and similar function coupled with the fact that XynZ had higher expression levels than XynY, we decided to focus our attention on XynZ and subsequent experiments will refer to that protein.

Constructs were made which corresponded to proteins with amino acids from the original *C. thermocellum* XynZ sequence of 20–307 (FAE287), 20–286 (FAE) and 20–247 (FAE227) (with reference to SEQ ID NO:14 and FIG. 2). FAE287 is missing the CBD, but contains a proline rich linker which separates the CBD from the FAE domain while FAE does not contain this linker. When these constructs were expressed in *E. coli* in the same manner as XynZ FAE/CBD, they both exhibited feruloyl esterase activity. Thus, the removal of the 114 amino acids of the CBD did not have a detrimental effect on the activity. XynZ FAE/CBD bound to acid swollen cellulose very weakly, while the other constructs missing the CBD did not bind acid swollen cellulose at all. FAE227 was an inactive but expressed enzyme. Neither the CBD nor the linker is necessary for activity, but amino acids 247–266 are necessary for generation of an active enzyme. Since neither the linker region nor the CBD is necessary for activity, we used the smallest construct which still retained activity, FAE, for subsequent experiments.

Figure 5:
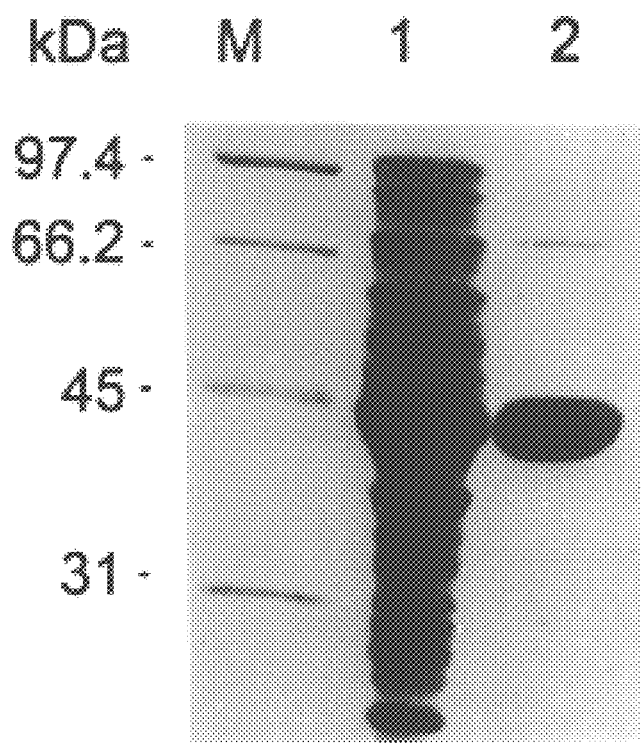
FIG. 5 shows the results of SDS-PAGE analysis of the *C. thermocellum* XynZ ferulic acid esterase+cellulose binding domain (FAE/CBD) over-expressed in *E. coli*. Lane M, low range protein standard markers (Bio-Rad Laboratories, Hercules, Calif.) including phosphorylase B (97.4 kDa), serum albumin (66.2), ovalbumin (45 kDa), and carbonic anhydrase (31 kDa); lane 1, *E. coli* cell free extract; lane 2, heat-treated cell free extract.

The XynZ FAE/CBD polypeptide was purified from *E. coli* cell free extract after a single step of heat treatment at 70° C. for 30 min. Over 200 mg of the XynZ FAE/CBD were obtained from 2.5 gram of crude protein (Table 3). The purified XynZ FAE/CBD had a mass as stated previously of 45 kDa as revealed by SDS-PAGE (FIG. 5), consistent with the calculated size (46.5 kDa). There was no evidence for aggregation of the feruloyl esterase produced in *E. coli*, and SDS-PAGE gels showed that protein which was removed from the cell free extract by centrifugation had no insoluble protein which could be attributed to inclusion bodies.

The purified protein had a Vmax of 12.5 μmol ferulic acid released min-1 mg-1 and Km of 5 mM using FAX3 as substrate. The enzyme had the highest specific activity towards FAXX but was almost as active toward FAX3 (Table 4). The protein was able to release low levels of FA from ethyl ferulic acid, ground wheat bran, and Coastal Bermuda grass and p-coumaric acid (PCA) from PAX3 and ethyl-p-coumarate. The protein lacked activity toward CMC, Avicel, p-nitrophenyl (pNP)-arabinopyranoside, pNP-glucopyranoside, pNP-xylopyranoside, and pNP-acetate. Isoelectric focusing gel electrophoresis showed that the protein had a pI of 5.8.

The FAE polypeptide of XynZ was also expressed and purified to homogeneity. A purification scheme is shown in Table 3B. The protein was expressed in a manner similar to that for XynZ FAE/CBD. The heat treatment step also resulted in 200 mg of protein, but the protein was not pure. An additional step involving gel filtration resulted in a pure enzyme with a Vmax of 28.2 μmol ferulic acid released min-1 mg-1 and Km of 10.5 mM using FAX3 as substrate. FAE was inhibited by ferulic acid but not by xylose or arabinose. The FAE had a temperature optimum between 30° and 70° C. (FIG. 6A) and had high level activity between pH 4 and 7 (FIG. 6B) The enzyme was stable at temperatures up at 70° C. for 6 hours, and in a similar experiment, FAE/CBD also was stable at 70° C. At 80° C., the relative activity of FAE decreased to around 50% after three hours of incubation, and most of the relative activity was destroyed after 1 hour of incubation at 90° C.

Anaerobic microorganisms do not readily degrade lignin, but are able to solubilize it. Anaerobic fungi are able to solubilize but not metabolize lignin, and it is suggested that the released lignin was carbohydrate linked [McSweeney et al. (1994) *Appl. Environ. Microbiol.* 60:2985–2989]. The data herein indicate that feruloyl esterases are responsible for lignin solubilization. Most studies of the cellulosome of *C. thermocellum* has been directed toward its celluloytic activity. It also has xylanases which we have shown are bifunctional enzymes with feruloyl esterase activity. The cellulosome should be efficient in the degradation of arabinoxylan. It has been previously shown that *Clostridium xylanolyticum* released aromatics into the culture medium when grown on lignocellulosic material [Rogers et al. (1992) *International Biodeterioration & Biodegradation* 29:3–17].

XynY and XynZ each contain a glycosyl hydrolase family 10 catalytic domain in addition to the FAE catalytic domain. The xylanase domain of XynZ has been well studied, that construct has been crystallized, and the three dimensional structure solved [Dominguez et al. (1995) *Nat. Struct. Biol.* 2:569–576; Souchon et al. (1994) *J. Mol. Biol.* 235:1348–1350]. In general, xylanases are thought to be sterically hindered by groups substituted on the xylan backbone. Feruloyl esterase and xylanase have been shown to act synergistically for the release of ferulic acid and reducing sugars from lignocellulosic material [Bomeman et al. (1993) supra]. In XynY and XynZ we hypothesize that this event has been made more efficient by the incorporation of both FAE and xylanase catalytic domains into one enzyme. Without wishing to be bound by theory, we believe that there is a multicutting event catalyzed by these enzymes much like the multicutting event in the cellulosome itself which leads to more efficient hydrolysis of plant cell wall material. Bifunctional enzymes like XynY and XynZ form a dumbbell-like shape which attacks the arabinoxylan polysaccharide and the substrate is passed from one active site to another, eliminating the relatively inefficient two enzyme process in which one has to bind to the substrate and then release it for the other enzyme to attack. The existence of multidomain enzymes such as the sea whip coral peroxidase-lipoxygenase [Koljak et al. (1997) *Science* 277:1994–1996] and a xylanase-β(1,3-1,4)-glucanase from *Ruminococcus flavifaciens* [Flint et al. (1993) *J. Bacteriol.* 175:2943–2951] suggests an evolutionary importance of having two or more catalytic domains in one enzyme. XynZ contains a contains a family VI CBD, which does not bind cellulose significantly. However, representatives of CBDs of this family usually efficiently bind xylan. The CBD of XynZ may participate in a tight association of the catalytic domains with the substrate. This is consistent with the higher Km of FAE as compared to that of XynZ FAE/CBD.

Both FAE/CBD and FAE are highly thermostable. They are active against both feruloyl and p-coumaroyl esterified substrates, and they represent the first FAE from bacteria to hydrolyze p-coumaroyl esters. The high Km of FAE versus XynZ FAE/CBD indicates that the CBD is important in binding the substrate before enzyme catalysis.

The FAE domains of XynZ and XynY are homologous to each other and to the Orpinomyces FaeA. The Orpinomyces FaeA, together with those homologous sequences, however, failed to show significant homology to the recently published feruloyl esterases (FaeA) of *Aspergillus niger* and *A. tubingensis* [de Vries et al. (1997) supra] as well as CinA and CinB from *Butyrivibrio fibrisolvens* [Dalrymple et al. (1996) *FEMS Microbiol. Lett.* 143:115–120; Dalrymple and Swadling (1997) *Microbiology* 143:1203–1210] and XylD from *Pseudomonas fluorescens* subsp. *cellulosa* [Ferreira et al. (1993) *Biochemical Journal* 294:349–355]. The sequence analysis implies that a new type of feruloyl esterase is encoded by the Orpinomyces gene and the homologous *C. thermocellum* sequences described above. The Orpinomyces FaeA, and the FAE domains of XynZ and XynY were also shown to be homologous to a hypothetical polypeptide of *E. coli* (Genbank Accession Number P31471) and the carboxy terminal region of a Ruminococcus sp. xylanase earlier designated as a UD [Genbank Accession Number S58235]. No function had been assigned to those sequences of *E. coli* and Ruminococcus. Without wishing to be bound by theory, the present inventors believe that these sequences also encode feruloyl esterases and that the *Ruminococcus xylanase* is also bifunctional. Ruminococcus has been shown to produce FAE activity [McSweeney et al. (1998) *Anaerobe* 4:57–65], and another *Ruminococcus xylanase* has been shown to be a bifunctional enzyme with xylanase and acetyl xylan esterase activity [Kirby et al. (1998) *Biochemical Society Transactions* 26:S169]. No feruloyl esterase activity has been observed in *E. coli*. The gene from *E. coli* may encode a dipeptidase instead, because homology exists between a dipeptidase from *Aspergillus fumigatus* and feruloyl esterases. The data suggest a common ancestral gene encoding feruloyl esterases from Orpinomyces, *C. thermocellum*, and Ruminococcus.

Applications for the phenolic acid esterase enzymes of the present invention, especially the feruloyl esterases, include producing ferulic acid from wheat bran or agricultural byproducts, using the enzyme to treat grasses, grains or other plant materials which are used in the pulp and paper industry, feed processing, and as a food additive. These thermostable enzymes have advantages over other enzymes because they are easy to purify, have high temperature optima and are stable over a wide pH range.

Any of the feruloyl esterases as described (see also U.S. patent application Ser. No. 09/390,224, filed Sep. 3, 1999, incorporated by reference herein) can be used as food or feed supplements. Other phenolic acid or feruloyl esterases known to the art can also be used in the methods and compositions of the present invention. For example, esterases isolated after production from a naturally occurring microbial strain or through recombinant production using nucleic acids ultimately derived from a naturally occurring strain are contemplated. Naturally occurring microbes which produce phenolic acid esterases and/or feruloyl esterases include, without limitation, strains of Aureobasidium, Trichoderma, Aspergillus, Bacillus, Streptomyces, Penicillium, Neocallimastix, and Humicola, as well known in the art.

Xylanases are also available from a variety of sources including but not limited to, Orpinomyces PC-2, *Aureobasidium pullulans*, Neocallimastix, Clostridium, Bacillus, Streptomyces, Thermotoga, Talaromyces, Caldocellum, Thermonospora, ruminent bacteria and fungi, among many others well known to the art.

When a grain or other plant-derived food or feed component having a substantial non-starch polysaccharide content is used, the energy source availability can be increased by treatment with a feruloyl esterase and a xylanase at a ration of 1 to 200 U/kg for each enzyme, desirably about 10 to about 50 U/kg feed or food. As shown in Table 12, there appears to be a synergism between xylanase and feruloyl esterase.

Food or feed can be supplemented or treated with the feruloyl esterase and xylanase to improve nutrition and energy source availability for humans, poultry (e.g., chickens, turkeys, ducks, geese, and other fowl), swine, sheep, cattle, horse, goats, fish (including but not limited to salmon, catfish, tilapia and trout) and shellfish, especially shrimp, and other farmed animals.

Food or feed ingredients which are improved by treatment with feruloyl esterase and xylanase include, without limitation, wheat, rye, barley, oats, corn, rice, soybean, millet, sorghum, grasses, legumes and other pasture and forage plants. Fresh or dry feed or food components can be treated with a liquid comprising the xylanase and phenolic acid esterase so that the particles of the food or feed are coated with the enzymes. Similarly, wet or dry enzyme compositions can be added to a liquid food or feed composition so that the ratio of enzymes to dry weight or plant material is as taught herein.

The present inventors have demonstrated the usefulness of feruloyl esterase as an animal feed additive, as described in Example 7 below. Wheat represents a potential energy source in poultry and swine or other rations, for example, but it is frequently avoided because of its low energy value relative to corn. The lower energy availability is due to the presence of a significant amount of non-digestible fiber or non-starch polysaccharide (NSP). In addition to NSP being unavailable for energy, it also acts as an anti-nutritional factor and reduces digestibility of other components of the diet. The availability of fiber-degrading enzymes that can be added to wheat diets has increased interest in the use of wheat and other grains for poultry and swine rations. Three day old broiler chicks were fed an energy-deficient diet or the same diet supplemented with Orpinomyces or other feruloyl esterase protein, a xylanase A (for example from Orpinomyces or from *Aureobasidium pullulans* for example [see U.S. Pat. No. 5,591,619, Li et al., 1997]) or a combination of these enzymes. See Table 11 for composition of the basal diet and Example 7. The results of this feeding experiment are summarized in Table 12. Weight gain and feed efficiency in the control group is set to 100. Feruloyl esterase alone did not significantly affect weight gain. Birds grew slightly slower (97% of control) and required slightly more feed per unit of gain than the control, unsupplemented group. Xylanase alone improved growth rate 7% and feed efficiency 5%. The combination of xylanase and feruloyl esterase showed the greatest response, with a 15% improvement in growth rate and a 10% improvement in efficiency over that in the control group.

Besides promoting increased nutrient availability, feruloyl esterase can be used to improve the ferulic acid availability in a food or feed. Ferulic acid has antioxidant activity, and it can be made available through feruloyl esterase treatment of a foodstuff. Ferulic acid is an antioxidant, and accordingly, there is interest in its use to promote general health, to act as an anti-tumor agent and as an anti-aging agent. For example, wheat can be treated with feruloyl esterase, advantageously in combination with xylanase, and be consumed to serve as a ferulic acid supplement, especially in humans. Its consumption then improves the oxidant/antioxidant status and the general health of the consumer.

In addition to plant-derived solid food or feed treated with feruloyl esterase or the combination of feruloyl esterase and xylanase, liquids (beverages, e.g.) can also comprise feruloyl esterase (or feruloyl esterase and xylanase) treated material or soluble products thereof. If the beverage contains the solid foodstuff or feedstuff, enzymes(s) is(are) added at a ratio of from about 1 to 200 units of enzyme per kg, desirably from about 10 to about 50 U/kg of esterase and for xylanase, from about 100 to about 10,000 U/kg dry weight of plant-derived material in the liquid foodstuff or beverage.

A feruloyl esterase described herein, desirably in combination with a cellulase and/or xylanase, for example that from Orpinomyces PC-2, can also be used in the pulping and paper recycling industries. The ratio of the esterase to solids is from about 0.1 to about 200 U/kg dry weight, desirably from about 1 to about 100 U/kg, and advantageously from about 10 to about 50 U/kg.

The feruloyl esterase or combination of feruloyl esterase and xylanase can be formulated as dry materials or as liquid concentrates for subsequent use in combination with a source of plant-derived non-starch polysaccharide or poorly digestible plant fiber material to be treated. Such a formulation can be freeze-dried in the case of a dry material or it can be a liquid concentrate. A liquid formulation can contain from about 100 ug. to about 50 mg/ml of protein. Reducing agents such as cystine dithiothreitol, dethioerythritol or β-mercaptoethanol can be included to prevent enzyme oxidation, and protein stabilizing agents, for example glycerol (0.1% to 10% w/v), sucrose (0.1% to 10% w/v) among others, can be included, or an irrelevant protein such as bovine serum albumin or gelatin, can also be present.

Although the esterases of the present invention are stable, a buffering agent can be added to stabilized the pH in the range of about 4.5 to 7.8.

The feruloyl esterase domain of XynZ was highly expressed in *E. coli* and the esterase comprised 40–50% of the total cell protein. The recombinant esterase of XynZ was purified to almost homogeneity by heat treatment. The protein had a molecular mass of 45 kDa, consistent with the size of the predicted deduced amino acid sequence. Of the substrates tested, the expressed protein had high specific activity towards FAXX and $FAX_3$. With $FAX_3$ as a substrate Km and Vmax values were 3.2 mM and 13.5 $\mu$mol ferulic acid released min-1 mg-1 respectively at pH 6.0 at 60° C. Several phenolic esterified substrates were hydrolyzed and the specific activities with those containing feruloyl groups were higher than were those with p-coumaroyl groups confirming that the previously unknown domain of XynZ is a feruloyl esterase. The enzyme released mainly ferulic acid from wheat bran and Coastal Bermuda grass (CBG) with a smaller amount of p-coumaroyl groups released from CBG. This study represents the first demonstration of esterases in the cellulosome of *Clostridium thermocellum* and of enzymes from the cellulosome with two different activities. The present work also provides a phenolic acid esterase derived from a xylanase from Ruminococcus and as an enzyme produced by Orpinomyces PC-2.

Figure 7:
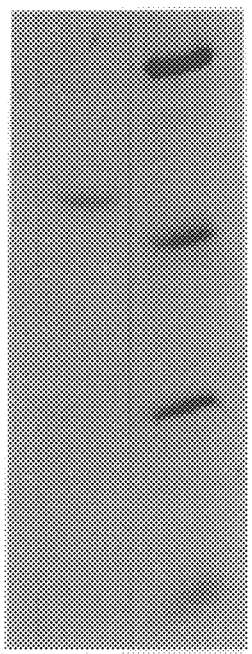
FIG. 7 illustrates the results of SDS-PAGE analysis of the purified feruloyl esterase from the culture supernatant of Orpinomyces sp. strain PC-2 (lane 1); molecular mass markers are in lane 2.

A summary of the purification of FAE from Orpinomyces sp stain PC-2 is presented in Table 7. The Q-Sepharose column separated two peaks of esterase activity. Proteins which eluted in the first peak had higher activity against ethyl-pCA while proteins eluting in the second peak had greater activity against FAXX. These data suggest that a p-coumaroyl esterase eluted in the first peak while the feruloyl esterase eluted in the second. The first peak was not studied further, but the fractions in peak 2 were further purified resulting in a purified enzyme which had an approximate molecular mass of 50 kDa as visualized by SDS-PAGE analysis (FIG. 7). There was a decrease in specific activity after the MonoQ step which could not be explained.

Figure 8A:
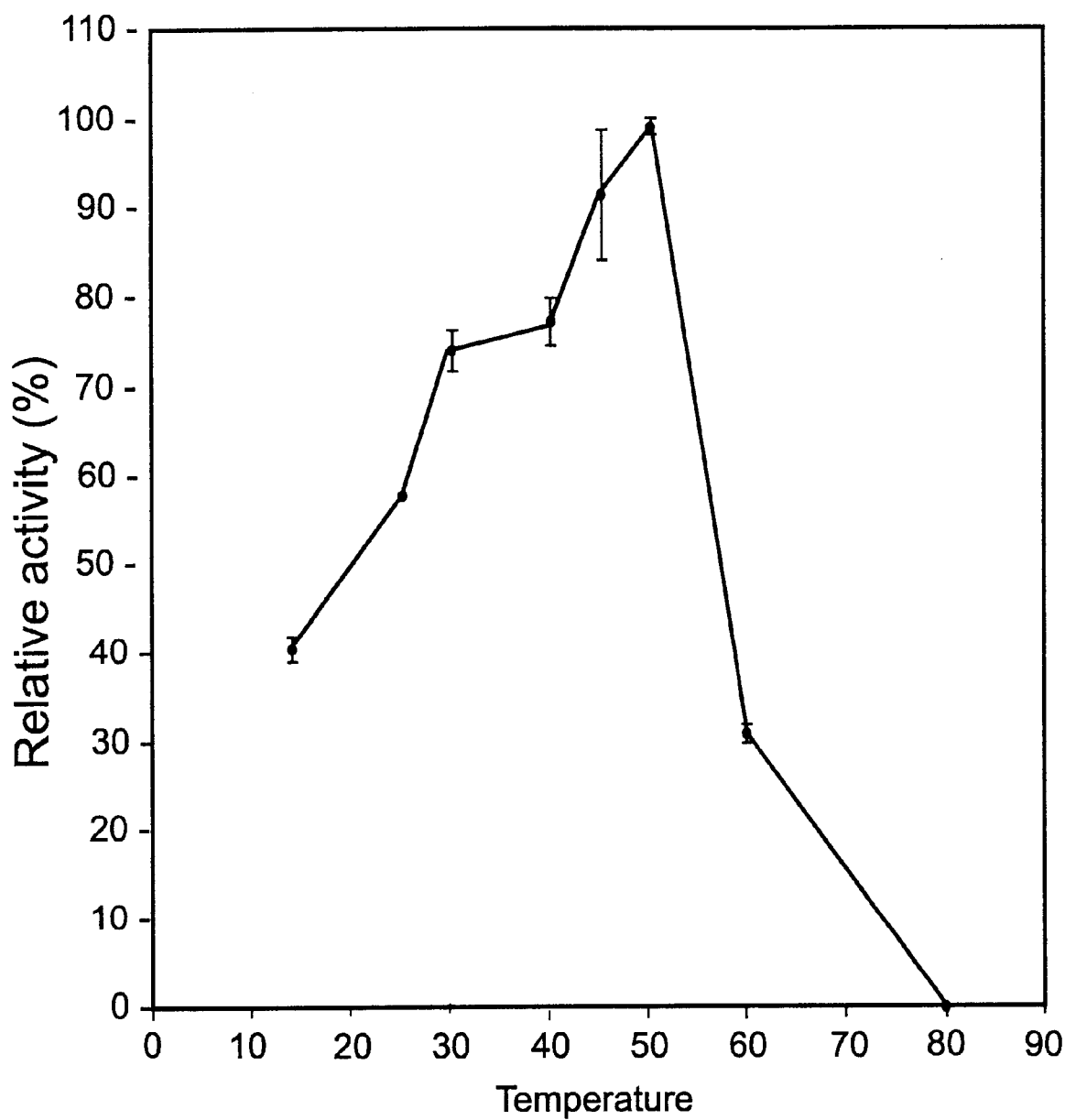
FIGS. 8A and 8B show the temperature and pH activity profiles, respectively, of the Orpinomyces sp. strain PC-2 feruloyl esterase.
Figure 8B:
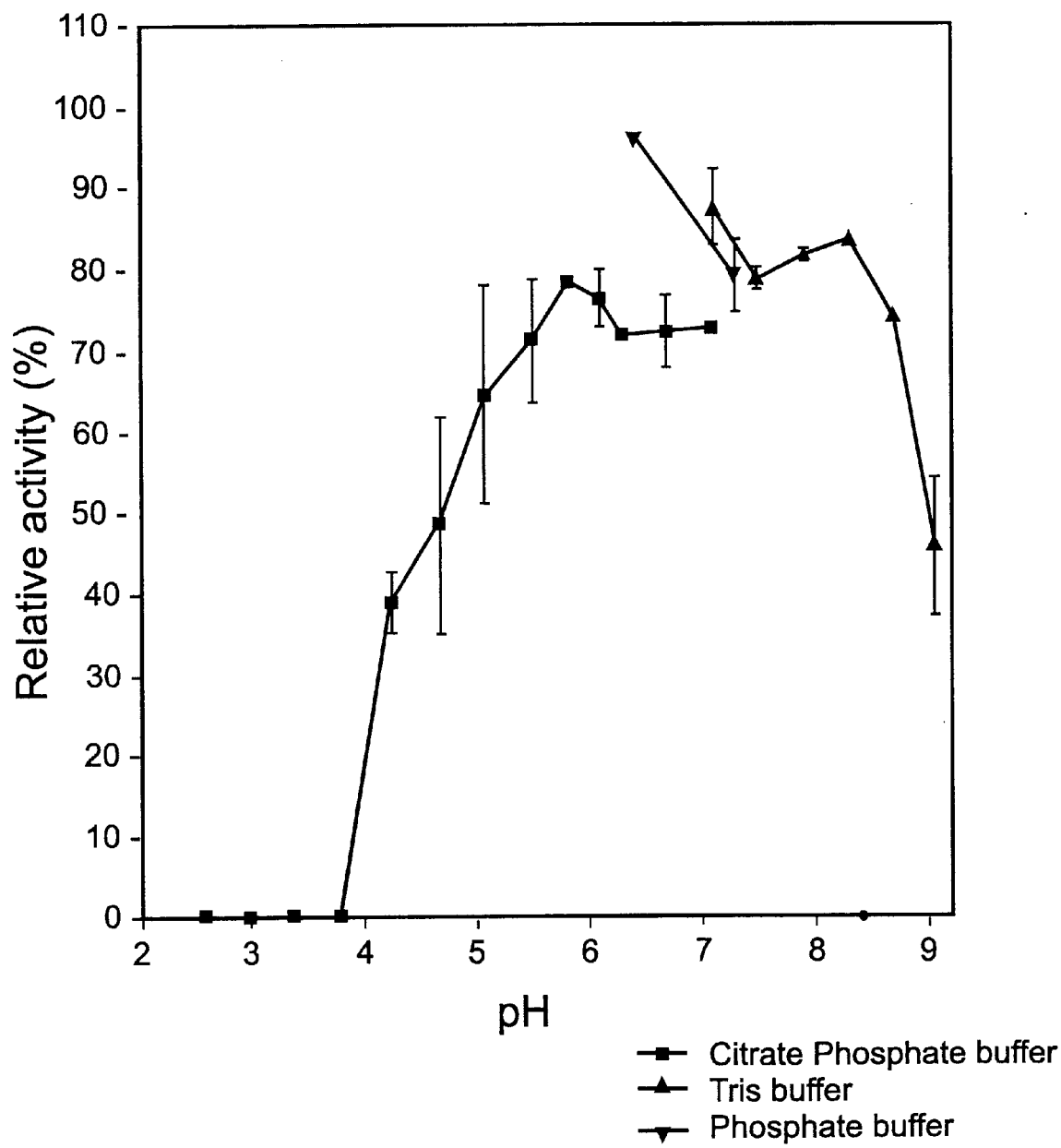
Figure 10:
FIG. 10 is a schematic diagram of the faeA gene from Orpinomyces PC-2.
Figure 10:
Figure 10:
Figure 10:
Figure 11:
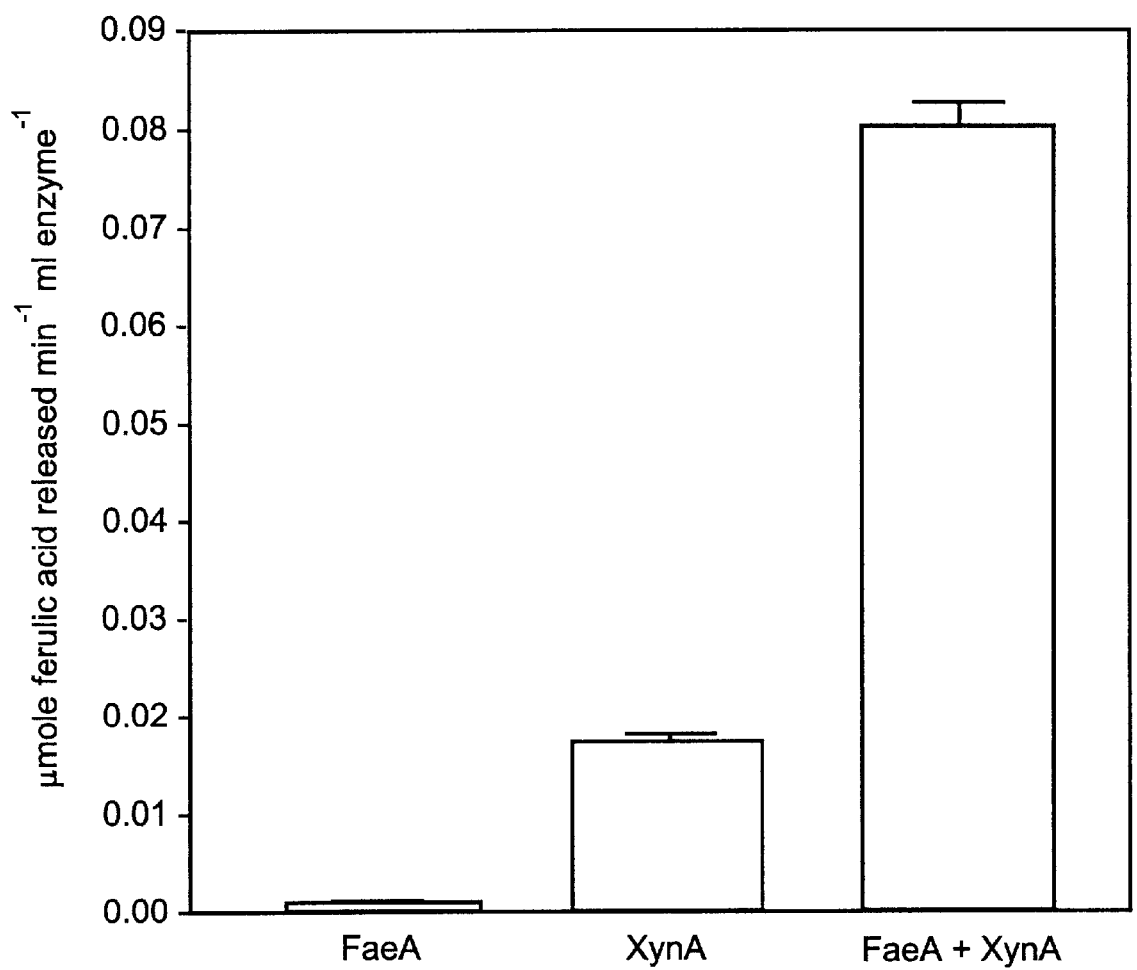
FIG. 11 illustrates the synergistic effects of the Orpinomyces FaeA and XynA on the release of ferulic acid from wheat bran as substrate.

Temperature and pH optima experiments showed that the enzyme had a temperature optimum of 50° C. (FIG. 8A) and had activity over a pH range between 5.2 and 8 (FIG. 8B). The purified enzyme was stable at 4° C. for over 18 months. The purified enzyme was subjected to N-terminal sequencing giving the sequence ETTYGITLRDTKEKFTVFKD (SEQ ID NO:21). The protein was also subjected to internal sequencing which resulted in four peptide fragments (Table 8) which were used to create degenerate PCR primers.

Two of the peptide fragments from the internal amino acid sequencing were used to create degenerative olignucleotide primers which are listed in the materials and methods section. These primers were used to amplify regions of DNA in the Orpinomyces PC-2 cDNA library. A 216 bp PCR product was generated. The PCR product was labeled with digoxygenin-UTP and used as a probe to screen the cDNA library. After screening 50,000 phage, one positive plaque was obtained and its DNA was sequenced using T3 and T7 universal primers. Sequencing using the T3 primer did not reveal any ORFs, however, sequencing using the T7 reverse primer gave the C-terminal end of the gene. Based on the sequence data and restriction fragment analyses, but without wishing to be bound by theory, we have concluded that the faeA gene in this cDNA was truncated and furthermore that the insert comprises multiple genes. These other genes were not studied further. The deduced amino acid sequence of the insert matched the data from the peptide sequencing. The insert had a size of 1074 bp and encoded a protein of 358 amino acids. Since the size of the encoded protein did not match that of the purified enzyme and the N-terminal sequence, including a signal peptide and lack of a start codon, another round of screening was performed using the entire sequence as a probe after digoxygenin labeling. After screening an additional 50,000 phage, one positive clone was obtained which had a size of 1673 bp with the largest open reading frame comprising a protein of 530 amino acids. The sequence of this insert is believed to be an incomplete one since no 5' UTR was found and the (putative) signal sequence has only four amino acids. Most signal sequences found in hydrolytic enzymes from anaerobic fungi are at least 20 amino acids long. The insert was found to be in a reverse orientation with respect to the lacZ promoter. The upstream lac promoter should direct synthesis of the inserted gene, but no activity was found in lysed *E. coli* cells harboring the recombinant plasmid. The faeA gene in *E. coli* was expressed using the pET system (Novagen) in the correct orientation. The recombinant FaeA released ferulic acid from FAXX as well as other substrates which were esterified with phenolic groups. The enzyme had the highest activity against FAXX, which demonstrates that it is a true feruloyl esterase (Table 10). In addition, when the enzyme was incubated with a recombinant xylanase, there was a 80 fold increase in FA released over FaeA alone.

Figure 9:
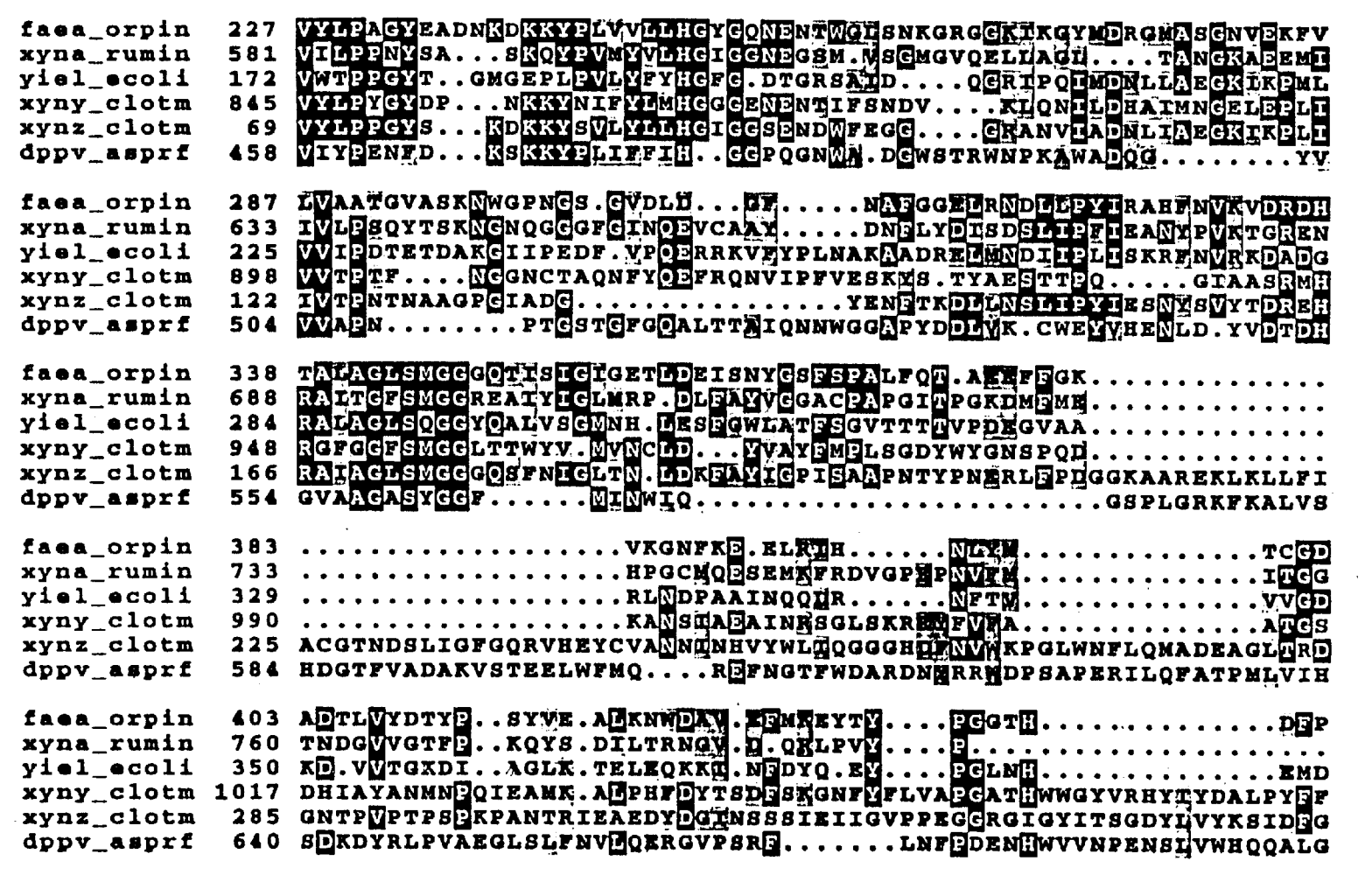

The nucleotide and deduced amino acid sequence of the faeA gene are shown in Table 9. A BLAST analysis of the encoded protein showed homology to several enzymes. These enzymes included domains of unknown function from Xylanase Z and Xylanase Y of *Clostridium thermocellum*, a domain of unknown function in a xylanase from Ruminococcus spp. and a 44 kDa hypothetical protein from *E. coli*, and a dipeptidyl peptidase from *Aspergillus fumigatus* (FIG. 9). All proteins had at least 20% identity with the C-termninal 300 amino acids of the protein. The N-terminal part of the enzyme did not show homology to any enzyme in the 3 BLAST analysis and the function of this domain is unknown. Although FAE activity has been demonstrated in the cellulase/hemicellulase complex from Orpinomyces, this protein does not contain a non-catalytic repeated peptide domain (NCRPD). Analysis of C-terminal coding region indicated a typical signature sequence found in lipases and other esterases of GXSXG at residues 341–345 as well as an aspartic acid at residue 403 and a histidine at residue 436 which would make up the catalytic triad. A search of the sequence revealed two N-glycosylation sites at amino acids 300 and 488 (of SEQ ID NO:18) and a 16mer poly A tail in the 3' UTR.

It will be understood by those skilled in the art that other nucleic acid sequences besides those disclosed herein for the phenolic acid esterases, i.e. feruloyl esterases, will fiction as coding sequences synonymous with the exemplified coding sequences. Nucleic acid sequences are synonymous if the amino acid sequences encoded by those nucleic acid sequences are the same. The degeneracy of the genetic code is well known to the art. For many amino acids, there is more than one nucleotide triplet which serves as the codon for a particular amino acid, and one of ordinary skill in the art understands nucleotide or codon substitutions which do not affect the amino acid(s) encoded. It is further understood in the art that codon substitutions to conform to common codon usage in a particular recombinant host cell is sometimes desirable.

Specifically included in this invention are sequences from other strains of Clostridium and from other microorganisms which hybridize to the sequences disclosed for feruloyl and coumaryl esterases under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences, (indicating about 95–100% nucleotide sequence identity). Also specifically included in this invention are sequences from other strains of Orpinomyces species and other anaerobic fungi which hybridize to the sequences disclosed for the esterase sequences under moderately stringent conditions. Moderately stringent conditions refer to conditions understood in the art for a given probe sequence and "conditions of medium stringency" means hybridization and wash conditions of 50°–65° C., 1×SSC and 0.1% SDS (indicating about 80–95% similarity). Also specifically included in this invention are sequences from other strains of Orpinomyces, from other anaerobic fungi, and from other organisms, including bacteria, which hybridize to the sequences disclosed for the esterase sequences under highly stringent conditions. Highly stringent conditions refer to conditions understood in the art for a given probe sequence and "conditions of high stringency" means hybridization and wash conditions of 65°–68° C., 0.1×SSC and 0.1% SDS (indicating about 95–100% similarity). Hybridization assays and conditions are further described in Sambrook et al. (1989).

A method for identifying other nucleic acids encoding feruloyl esterase- and/or coumaryl esterase-homologous enzymes is also provided wherein nucleic acid molecules encoding phenolic acid esterases are isolated from an anaerobic fungus, including but not limited to Orpinomyces or an anaerobic bacterium, such as Clostridium or Ruminococcus, among others, and nucleic acid hybridization is performed with the nucleic acid molecules and a labeled probe having a nucleotide sequence that includes all or part of a FAE coding sequence as given in Table 5, 6, 9 and/or 10 herein. By this method, phenolic acid esterase genes similar to the exemplified feruloyl and coumaryl esterases can be identified and isolated from other strains of Clostridium or other anaerobic microorganisms. All or part of a nucleotide sequence refers specifically to all continuous nucleotides of a nucleotide sequence, or e.g. 1000 continuous nucleotides, 500 continuous nucleotides, 100 continuous nucleotides, 25 continuous nucleotides, and 15 continuous nucleotides.

Sequences included in this invention are those amino acid sequences which are 40 to 100% identical to the amino acid sequences encoded by the exemplified *C. thermocellum* strain feruloyl esterase, amino acids proteins truncated from the XynY or XynZ proteins or the Ruminococcus FAE polypeptide or the Orpinomyces PC-2 FAE polypeptide, all specifically identified herein. Sequences included in this invention are also those amino acid sequences which are 40, 50, 60, 70, 75, 80, 85, 90, 95 to 100%, and all integers between 40% and 100%, identical to the amino acid sequences encoded by an exemplified phenolic acid esterase coding sequence and corresponding to or identifying encoded proteins which exhibit feruloyl esterase activity. In comparisons of protein or nucleic acid sequences, gaps introduced into either query or reference sequence to optimize alignment are treated as mismatches. In amino acid sequence comparisons to identify feruloyl esterase proteins, the reference sequence is, desirably, amino acids 227 to 440 of SEQ ID NO:18 (FAE of Orpinomyces PC-2).

It is well-known in the biological arts that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978) in *Atlas of protein Sequence and Structure*, Volume 5, Supplement 3, Chapter 22, pp. 345–352, which is incorporated by reference herein provides frequency tables for amino acid substitutions which can be employed as a measure of amino acid similarity. Dayhoff et al.'s frequency tables are based on comparisons of amino acid sequences for proteins having the same fraction from a variety of evolutionarily different sources.

Techniques and agents for introducing and selecting for the presence of heterologous DNA in plant cells and/or tissue are well-known. Genetic markers allowing for the selection of heterologous DNA in plant cells are well-known, e.g., genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al., *Methods for Plant Molecular Biology*, A. Weissbach and H. Weissbach, Eds., Academic Press, Inc., San Diego, Calif. (1988).

Techniques for genetically engineering plant cells and/or tissue with an expression cassette comprising an inducible promoter or chimeric promoter fused to a heterologous coding sequence and a transcription termination sequence are to be introduced into the plant cell or tissue by Agrobacterium-mediated transformation, electroporation, microinjection, particle bombardment or other techniques known to the art. The expression cassette advantageously further contains a marker allowing selection of the heterologous DNA in the plant cell, e.g., a gene carrying resistance to an antibiotic such as kanamycin, hygromycin, gentamicin, or bleomycin. Assays for phenolic acid esterase and/or xylanase enzyme production are taught herein or in U.S. Pat. No. 5,824,533, for example, and other assays are available to the art.

A DNA construct carrying a plant-expressible gene or other DNA of interest can be inserted into the genome of a plant by any suitable method. Such methods may involve, for example, the use of liposomes, electroporation, diffusion, particle bombardment, microinjection, gene gun, chemicals that increase free DNA uptake, e.g., calcium phosphate coprecipitation, viral vectors, and other techniques practiced in the art. Suitable plant transformation vectors include those derived from a Ti plasmid of *Agrobacterium tumefaciens*, such as those disclosed by Herrera-Estrella (1983), Bevan (1983), Klee (1985) and EPO publication 120,516 (Schilperoort et al.). Inaddition to plant transformation vectors derived from the Ti or root-inducing (Ri) plasmids of Agrobacterium, alternative methods can be used to insert the DNA constructs of this invention into plant cells.

The choice of vector in which the DNA of interest is operatively linked depends directly, as is well known in the art, on the functional properties desired, e.g., replication, protein expression, and the host cell to be transformed, these being limitations inherent in the art of constructing recombinant DNA molecules. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector of the present invention may also be a Lambda phage vector including those Lambda vectors described in *Molecular Cloning: A Laboratory Manual, Second Edition*, Maniatis et al., Eds., Cold Spring Harbor Press (1989) and the Lambda ZAP vectors available from Stratagene (La Jolla, Calif.). Other exemplary vectors include pCMU [Nilsson et al. (1989) *Cell* 58:707]. Other appropriate vectors may also be synthesized, according to known methods; for example, vectors pCMU/K$^b$ and pCMUII used in various applications herein are modifications of pCMUIV (Nilson et al., supra).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens* described by Rogers et al. (1987) *Meth. in Enzymol.* 153:253–277, and several other expression vector systems known to fraction in plants. See for example, Verma et al., No. WO87/0055 1; Cocking and Davey (1987) *Science* 236:1259–1262.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (See Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol Biol.* 42:205; Gasser and Fraley (1989) *Science* 244:1293; Leemans (1993) *Bio/Technology.* 11:522; Beck et al. (1993) *Bio/Technology.* 11:1524; Koziel et al. (1993) *Bio/Technology.* 11:194; and Vasil et al. (1993) *Bio/Technology.* 11:1533.). Techniques are well-known to the art for the introduction of DNA into monocots as well as dicots, as are the techniques for culturing such plant tissues and regenerating those tissues.

Many of the procedures useful for practicing the present invention, whether or not described herein in detail, are well known to those skilled in the art of plant molecular biology. Standard techniques for cloning, DNA isolation, amplification and purification, for enzymatic reactions involving DNA ligase, DNA polymerase, restriction endonucleases and the like, and various separation techniques are those known and commonly employed by those skilled in the art.

Monoclonal or polyclonal antibodies, preferably monoclonal, specifically reacting with the phenolic acid esterases of the present invention may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (Eds.) (1983) *Meth. Enzymol.* 100 and 101; Grossman and Moldave (Eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles, of Gene Manipulation*, University of California Press, Berkeley; Schleif and Wensink (1982) *Practical Methods in Molecular Biology*; Glover (ed.) (1985) DNA Cloning Vol. I and II, IRL Press, Oxford, UK; Hames and Higgins (Eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

Each reference and patent document cited in the present application is incorporated by reference herein to the extent that it is not inconsistent with the present disclosure.

The following examples are provided for illustrative purposes, and is not intended to limit the scope of the invention as claimed herein. Any variations in the exemplified articles which occur to the skilled artisan are intended to fall within the scope of the present invention.

EXAMPLES

Example 1

Bacterial Strains, Vectors, and Culture Media

*C. thermocellum* JW20 was cultivated in prereduced liquid medium [Wiegel and Dykstra (1984) *Appl. Microbiol. Biotechnol.* 20:59–65] at 60° C. under an atmosphere of nitrogen. Avicel (microcrystalline cellulose, 0.4% w/v, Baker TLC, 2–20 micron particle size) was used as the carbon source. *E. coli* strain BL21 (DE3) (Stratagene, La Jolla, Calif.) and plasmid pRSET B (Invitrogen, Carlsbad, Calif.) were used the host strain and the vector for protein expression. Improved results were obtained using plasmid pET-21 b (Novagen, Madison, Wiss.). The recombinant *E. coli* were selected for by growing in LuriaBertani medium containing 100 µg/ml ampicillin.

Example 2

Amplification and Cloning of Sequences Coding for Different Domains of *C. thermocellum* XynY and XynZ Genomic DNA was isolated from *C. thermocellum* as previously described [Maniatis et al. (1982) supra]. PCR primers were designed (Table 1) and synthesized on an Applied Biosystems (Foster City, Calif.) DNA sequencer. To facilitate the insertion of DNA sequence into or pET-21 b or pRSET B, BamHI (for pET-216) or NdeI for pRSET B, and HihdIII sites were added to forward and reverse primers, respectively (Table 1). PCRs were carried out on a Perkin Elmer 480 Thermocycler for 30 cycles with each cycle on 95° C. for 1 min, 48° C. for 1 min, and 72° C. for 3 min. PCR products and the plasmid were digested with BamHI (or NdeI) and HindIII, purified with a Bio101 Geneclean kit, ligated with T4 ligase. *E. coli* BL21(DE3) was transformed with the ligation mixture and at least four colonies of each construct were picked for analyzing feruloyl esterase expression. The inserted sequences were sequenced to verify the lack of unwanted mutations.

Two internal sequences were used to create degenerate oligonucleotide primers for PCR in order to amplify the feruloyl esterase coding sequence in the cDNA library in Orpinomyces. The Orpinomyces PC-2 cDNA library is described in the λZAPII vector (Stratagene, La Jolla, Calif.) in *E. coli* host cells is described in Chen et al. (1995) *Proc. Natl. Acad. Sci.* 92:2587–2591. Positive clone(s) are subclonal into a pBluescript vector (Stratagene, La Jolla, Calif.). The amplified product was cloned into pCRII (Invitrogen, Carlsbad, Calif.) using the TA cloning kit and sequenced using an automatic PCR sequencer (Applied Biosystems, Foster City, Calif.) using M13 reverse primer. The resulting PCR product was used to screen the cDNA library after being labeled with digoxigenin (Boehringer Mannheim, Indianapolis, Ind.). The digoxigenin probe was bound to plaques which were lifted from a nitrocellulose blot. Antibodies conjugated to alkaline phosphatase showed a single positive clone which hybridized to the PCR product. The product was sequenced and found to contain the C-terminal 358 amino acids of the enzyme (See Table 9). A second probe which incorporated those 339 amino acids was used as a probe to screen the library in the same manner as before. A second clone was isolated which contained the C-terminal region plus an additional 172 amino acids making a polypeptide of 530 amino acids. Confirmation of the sequence came from N-termninal and internal protein sequence data from the purified enzyme which matched that of the cloned cDNA product. Expression cloning of this coding sequence, which lacks an ATG translation start site, can be achieved by expressing it, in frame, as a fusion protein using any one of a number of fusion protein vectors known to the art or an ATG translation start codon and/or ribosome binding site upstream of the ATG can be added using methodology well known to and readily accessible to the art in an expression vector appropriate to the choice of recombinant host cell.

Example 3

Isolation and Analysis of the Cellulosome

The cellulosomes were isolated from 10L of culture fluid after complete substrate exhaustion by the affinity digestion method [Morag et al. (1992) supra]. This preparation was used directly for gel filtration using a Fast Protein Liquid Chromatography (FPLC) system with a Superose 6 column (Pharmacia, Piscataway, N.J.). Proteins were eluted in 50 mM Tris-HCl, 100 mM NaCl at a flow rate of 0.2 ml/min. Fractions of 0.5 ml were collected and stored at 4° C. for further analysis. Cell extracts were prepared by first growing the organism in the presence of 0.2% cellobiose for 2 days. Cells were then separated by centrifugation, resuspended in 50 mM Tris-HCl buffer, pH 7.5, and sonicated. Culture medium was concentrated to 5 ml using a Millipore concentrator (Millipore, Bedford, Mass.). To adsorb cellulosomes from the medium, 0.5 mg of Avicel was added and the suspension was stirred at 4° C. for 4 hours. Avicel was removed by centrifugation (Avicel-treated medium). All fractions were tested for. Avicelase, xylanase, and ferulic acid esterase activities.

Unless otherwise noted, all *C. thermocellum* enzyme assays were performed at 60° C. in 50 mM Na-citrate buffer, pH 6.0. One unit of enzyme activity was defined as the amount of enzyme that released 1 μmol of product min-1, and specific activity is given in units per milligram of protein. Feruloyl esterase activity was measured using a modified version of the assay described by Borneman et al. [Borneman etal. (1990) Anal. Biochem. 190:129–133]. The appropriately diluted protein sample (25 1) was added to 400 μl of buffer plus 8 mM of substrate. Samples were incubated at 60° C. for 5 min. and the reaction was stopped by adding 25 μl of 20% formic acid. Release of ferulic acid was measured via HPLC using a mobile phase of 10 mM Na-formate pH 3 and 30% (vol/vol) methanol. For routine assays, FAXX and FAX3 purified from wheat bran were used as substrates [Borneman et al. (1990) supra]. Ethylferulate and ethyl-p-coumarate esters were a gift from D. E. Akin (USDA, Athens, Ga.). The hydrolysis of these (10 mM) were determined similarly to that of FAXX, but the HPLC analyses were performed with 50% methanol. HPLC runs were with a Hewlett Packard 1100 Series instrument equipped with an autosampler and diode array detector. Ferulic acid and p-coumaric acid were used as standards. To determine the amount of feruloyl and p-coumaroyl groups released from plant cell walls, wheat bran and Coastal Bermuda grass were ground in a Wiley mill to pass through a 250 μm screen. Plant samples of ten milligram were incubated for one hour in 400 μl of 50 mM Na-citrate buffer pH, 6.0 plus 25 μl of enzyme. After the addition of 25 μl of 20% formic acid to stop the reaction, the samples were centrifuged at 16,000×g in a microfuge and then assayed for FA and pCA by HPLC.

Assays with p-nitrophenol substrates were performed in microtiter plate wells. Two hundred microliter of substrate at a concentration of 100 μM was preincubated in wells heated to 40C. Enzyme (10 μl) was added to the reaction mixture and the absorbance was followed continuously at a wavelength of 405 nm. p-Nitrophenol was used as standard. Xylanase and Avicelase activities were measured by reducing sugar assays using dinitrosalicylate. [Miller, G. L. (1959) *Anal. Chem.* 31:127–132].

Unless otherwise noted, all *Orpinomyces enzyme* assays were performed at 40° C. in 50 mM Bis-Tris Propane buffer, pH 6.0. One unit of enzyme activity is defined as the amount that released 1 μmol of product min-1, and specific activity is given in units per milligram of protein. Protein was determined by the method of Bradford [Bradford, M. (1976) *Anal. Biochem.* 72:248–254]. Feruloyl esterase activity was assayed by the method of Bomeman et al. [(1990) supra] which involved measuring the release of ferulic acid from FAXX via HPLC using a mobile phase of 10 mM Na-formate pH 3 and 30% (vol/vol) methanol. FAXX was purified from wheat bran as previously described [Bomeman et al. (1990) supra]. For assay usingethyl-p-coumarate (ethyl-pCA), the substrate (10 mM) was used with 30% methanol in the same mobile phase. Samples were run on a Hewlett Packard 1100 Series instrument equipped with an autosampler and diode array detector. Ferulic acid and p-coumaric acid were used as standards. The appropriately diluted protein sample (25 μl) was added to 400 μl of buffer containing 750 μM FAXX. Samples were incubated at 40° C. for 30 min. and the reaction was stopped by adding 25 μl of 20% formic acid. pH optimum assays were carried out in 100 mM citrate phosphate buffer in the range of 2.6–7.0, 100 mM phosphate in the range of pH 5.7–6.3, and 100 mM Tris in the range of pH 7.0–9.0. For temperature optimum determination, purified esterase were incubated for 30 minutes at the appropriate temperature within the range of 200 to 70° C.

All reactions to test the specificity of the Orpinomyces PC-2 enzyme were carried out in 50 mM citrate buffer pH 6.0. FAXX, FAX3,Et-FA and Et-pCA were assayed for 5 min. at 40° C. at a concentration of 10 mM. Enzyme solution (L) was added 400 μl of substrate solution. The reaction was stopped with 25 μl of 20% formate. For studies on wheat bran, crude recombinant FaeA (50 μl) equaling 0.7 units of activity against FAXX, XynA (50 μl) equaling 300 units of activity against birchwood xylan or both was added to a total reaction volume of 1 ml also containing 10 mg of destarched wheat bran. The reaction was carried out for 40 min at 40° C. and stopped by adding 50 μl of 20% formate.

Example 4

Enzyme Purification

One liter of recombinant *E. coli* expressing the *C. thermocellum* XynZ-derived FAE was grown in Luria broth containing 100 μg/ml ampicillin until $OD_{600}$=0.5 and then grown an additional 4–6 hours. Cells were harvested by centrifugation, resuspended at a concentration of 1 g per 3 ml in 50 mM Tris-HCl (pH 7.5) and lysed in a French pressure cell. Cell debris was removed by centrifugation at 100,000×g. The cell extract was heat treated for 30 min. at 70° C. Denatured protein was removed by centrifugation at 100,000×g. The supernatant was run on a MonoQ HR 10/10 ion exchange chromatography column (Pharmacia, Piscataway, N.J.) equilibrated with 50 mM sodium citrate buffer, pH 6.0. MonoQ (Pharmacia, Piscataway, N.J.) is a strong anion exchange resin, hydrophilic and in bead form. A linear gradient of 1 M NaCl in the same buffer over 40 ml was used to elute the purified protein. Proteinsamples were stored at 4° C.

Alternatively, the 100,000×g supernatant after the heat treatment was concentrated to a volume of 2 ml with a Centricon 10 concentrator (Amicon, Millipore, Bedford, Mass.) and then applied to a TSK3000SW column (Tosohaas) which was run with 50 mM Tris pH 7.5 and 5% glycerol as solvent. The purified enzyme was stored at 4° C. in the elution buffer and was stable for at least a month with minimal loss.

A feruloyl esterase was purified from culture supernatant of Orpinomyces sp. strain PC-2 (Barichievicz and Calza medium [Barichievicz and Calza (1990) Appl. Environ. Microbiol. 56:43–48] with 0.2% Avicel as carbon source). The enzyme was obtained from a 60 liter culture of the fungus. The culture was grown under an atmosphere of $CO_2$ for 6 days. The fungal mycelia were removed by filtration through Miracloth (Calbiochem, San Diego, Calif.) The culture supernatant was concentrated 120 fold using a Pellicon system (Millipore, Bedford, Mass.) and a 10 kDa membrane. The concentrate was loaded onto a Q Sepharose (Pharmacia, Piscataway, N.J.) column equilibrated with 20 mM TrisHCl pH 7.5, and proteins were eluted with a gradient of 1 M NaCl in the same buffer. The active fractions were detected by their ability to release ferulic acid from FAXX as measured by HPLC. The active fractions were combined and ammonium sulfate was added to a concentration of 1.7M. The solution was filtered and then loaded onto a Phenyl Sepharose High Performance Chromatography (Pharmacia) column equilibrated with 20 mM TrisHCl pH 7.5 and 1.7 M ammonium sulfate. The protein was eluted by a negative gradient of buffer without ammonium sulfate. Active fractions were concentrated using a Centricon 10 unit (Amicon, Millipore, Bedford, Mass.) and subsequently applied to a TSK 3000SW column (Tosohaas, Montgomeryville, Pa.) which was equilibrated with 20 mM TrisHCl pH 7.5 and 200 mM NaCl. Fractions with activity were combined and loaded directly onto an anion exchange (MonoQ HR 5/5, Pharmacia, Piscataway, N.J.) column equilibrated with 20 mM TrisHCl pH 7.5. The purified enzyme was eluted using a gradient of 0.5 M NaCl. The purification is'summarized in Table 7.

Example 5

Other Analytical Procedures

Enzyme purity was monitored using sodium dodecyl sulfate-polyacrylamide gel electrophoresis (SDS-PAGE) carried out according to the method of Laemmli [Laemmli (1970) *Nature* (London) 227:680–685]. Proteins were stained with Coomassie blue. The isoelectric point of the *C. thermocellum* XynZ-derived FAE protein was determined by running the protein on a precast IEF gel (Serva). Each gel was run at 12 W constant power for 45 min.

Protein concentrations in liquid samples were determined as described by Bradford, M. (1976) [supra].

The purity of the Orpinomyces FAE protein was verified by SDS-PAGE analysis and Coomassie blue staining. The enzyme had a molecular mass of approximately 50 kDa. Purified enzyme was blotted onto a polyvinylidene difluoride (PVDF) membrane and stained according to the manufacturer's instructions. The band corresponding to the purified enzyme was cut out, and the excised band was digested with Protease Lys-C (Boehringer Mannheim, Indianapolis, ind.). Peptides were separated by HPLC using a C8 reverse phase column. The intact protein and its peptides were subjected to N-terminal amino acid sequencing.

For internal sequencing, the enzyme was run on SDS-PAGE and then blotted onto a PVDF membrane which was stained according to the manufacturer's instructions. The band corresponding to the purified enzyme was cut out with a razor blade and digested with Protease Lys-C (Boehringer Mannheim). Peptides were separated on High Performance Liquid Chromatography with a C8 reverse phase column. The intact protein and its peptides were subjected to N-terminal amino acid sequencing using an Applied Biosystems model 477A gas-phase sequencer equipped with an automatic on-line phenylthiohydantoin analyzer.

Example 6

*C. thermocellum* enzyme Stability Experiments

Purified enzyme at a concentration of 13 μg/nMl was placed in a water bath at the appropriate temperature and incubated at intervals of one hour. Enzyme aliquots (25 μl) were removed and assays were performed in triplicate using FAX3 as a substrate as described above. FAE/CBD was tested at temperatures of 500, 600, and 70° C. while FAE was tested at 70°, 80° and 90° C.

Table 5 [taken from Fontes et al. (1995) supra] presents the nucleotide sequence and deduced amino acid sequence (amino acids 808–1061 of XylY) of *C. thermocellum* xylY, which is Xylanase Y. The starting points of the five domains are marked A to #, with arrows. The sequence is available under Accession Number X 83269, EMBL database.

Table 6 [taken from Grepinet et al. (1988) supra] presents the nucleotide and deduced amino acid sequences (amino acids 30–274 of XynZ) of the *C. thermocellum* xynZ and its gene product.

Table 9 presents the deduced amino acid sequence and cDNA coding sequence of the mature phenolic acid esterase of Orpinomyces PC-2.

FIG. 1 provides the amino acid sequence for a phenolic acid esterase (feruloyl esterase) which corresponds to a previously uncharacterized *Ruminococcus xylanase*. The sequence of the complete coding sequence of that xylanase is available under Accession No. 558235 (Genbank database) (See Table 9). The coding sequence of the phenolic acid esterase polypeptide is nucleotide 2164–2895, exclusive of translation start and stop codons.

Catalytically active polypeptides were produced in recombinant *E. coli* after the PCR amplification and cloning as described in Example 2 hereinbelow.

Example 7

Enzymatic Food Supplements

To test whether feruloyl esterase, (FaeZ from *C. thermocellum*), xylanase A from Orpinomyces PC-2 or the combination of the two enzymes improved the availability of nutrients, a feeding experiment was carried out using broiler chicks.

One-day old broiler chicks (Ross male x Arbor Acres female) were obtained locally (ConAgra, Athens, Ga.) and placed in Petersime battery brooders. Birds were housed 8 per pen, and there were 48 pens in each of two studies. Birds had unlimited access to feed and water. After feeding a complete starter ration (University of Georgia starter corn and soybean meal based diet) for 2 days, birds were switched to the experimental diets. The basal experimental diet consisted of 63% ground wheat, 32% soybean meal and vitamins and minerals. The calculated nutrient composition of this diet was: 22% crude protein, 1.22% lysine, 0.92% sulfur amino acids and 2850 kcal/kg. The diet met the National Research Council requirements for all nutrients except energy. The rationale for designing an energy-deficient diet was that exogenous enzyme addition would result in liberation of carbohydrate from the non-starch polysaccharide component of the diet. In two separate studies the effects of xylanase A (U.S. Pat. No. 5,824,533) at either 1000 or 5000 U/kg with and without feruloyl esterase at 5 or 25 U/kg was compared to the basal diet with no enzyme addition. Birds were fed test diets for 14 days.

TABLE 1

Primers used in amplifying various regions of xynY and xynZ of *C. thermocellum*

| Name | Sequence[a] | Gene | Direction | Position[b] | SEQ ID NO: |
|---|---|---|---|---|---|
| XYF1Bam[a1] | TAGGATCCCCTGTAGCAGAAAATCCTTC | xynY | Forward | 795–800 | 1 |
| XYF1[c] | TACATATGCCTGTAGCAGAAAATCCTTC | xynY | Forward | 795–800 | 2 |
| XYR1[c] | GAGGAAGCTTTTACATGGAAGAAATATGGAAG | xynY | Reverse | 1071–1077 | 3 |
| XZF1[d] | TACATATGCTTGTCACAATAAGCAGTACA | xynZ | Forward | 20–26 | 4 |
| XZF1Bam | TAGGATCCCTTGTCACAATAAGCAGTACA | xynZ | Forward | 20–26 | 5 |
| XZR1[d] | GAGGAAGCTTTTAGTTGTTGGCAACGCAATA | xynZ | Reverse | 242–247 | 6 |
| XZR2[d] | GAGGAAGCTTACTTCCACACATTAAAATC | xynZ | Reverse | 261–266 | 7 |
| XZR3[d] | GAGGAAGCTTAGTTTCCATCCCTCGTCAA | xynZ | Reverse | 281–286 | 8 |
| XZR4[d] | GAGGAAGCTTAGTCATAATCTTCCGCTTC | xynZ | Reverse | 302–307 | 9 |
| XZR5[d] | GAGGAAGCTTAAACGCCAAAAGTGAACCAGTC | xynZ | Reverse | 414–421 | 10 |

[a]Restriction sites NdeI and HindIII are underlined and double-underlined, respectively.
[a1]Restriction site BamH1 is underlined.
[b]Amino acid positions are according to xylanase sequences in the data banks.
[c]XYF1 or XYF1Bam and XYR1 are the forward and reverse primers used to amplify the feruloyl esterase domain from xylY (xynY) of *C. thermocellum* [see Fontes et al. (1995) supra].
[d]XZF1 is the forward primer and XZR1–XZR5 are the reverse primers used in the amplification of the feruloyl esterase portion of the xynZ of *C. thermocellum*.

TABLE 2

Distribution of proteins and hydrolytic activities in *C. thermocellum* culture grown on Avicel

| | Protein | | Feruloyl esterase | | Avicelase | | Xylanase | |
|---|---|---|---|---|---|---|---|---|
| Fraction | mg/ml | % | U/ml | % | U/ml | % | U/ml | % |
| Cell-associated | 0.09 | 39.1 | 0.005 | 2.1 | 0.001 | 2.4 | 0.49 | 5.3 |
| Cultural medium | 0.14 | 60.9 | 0.238 | 97.9 | 0.04 | 97.6 | 8.72 | 94.7 |
| After Avicel treatment | 0.11 | 47.8 | 0.002 | 0.8 | 0.004 | 9.7 | 1.56 | 16.9 |
| Avicel-bound | 0.03 | 13.2 | 0.24 | 97.1 | 0.033 | 80.5 | 6.75 | 73.3 |

TABLE 3A

Purification of the FAE/CBD polypeptide from *E. coli* cell free extract.

| Sample | Protein[a] (mg) | Total activity (U) | Specific Activity (U/mg) | Yield (%) | Purification Fold |
|---|---|---|---|---|---|
| Cell free extract | 2,597 | 3,253 | 1.25 | 100 | 1 |
| Heat treatment | 219.8 | 2,827 | 12.9 | 86.9 | 10.3 |

[a]The protein sample was obtained from 1.0 liter *E. coli* culture.

TABLE 3B

Purification of the XynZ FAE polypeptide from *E. Coli* cell free extract.

| Sample | Protein[a] (mg) | Total activity (U) | Specific Activity (U/mg) | Yield (%) | Purification Fold |
|---|---|---|---|---|---|
| Cell free extract | 532.6 | 1520 | 2.9 | 100 | 1 |
| Heat treatment | 212.5 | 1629 | 7.7 | 107 | 2.7 |
| TSK 3000SW | 30.9 | 823 | 26.6 | 54 | 9.7 |

[a]The protein sample was obtained from 1.0 liter *E. coli* culture.

TABLE 4

Substrate specificity of the feruloyl, esterase in *C. thermocellum* XynZ.

| Substrate | Specific activity (U/mg) |
|---|---|
| FAXX | 12.5 |
| FAX$_3$ | 11.8 |
| PAX$_3$ | 1.4[a] |
| Ethyl-FA | 0.066 |
| Ethyl-pCA | 0.022 |
| CMC | 0 |
| PNP-arabinopyranoside | 0 |
| PNP-glucopyranoside | 0 |
| PNP-xylopyranoside | 0 |
| Wheat bran | 0.06 |
| Coastal Bermuda grass | 0.1 |

[a]Calculated value based on substrate concentration used in the assay

TABLE 5

Nucleotide and Deduced Amino Acid Sequences of
Clostridium thermocellum Xylanase Y.
See also SEQ ID NO:11 and 12.

```
-200
TAAGAAACTTTAAAACACCCTTTATAAAAATACAAAGAATTACAGGCAATTATAGTGTAA

-100
TGTGGATTTTAACTAAAATGGAAGGAGGAATGTAATTGGTAATAGATATTATGATATAAT

TTGTTTAGAGCATGCTTAAGTTTATTTAAATTTAATTTATAAATTAAATTAAAAATTAAA

+1
ATTTAAAAGGAGGTTCCTTATGAAAAACAAGAGAGTTTTGGCAAAAATAACGGCTCTTGTG
                  M   K   N   K   R   V   L   A   K   I   T   A   L   V

100
GTATTGCTGGGAGTGTTTTTTGTATTACCGTCAAACATAAGTCAGCTATATGCTGATTAT
  V   L   L   G   V   F   F   V   L   P   S   N   I   S   Q   L   Y   A   D   Y
                                                          ↑
                                                          A

5'pCF6
                                                        ↓
GAAGTGGTTCATGACACTTTTGAAGTTAACTTTGACGGATGGTGTAACTTGGGAGTCGAC
  E   V   V   K   D   T   F   E   V   N   F   D   G   W   C   N   L   G   V   D

200
ACATATTTAACGGCAGTTGAAAATGAAGGAAACAACGGTACAAGAGGTATGATCGTAATA
  T   Y   L   T   A   V   E   N   E   G   N   N   G   T   R   G   M   M   V   I

AATCGCTCCAGTGCGAGTGACGGTGCGTATTCGGAAAAAGGTTTCTATCTCGACGGTGGT
  N   R   S   S   A   S   D   G   A   Y   S   E   K   G   F   Y   L   D   G   G

300
GTAGAATACAAGTACAGTGTTTTTGTAAAACACAACGGGACCGGCACCGAAACTTTCAAA
  V   E   Y   K   Y   S   V   F   V   K   H   N   G   T   G   T   E   T   F   K

400
```

TABLE 5-continued

Nucleotide and Deduced Amino Acid Sequences of
Clostridium thermocellum Xylanase Y.
See also SEQ ID NO:11 and 12.

```
CTTTCTGTGTCCTATTTGGATTCGGAAACAGAAGAAGAAAATAAGGAAGTAATTGCAACA
 L   S   V   S   Y   L   D   S   E   T   E   E   E   N   K   E   V   I   A   T

5'pCF7
                                                                      ↓
AAGGATGTTGTGGCCGGAGAATGGACTGAGATTTCGGCAAAATACAAAGCACCCAAAACT
 K   D   V   V   A   G   E   W   T   E   I   S   A   K   Y   K   A   P   K   T

500
GCAGTGAATATTACTTTGTCAATTACAACCGACAGCACTGTAGATTTCATTTTTGACGAT
 A   V   N   I   T   L   S   I   T   T   D   S   T   V   D   F   I   F   D   D

5'pCF2-5
  ↓
GTAACCATAACCCGTAAAGGAATGGCTGAGGCAAACACAGTATATGCAGCAAACGCTGTG
 V   T   I   T   R   K   G   M   A   E   A   N   T   V   Y   A   A   N   A   V

600
CTGAAAGATATGTATGCAAACTATTTCAGAGTTGGTTCGGTACTTAACTCCGGAACGGTA
 L   K   D   M   Y   A   N   Y   F   R   V   G   S   V   L   N   S   G   T   V
                                                 ↓
                                                 B

700
AACAATTCATCAATAAAGGCCTTGATTTTAAGAGAGTTTAACAGTATTACCTGTGAAAAT
 N   N   S   S   I   K   A   L   I   L   R   E   F   N   S   I   T   C   E   N

GAAATGAAGCCTGATGCCACACTGGTTCAATCAGGATCAACCAATACAAATATCAGGGTT
 E   M   K   P   D   A   T   L   V   Q   S   G   S   T   N   T   N   I   R   V

800
TCTCTTAATCGTGCAGCAAGTATTTTAAACTTCTGTGCACAAAATAATATAGCCGTCAGA
 S   L   N   R   A   A   S   I   L   N   F   C   A   Q   N   N   I   A   V   R

GGTCATACACTGGTTTGGCACAGCCAGACACCTCAATGGTTTTTCAAAGACAATTTCCAG
 G   H   T   L   V   W   H   S   Q   T   P   Q   W   F   F   K   D   N   F   Q

900
GACAACGGAAACTGGGTTTCCCAATCAGTTATGGACCAGCGTTTGGAAAGCTACATAAAA
 D   N   G   N   W   V   S   Q   S   V   M   D   Q   R   L   E   S   Y   I   K

1000
AATATGTTTGCTGAAATCCAAAGACAGTATCCGTCTTTGAATCTTTATGCCTATGACGTT
 N   M   F   A   E   I   Q   R   Q   Y   P   S   L   N   L   Y   A   Y   D   V

GTAAATGAGGCAGTAAGTGATGATGCAAACAGGACCAGATATTATGGCGGGGCGAGGGAA
 V   N   E   A   V   S   D   D   A   N   R   T   R   Y   Y   G   G   A   R   E

1100
CCTGGATACGGAAATCGTAGATCTCCATGGGTTCAGATCTACGGAGACAACAAATTTATT
 P   G   Y   G   N   R   S   P   W   V   Q   I   Y   G   D   N   K   F   I

5'pCF3
                                                      ↓
GAGAAAGCATTTACATATGCAAGAAAATATGCTCCGGCAAATTGTAAGCTTTACTACAAC
 E   K   A   F   T   Y   A   R   K   Y   A   P   A   N   C   K   L   Y   Y   N

1200
GATTACAACGAATATTGGGATCATAAGAGACACTGTATTGCCTCAATTTGTGCAAACTTG
 D   Y   N   E   Y   W   D   H   K   R   D   C   I   A   S   I   C   A   N   L

1300
TACAACAAGGGCTTGCTTGACGGTGTGGGAATGCAGTCCCATATTAATGCGGATATGAAT
 Y   N   K   G   L   L   D   G   V   G   M   Q   S   H   I   N   A   D   M   N

GGATTCTCAGGTATACAAAATTATAAAGCAGCTTTGCACAAATATATAAATATCGGTTGT
 G   F   S   G   I   Q   N   Y   K   A   A   L   Q   K   Y   I   N   I   G   C

1400
GATGTCCAAATTACCGAGCTTGATATTAGTACAGAAAACGGCAAATTTAGCTTACAGCAG
 D   V   Q   I   T   E   L   D   I   S   T   E   N   G   K   F   S   L   Q   Q
```

TABLE 5-continued

Nucleotide and Deduced Amino Acid Sequences of
Clostridium thermocellum Xylanase Y.
See also SEQ ID NO:11 and 12.

```
CAGGCTGATAAATATAAAGCTGTTTTCCAGGCAGCTGTTGATATAAACAGAACCTCCAGC
 Q   A   D   K   Y   K   A   V   F   Q   A   A   V   D   I   N   R   T   S   S

1500
AAAGGAAAGGTTACGGCTGTCTGTGTATGGGGACCTAATGACGCCAATACTTGGCTCGGT
 K   G   K   V   T   A   V   C   V   W   G   P   N   D   A   N   T   W   L   G

1600
TCACAAAATGCACCTCTTTTGTTTAACCCAAACAATCAACCGAAACCGGCATACAATGCG
 S   Q   N   A   P   L   L   F   N   A   N   N   Q   P   K   P   A   Y   N   A

3'pCF2-3
                  ↓
GTTGCATCCATTATTCCTCAGTCCGAATGGGGCGACGGTAACAATCCGGCCGGCGGCGGA
 V   A   S   I   I   P   Q   S   E   W   G   D   G   N   N   P   A   G   G   G

1700
GGAGGAGGCAAACCGGAAGAGCCGGATGCAAACGGATATTATTATCATGACACTTTTGAA
 G   G   G   K   P   E   E   P   D   A   N   G   Y   Y   Y   H   D   T   F   E
                ↑
                C

GGAAGCGTAGGACAGTGGACAGCCAGAGGACCTGCGGAAGTTCTGCTTAGCGGAAGAACG
 G   S   V   G   Q   W   T   A   R   G   P   A   E   V   L   L   S   G   R   P

1800
GCTTACAAAGGTTCAGAATCACTCTTGGTAAGGAACCGTACGGCAGCATGCAACGGAGCA
 A   Y   K   G   S   E   S   L   L   V   R   N   R   T   A   A   W   N   G   A

1900
CAACGGGCGCTGAATCCCAGAACGTTTGTTCCCGGAAACACATATTGTTTCAGGGTAGTG
 Q   R   A   L   N   P   R   T   F   V   P   G   N   T   Y   C   F   S   V   V

GCATCGTTTATTGAAGGTGGGTCTTCCACAACATTCTGCATGAAGCTCCAATACGTAGAC
 A   S   F   I   E   G   A   S   S   T   T   F   C   M   K   L   Q   Y   V   D

2000
GGAAGCGGCACTCAACGGTATGATACCATAGATATGAAAACTGTGGGTCCAAATCAGTGG
 G   S   G   T   Q   R   Y   D   T   I   D   M   K   T   V   G   P   N   Q   W

GTTCACCTGTACAATCCGCAATACAGAATTCCTTCCGATGCAACAGATATGTATGTTTAT
 V   H   L   Y   N   P   Q   Y   R   I   P   S   D   A   T   D   M   Y   V   Y

2100
GTGGAAACAGCGGATGACACCATTAACTTCTACATAGATGAGGCAATCGGAGCCGTTGCC
 V   E   T   A   D   D   T   I   N   P   Y   I   D   E   A   I   G   A   V   A

2200
GGAACTGTAATCGAAGGACCTGCTCCACAGCCTACACAGCCTCCGGTACTGCTTGGCGAT
 G   T   V   I   E   G   P   A   P   Q   P   T   Q   P   P   V   L   L   G   D
                                                                             ↓
                                                                             D

GTAAACGGTGATGGAACCATTAACTCAACTGACTTGACAATGTTAAAGAGAAGCGTGTTG
 V   N   G   D   G   T   I   N   S   T   D   L   T   M   L   K   R   S   V   L

2300
AGGGCAATCACCCTTACCGACGATGCAAAGGCTAGAGCAGACGTTGACAAGAATCGATCG
 R   A   I   T   L   T   D   D   A   K   A   R   A   D   V   D   K   N   G   S

3'pCF4
  ↓
ATAAACAGCACTGATGTTTTACTTCTTTCACGCTACCTTTTAAGAGTAATCGACAAATTT
 I   N   S   T   D   V   L   L   L   S   R   Y   L   L   R   V   I   D   K   F
                                                                 ↑
                                                                 E

2400
CCTGTAGCAGAAAATCCTTCTTCTTCTTTTAAATATGAGTCGGCCGTGCAATATCGGCCG
 P   V   A   E   N   P   S   S   S   F   K   Y   E   S   A   V   Q   Y   R   P

2500
GCTCCTGATTCTTATTTAAACCCTTGTCCGCAGGCGGGAAGAATTGTCAAGGAAACATAT
 A   P   D   S   Y   L   N   P   C   P   Q   A   G   R   I   V   K   E   T   Y
```

TABLE 5-continued

Nucleotide and Deduced Amino Acid Sequences of
*Clostridium thermocellum* Xylanase Y.
See also SEQ ID NO:11 and 12.

```
ACAGGAATAAACGGAACTAAGAGTCTTAATGTATATCTTCCATACGGTTATGATCCGAAC
 T  G  I  N  G  T  K  S  L  N  V  Y  L  P  Y  G  Y  D  P  N

2600
AAAAAATATAACATTTTCTACCTTATGCATGGCGGCGGTGAAAATGAGAATACGATTTTC
 K  K  Y  N  I  F  Y  L  M  H  G  G  G  E  N  E  N  T  I  F

AGCAACGATGTTAAATTGCAAAATATCCTTGACCACGCGATTATGAACGGTGAACTTGAG
 S  N  D  V  K  L  Q  N  I  L  D  H  A  I  M  N  G  E  L  E

2700
CCTTTGATTGTAGTAACACCCACTTTCAACGGCGGAAACTGCACGGCCCAAAACTTTTAT
 P  L  I  V  V  T  P  T  F  N  G  G  N  C  T  A  Q  N  F  Y

3'pCF6-8
            ↓                                           2800
CAGGAATTCAGGCAAAATGTCATTCCTTTTGTGGAAAGCAAGTACTCTACTTATGCAGAA
 Q  E  F  R  Q  N  V  I  P  F  V  E  S  K  Y  S  T  Y  A  E

TCAACAACCCCACAGGGAATAGCCGCTTCAAGAATGCACAGAGGTTTCGGCGGATTCTCA
 S  T  T  P  Q  G  I  A  A  S  R  M  H  R  G  F  G  G  F  S

2900
ATGGGAGGATTGACAACATGGTATGTAATGGTTAACTGCCTTGATTACGTTGCATATTTT
 M  G  G  L  T  T  W  Y  V  M  V  N  C  L  D  Y  V  A  Y  F

ATGCCTTTAAGCGGTGACTACTGGTATGGAAACAGTCCGCAGGATAAGGCTAATTCATT
 M  P  L  S  G  D  Y  W  Y  G  N  S  P  Q  D  K  A  N  S  I

3000
GCTGAAGCAATTAACAGATCCGGACTTTCAAAGAGGGAGTATTTCGTATTTGCGGCCACC
 A  E  A  I  N  R  S  G  L  S  K  R  E  Y  F  V  P  A  A  T

3100
GGTTCCGACCATATTGCATATGCTAATATGAATCCTCAAATTGAAGCTATGAAGGCTTTG
 G  S  D  H  I  A  Y  A  N  N  M  P  Q  I  E  A  K  K  A  L

CCGCATTTTGATTATACTTCGGATTTTTCCAAACGTAATTTTTACTTTCTTGTAGCTCCG
 P  H  F  D  Y  T  S  D  F  S  K  G  N  P  Y  F  L  V  A  P

]                         3200
GGCGCCACTCACTGGTGGGATACGTAAGACATTATATTTATGATGCACTTCCATATTTC
 G  A  T  H  W  W  G] Y  V  R  H  Y  I  Y  D  A  L  P  Y  F

TTCCATGAATGAATGAGAAAGAAAAACATGATTGAGTTTCTAATCAATAAAAAAAGGAA
 P  H  E

3300
TTTTTTAGTGGTGTCCAGGTTATTGAA
```

Nucleotide sequence of xynY
The nucleotide sequence of xynY and the deduced primary structure of XYLY are shown. The locations of the first residues of domains A, B, C, D and E are indicated with the corresponding letters. The positions of the two primers used to amplify the region of xynY coding for the catalytic domain of the xylanase (pCF2/3) are indicated by overlining. The 5' and 3' nucleotides of truncated forms of xynY are indicated by a downward arrow and the plasmids that encode the derivatives of the xylanase gene. The nucleotide sequence has been submitted to the EMBL database under the accession number X83269.

TABLE 6

See also SEQ ID NO:13 and 14.

```
ATATATAAAT AAGGGTATTA ATTCTGCAAA AAGAAAAGTG TTTGCTACAT GAGGTCCATT AATTTTTATT TTATATCATA AATCAAAAAG GAGGAGAAAC
-100                                                                                                 ‾‾SD‾‾   -1

1
MET SER ARG LYS LEU PHE SER VAL LEU LEU VAL GLY LEU MET LEU MET THR SER LEU LEU VAL THR ILE SER SER THR SER ALA
ATG TCA ACA AAA CTT TTC AGT GTA TTA CTT GTT GGC TTG ATG CTT ATG ACA TCG TTG CTT GTC ACA ATA AGC AGT ACA TCA GCG
1

50
ALA SER LEU PRO THR MET PRO PRO SER GLY TYR ASP GLN VAL ARG ASN GLY VAL PRO ARG GLY GLN VAL VAL ASN ILE SER TYR
GCA TCC TTG CCA ACC ATG CCG CCT TCG GGA TAT GAC CAG GTA ACG AAC GGC GTT CCG AGA GGG CAG GTC GTA AAT ATT TCT TAT
                 100

PHE SER THR ALA THR ASN SER THR ARG PRO ALA ARG VAL TYR LEU PRO PRO GLY TYR SER LYS ASP LYS LYS TYR SER VAL LEU
TTC TCC ACG GCC ACC AAC AGT ACC AGG CCG GCA AGA GTT TAT TTG CCG CCG GGA TAT TCA AAG GAC AAA AAA TAC AGT GTT TTG
                                200
                                                            100
TYR LEU LEU HIS GLY ILE GLY GLY SER GLU ASN ASP TRP PHE GLU GLY GLY GLY ARG ALA ASN VAL ILE ALA ASP ASN LEU ILE
TAT CTC TTA CAC GGC ATA GGC GGC AGT GAA AAC GAC TGG TTC GAA GGG GGA GCC AGA GCC AAT GTT ATT GCC GAC AAT CTG ATT
                                                       300

ALA GLU GLY LYS ILE LYS PRO LEU ILE ILE VAL THR PRO ASN THR ASN ALA ALA GLY PRO GLY ILE ALA ASP GLY TYR GLU ASN
GCC GAG GGA AAA ATC AAG CCC CTG ATA ATT GTA ACA CCG AAT ACT AAC GCC GCC GGT CCG GGA ATA GCG GAC GGT TAT GAA AAT
                                                                              400

150
PHE THR LYS ASP LEU LEU ASN SER LEU ILE PRO TYR ILE GLU SER ASN TYR SER VAL TYR THR ASP ARG GLU HIS ARG ALA ILE
TTC ACA AAA GAT TTG CTC AAC AGT CTT ATT CCC TAT ATC GAA TCT AAC TAT TCA GTC TAC ACC GAC CGC GAA CAT CGG GCG ATT
                                                                                                     500

ALA GLY LEU SER MET GLY GLY GLY GLN SER PHE ASN ILE GLY LEU THR ASN LEU ASP LYS PHE ALA TYR ILE GLY PRO ILE SER
GCA GGA CTT TCA ATG GGT GGA GGA CAA TCG TTT AAT ATT GGA TTG ACC AAT CTC GAT AAA TTT GCC TAT ATT GGC CCG ATT TCA

200
ALA ALA PRO ASN THR TYR PRO ASN GLU ARG LEU PHE PRO ASP GLY GLY LYS ALA ALA ARG GLU LYS LEU LYS LEU LEU PHE ILE
GCG GCT CCA AAC ACT TAT CCA AAT GAG AGG CTT TTT CCT GAC GGA GGA AAA GCT GCA AGG GAG AAA CTG AAA CTG CTC TTT ATT
            600
                                                                                     250
ALA CYS GLY THR ASN ASP SER LEU ILE GLY PHE GLY GLN ARG VAL HIS GLU TYR CYS VAL ALA ASN ASN ILE ASN HIS VAL TYR
GCC TGC GGA ACC AAT GAC AGT CTG ATA GGT TTT GCA CAG AGA GTA CAT GAA TAT TGC GTT GCC AAC AAC ATT AAC CAT GTC TAT
                                    700

TRP LEU ILE GLN GLY GLY GLY HIS ASP PHE ASN VAL TRP LYS PRO GLY LEU TRP ASN PHE LEU GLN MET ALA ASP GLU ALA GLY
TGG CTT ATT CAG GGC GCA GGA CAC GAT TTT AAT GTG TGG AAG CCC GGA TTG TGG AAT TTC CTT CAA ATG GCA GAT GAA GCC GGA
                                                            800
                                                                            300
LEU THR ARG ASP GLY ASN THR PRO VAL PRO THR PRO SER PRO LYS PRO ALA ASN THR ARG ILE GLU ALA GLU ASP TYR ASP GLY
TTC ACG AGG GAT GGA AAC ACT CCG GTT CCG ACA CCC AGT CCA AAG CCG GCT AAC ACA CGT ATT GAA GCG GAA GAT TAT GAC GGT
                                                                            900

ILE ASN SER SER SER ILE GLU ILE ILE GLY VAL PRO PRO GLU GLY GLY ARG GLY ILE GLY TYR ILE THR SER GLY ASP TYR LEU
ATT AAT TCT TCA AGT ATT GAG ATA ATA GGT GTT CCA CTT GAA CGA GGC AGA GGA ATA GGT TAT ATT ACC AGT GGT GAT TAT CTG
                                                                                                1000
            ┌─ pCT1208, pCT1211                                             ┌─ pCT1223
            │                                       350                     │
VAL TYR LYS SER ILE ASP PHE GLY ASN GLY ALA THR SER PHE LYS ALA LYS │VAL ALA ASN ALA ASN THR SER ASN ILE GLU LEU
GTA TAC AAG AGT ATA GAC TTT GGA AAC GGA GCA ACG TCG TTT AAG GCC AAG│GTT GCA AAT GCA AAT ACT TCC AAT ATT GAA CTT

ARG LEU ASN GLY PRO ASN GLY THR LEU ILE GLY THR LEU SER VAL LYS SER THR GLY ASP TRP ASN THR TYR GLU GLU GLN THR
AGA TTA AAC GGT CCG AAT GGT ACT CTC ATA GGC ACA CTC TCG GTA AAA TCC ACA GGA GAT TGG AAT ACA TAT GAG GAG CAA ACT
            1100
```

TABLE 6-continued

See also SEQ ID NO:13 and 14.

```
                                400
CYS SER ILE SER LYS VAL THR GLY ILE ASN ASP LEU TYR LEU VAL PHE LYS GLY PRO VAL ASN ILE ASP TRP PHE THR PHE GLY
TGC AGC ATT AGC AAA GTC ACC GGA ATA AAT GAT TTG TAC TTG GTA TTC AAA GGC CCT GTA AAC ATA GAC TGG TTC ACT TTT GGC
                                    1200

VAL GLU SER SER SER THR GLY LEU GLY |ASP LEU ASN GLY ASP GLY ASN ILE ASN SER SER ASP LEU GLN ALA LEU LYS ARG HIS
GTT GAA AGC AGT TCC ACA GGT CTG GGG |GAT TTA AAT GGT GAC GGA AAT ATT AAC TCG TCG GAC CTT CAG GCG TTA AAG AGG CAT
                                                            1300

450
LEU LEU GLY ILE SER| PRO LEU THR GLY GLU ALA LEU LEU ARG ALA |ASP VAL ASN ARG SER GLY LYS VAL ASP SER THR ASP TYR
TTG CTC GGT ATA TCA| CCG CTT ACG GGA GAG GCT CTT TTA AGA GCG |GAT GTA AAT AGG AGC GGC AAA GTG GAT TCT ACT GAC TAT
                                                                            1400 pCT1214
                                                              ┌── pCT1215                          pCT1216
                                                              │                               500 ┌── pCT1217
SER VAL LEU LYS ARG TYR ILE LEU ARG ILE ILE| THR GLU PHE PRO |GLY| GLN GLY ASP VAL GLN THR PRO |ASN| PRO SER VAL THR
TCA GTG CTG AAA AGA TAT ATA CTC CGC ATT ATT| ACA GAG TTC CCC |GGA| CAA GGT GAT GTA CAG ACA CCC |AAT| CCG TCT GTT ACT
                                                                                                1500 pCT1218
PRO THR| GLN THR| PRO ILE PRO THR ILE SER GLY ASN ALA LEU ARG ASP TYR ALA GLU ALA ARG GLY ILE LYS ILE GLY THR CYS
CCG ACA| CAA ACT| CCT ATC CCC ACG ATT TCG GGA AAT GCT CTT AGG GAT TAT GCG GAG GCA AGG GCA ATA AAA ATC GGA ACA TGT
        pCT1219 pCT1220                 pCT1221
VAL ASN TYR PRO PHE TYR ASN ASN SER ASP PRO THR TYR ASN SER ILE LEU GLN ARG GLU PHE SER MET VAL VAL CYS GLU ASN
GTC AAC TAT CCG TTT TAC AAC AAT TCA GAT CCA ACC TAC AAC AGC ATT TTG CAA AGA GAA TTT TCA ATG GTT GTA TGT GAA AAT
1600

GLU MET LYS PHE ASP ALA LEU GLN PRO ARG GLN ASN VAL PHE ASP PRE SER LYS GLY ASP GLN LEU LEU ALA PHE ALA GLU ARG
GAA ATG AAG TTT GAT GCT TTG CAG CCG AGA CAA AAC GTT TTT GAT TTT TCG AAA GGA GAC CAG TTG CTT GCT TTT GCA GAA AGA
                    1700

600
ASN GLY MET GLN MET ARG GLY HIS THR LEU ILE TRP HIS ASN GLN ASN PRO SER TRP LEU THR ASN GLY ASN TRP ASN ARG ASP
AAC GGT ATG CAG ATG AGG GGA CAT ACG TTG ATT TGG CAC AAT CAA AAC CCG TCA TGG CTT ACA AAC GGT AAC TGG AAC CGG GAT
                                    1800

SER LEU LEU ALA VAL MET LYS ASN HIS ILE THR THR VAL MET THR HIS TYR LYS GLY LYS ILE VAL GLU TRP ASP VAL ALA ASN
TCG CTG CTT GCG GTA ATG AAA AAT CAC ATT ACC ACT GTT ATG ACC CAT TAC AAA GCT AAA ATT GTT GAG TGG GAT GTG GCA AAC
                                                                    1900

650
GLU CYS MET ASP ASP SER GLY ASN GLY LEU ARG SER SER ILE TRP ARG ASN VAL ILE GLY GLN ASP TYR LEU ASP TYR ALA PHE
GAA TGT ATG GAT GAT TCC GGC AAC GGC TTA AGA AGC AGC ATA TGG AGA AAT GTA ATC GGT CAG GAC TAC CTT GAC TAT GCT TTC
                                                                                        2000

700
ARG TYR ALA ARG GLU ALA ASP PRO ASP ALA LEU LEU PHE TYR ASN ASP TYR ASN ILE GLU ASP LEU GLY PRO LYS SER ASN ALA
AGG TAT GCA AGA GAA GCA GAT CCC GAT GCA CTT CTT TTC TAC AAT GAT TAT AAT ATT GAA GAC TTG GGT CCA AAG TCC AAT GCG
                                                                                                         2100

VAL PHE ASN MET ILE LYS SER MET LYS GLU ARG GLY VAL PRO ILE ASP GLY VAL GLY PHE GLN CYS HIS PHE ILE ASN GLY MET
GTA TTT AAC ATG ATT AAA AGT ATG AAG GAA AGA GGT GTG CCG ATT GAC GGA GTA GGA TTC CAA TGC CAC TTT ATC AAT GGA ATG
                                                                                            750
SER PRO GLU TYR LEU ALA SER ILE ASP GLN ASN ILE LYS ARG TYR ALA GLU ILE GLY VAL ILE VAL SER PHE THR GLU ILE ASP
AGC CCC GAG TAC CTT GCC AGC ATT GAT CAA AAT ATT AAG AGA TAT GCG GAA ATA GGC GTA ATA GTA TCC TTT ACC GAA ATA GAT
                    2200

ILE ARG ILE PRO GLN SER GLU ASN PRO ALA THR ALA PHE GLN VAL GLN ALA ASN ASN TYR LYS GLU LEU MET LYS ILE CYS LEU
ATA CGC ATA CCT CAG TCG GAA AAC CCG GCA ACT GCA TTC CAG GTA CAG GCA AAC AAA TAT AAG GAA CTT ATG AAA ATT TCT CTG
                                            2300
                                 800
ALA ASN PRO ASN CYS ASN THR PHE VAL MET TRP GLY PHE THR ASP LYS TYR THR TRP ILE PRO GLY THR PHE PRO GLY TYR GLY
GCA AAC CCC AAT TGC AAT ACC TTT GTA ATG TGG GGA TTC ACA GAT AAA TAC ACA TGG ATT CCG GGA ACT TTC CCA GGA TAT GCC
                                                    2400

ASN PRO LEU ILE TYR ASP SER ASN TYR ASN PRO LYS PRO ALA TYR ASN ALA ILE LYS GLU ALA LEU MET GLY TYR END
AAT CCA TTG ATT TAT GAC AGC AAT TAC AAT CCG AAA CCG GCA TAC AAT GCA ATA AAG GAA GCT CTT ATG GGC TAT TGA TAATTCC
                                                                                                        2500

GAA AAGCTGAGCA GATAATGATG CCGTAAAGCC GGCTTCTGAA TTAAGAGCCG GCTTTACGGA CATATACTTT TTACGGCAGA ATACCTGTTA ATACCTGTTA TTTCCATG
                                  ──────────▶                ◀──────────
                                                                                2600
```

Nucleotide sequence and deduced amino acid sequence of the xynZ gene of *C. thermocellum*. Numbering of both nucleotides amino acids starts with the beginning of the coding sequence. The putative Shine-Dalgarno sequence (SD) is underlined. Pro- and Thr- regions are in boldface type. The conserved, duplicated stretch is boxed (residues 430 to 453 and 464 to 487). A perfect 14-bp palindr which may serve as a transcription terminator is indicated by inverted arrows. Arrows in the coding sequence indicate the beginning of xynZ gene in the deleted clones.

TABLE 7

Purification of a Feruloyl Esterase from Orpinomyces PC-2 Culture Supernatant

| Step | Total Activity (U) | Total Protein (mg) | Specific Activity (Umg$^{-1}$) | Purification Fold |
|---|---|---|---|---|
| Culture Supernatant | 32.38 | 5,830 | 5.6E−3 | 1 |
| Concentrate | 7.9 | 1460 | 5.42E−3 | 0.96 |
| Q Sepharose | 2.58 | 181 | 1.43e−2 | 2.55 |
| Phenyl Sepharose HP | 1.68 | 28.2 | 5.96E−2 | 10.6 |
| TSK 3000SW | 0.85 | 0.62 | 1.39 | 253 |
| Mono Q HR 5/5 | 0.26 | 0.24 | 1.087 | 198 |

TABLE 8

Substrate specificity of Orpinomyces FaeA

| Sample | $\mu$mole FA released min$^{-1}$ mg enzyme$^{-1}$ |
|---|---|
| FAXX | 2.05 |
| FAX$_3$ | 1.80 |
| Ethyl-ferulate | 0.07 |
| Ethyl-p-coumarate | 0.02 |
| Wheat Bran FaeA | 0.0002 |
| Wheat bran FaeA + XynA | 0.013 |

All reactions were carried out in 50 mM citrate buffer pH 6.0. FAXX, FAX$_3$, Et-FA and Et pCA were assayed for 5 min at 40° C. at a concentration of 10 mM. Enzyme solution ($\mu$L) was added 400 $\mu$L of substrate solution. The reaction was stopped with 25 $\mu$L of 20% formate.

For studies on wheat bran, crude recombinant FaeA (50 $\mu$L) equaling 0.7 units of activity against FAXX, XynA (50 $\mu$L) equaling 300 units of activity against birchwood xylan or both was added to a total reaction volume of 1 ml also containing 10 mg of destarched wheat bran. The reaction was carried out for 40 min at 40° C. and stopped by adding 50 $\mu$L of 20% formate.

TABLE 9

Nucleotide and Deduced Amino Acid Sequence for Feruloyl Esterase from Orpinomyces PC-2. See also SEQ ID NO:17 and 18

```
       GGTTGTTTCTTGTGAAACTACTTACGGTATTACTTTACGTGATACTA
  1    V  V  S  C  E  T  T  Y  G  I  T  L  R  D  T  K

AGGAAAAATTCACTGTATTCAAAGACGGTTCCGCTGCTACTGATATTGTTGAATCAGAAG
 17    E  K  F  T  V  F  K  D  G  S  A  A  T  D  I  V  E  S  E  D

ATGGTTCCGTTTCTTGGATTGCTACTGCTGCCGGTGGTGCTGGTGGTGGTGTTGCCTTCT
 37    G  S  V  S  W  I  A  T  A  A  G  G  A  G  G  G  V  A  F  Y

ATGTTAAGGCTAACAAGGAAGAAATTAACATTGCTAACTATGAATCTATCGATATTGAAA
 57    V  K  A  N  K  E  E  I  N  I  A  N  Y  E  S  I  D  I  E  M

TGGAATACACTCCAGTTGAAAACAAATGGAATGATGCTGCTAAGAACCCAAGTTTCTGTA
 77    E  Y  T  P  V  E  N  K  W  N  D  A  A  K  N  P  S  F  C  M

TGAGAATTCTTCCATGGGATTCCACTGGTATGTTCGGTGGTTACGAAGATCTTGAATACT
 97    R  I  L  P  W  D  S  T  G  M  F  G  G  Y  E  D  L  E  Y  F

TCGATACTCCAGCAAAATCTGGTAATTTCAAATACACTATTAAGATTCCTTCCTTCTTTG
117    D  T  P  A  K  S  G  N  F  K  Y  T  I  K  I  P  S  F  F  A

CTGATAAGATTTTATCTAGCTCTGATCTCGATTCTATCTTAAGTTTTGCTATCAAGTTCA
137    D  K  I  L  S  S  S  D  L  D  S  I  L  S  F  A  I  K  F  N

ACGATTATGAAAGAGGTAACACGGACGGTGACCAAATTAAGATTCAATTAAAGAATGTTA
157    D  Y  E  R  G  N  T  D  G  D  Q  I  K  I  Q  L  K  N  V  K

AATTCAACCCAAAGGAAAATGCTCCAGAAGATAAGGCTTTCGATGATGGTTTAAGGGATT
177    F  N  P  K  E  N  A  P  E  D  K  A  F  D  D  G  L  R  D  S

CTCAACGTGGTACTGTCGTTGAAATGAAATACTCATCTAGAGATTACACCGTCAAGGAAT
197    Q  R  G  T  V  V  E  M  K  Y  S  S  R  D  Y  T  V  K  E  S

CTGAAGCTGACAAATACGAAAAGCACGCTTGGGTTTACCTTCCAGCTGGTTATGAAGCTG
217    E  A  D  K  Y  E  K  H  A  W  V  Y  L  P  A  G  Y  E  A  D

ATAACAAGGATAAGAAATACCCATTAGTTGTTTTACTTCACGGTTATGGTCAAAATGAAA
237    N  K  D  K  K  Y  P  L  V  V  L  L  H  G  Y  G  Q  N  E  N

ACACTTGGGGTCTTTCCAACAAGGGTCGTGGTGGTAAGATCAAGGGTTACATGGACAGAG
257    T  W  G  L  S  N  K  G  R  G  G  K  I  K  G  Y  M  D  R  G

GTATGGCTAGTGGTAATGTTGAAAAGTTTGTTCTTGTTGCCGCTACTGGTGTTGCCAGTA
277    M  A  S  G  N  V  E  K  F  V  L  V  A  A  T  G  V  A  S  K

AGAATTGGGGTCCAAACGGTTCTGGTGTTGATCTTGATGGTTTCAATGCTTTCGGTGGTG
297    N  W  G  P  N  G  S  G  V  D  L  D  G  F  N  A  F  G  G  E
```

TABLE 9-continued

Nucleotide and Deduced Amino Acid Sequence for Feruloyl Esterase from Orpinomyces PC-2. See also SEQ ID NO:17 and 18

```
    AACTCAGAAACGATTTACTCCCATACATTAGAGCTCACTTCAATGTTAAGGTCGATCGTG
317 L   R   N   D   L   L   P   Y   I   R   A   H   F   N   V   K   V   D   R   D

ATCACACTGCTTTAGCTGGTCTTTCCATGGGTGGTGGTCAAACTATCAGTATTGGTATTG
337 H   T   A   L   A   G   L   S   M   G   G   G   Q   T   I   S   I   G   I   G

GTGAAACTCTTGATGAAATCAGTAACTACGGTTCTTTCTCCAGCTTTATTCCAAACTG
357 E   T   L   D   E   I   S   N   Y   G   S   F   S   P   A   L   F   Q   T   A

CTGAAGAATTCTTCGGTAAGGTTAAGGGTAACTTCAAGGAAGAACTTAGAATTCACAACC
377 E   E   F   F   G   K   V   K   G   N   F   K   E   E   L   R   I   H   N   L

TTTACATGACTTGTGGTGATGCTGATACTTTAGTTTACGATACTTACCCAAGTTACGTTG
397 Y   M   T   C   G   D   A   D   T   L   V   Y   D   T   Y   P   S   Y   V   E

AAGCTTTAAAGAATTGGGATGCTGTTGAATTCATGAAGGAATACACTTACCCAGGTGGTA
417 A   L   K   N   W   D   A   V   E   F   M   K   E   Y   T   Y   P   G   G   T

CTCACGATTTCCCAGTTTGGTACAGAGGTTTCAACGAATTCATTCAAATTGTTTTCAAAA
437 H   D   F   P   V   W   Y   R   G   F   N   E   F   I   Q   I   V   F   K   N

ATCAAAAAGTTAAGGAAGAACCAATTCATGCTGATCCAGTAGAAGACCCATCTGATGAAC
457 Q   K   V   K   E   E   P   I   H   A   D   P   V   E   D   P   S   D   E   P

CAGTTAGTGTTGATCCATCTGTTTCTGTCGAAGAACCAAATGACAGTGAATCTTCCTCTG
477 V   S   V   D   P   S   V   S   V   E   E   P   N   D   S   E   S   S   S   E

AAGATGAACCAGTGGTTAAAAAAACTATTAAGCACACCATTGCTAAGAAGAAGCCATCTA
497 D   E   P   V   V   K   K   T   I   K   H   T   I   A   K   K   K   P   S   K

AGACTAGAACTGTTACCAAGAAGGTCATTAAGAAGAAGAATAACTAAGAAAGTTTAGTTA
517 T   R   T   V   T   K   K   V   I   K   K   K   N   N

GTACAGTAGTGTAAAAAAAAAAAAAAAATCAAAAAGAAACTCGTGCCGAATTCGAT
```

TABLE 10

Nucleotide and Deduced Amino Acid Sequence for Ruminococcus sp. Xylanase (Xyn1) See also SEQ ID NO:15 and 16

GENBANK ACCESSION Z49970
Amino Acid Sequence

MKKTVKQFISSAVTALMVAASLPAVPSVNAADAQQRGNIGGFDY

EMWNQNGQGQVSMTPKAGSFTCSWSNIENFLARMGKNYDSQKKNYKAFGDITLSYDVE

YTPKGNSYMCVYGWTRNPLMEYYIVEGWGDWRPPGNDGENKGTVTLNGNTYDIRKTMR

YNQPSLDGTATFPQYWSVRQKSGSQNNTTNYMKGTISVSKHFDAWSKAGLDMSGTLYE

VSLNIEGYRSSGNANVKAISFDGSIPEPTSEPVTQPVVKAEPDANGYYFKEKFESGAG

DWSARGTGAKVTSSDGFNGSKGILVSGRGDNWHGAQLTLDSSAFTAGETYSFGALVKQ

DGESSTAMKLTLQYNDASGTANYDKVAEFTAPKGEWVDLSNTSFTIPSGASDLILYVE

APDSLTDFYIDNAFGGIKNTSPLEDVGSHTISTPGSETTTVTTASNKGIRGDINGDGV

INSFDLAPLRRGILKMMSGSGSTPENADVNGDGTVNVADLLLLQKFILGMEKSFPDPV

TTTTTKPITTTTEKIVTTTTSSSSSSSGKNLNADIRKDMPTSVPGGNEKSGGCKVEKK

TYNCKFTGGQKSCNVILPPNYSASKQYPVMYVLHGIGGNEGSMVSGMGVQELLAGLTA

NGKAEEMIIVLPSQYTSKNGNQGGGFGINQEVCAAYDNFLYDISDSLIPFIEANYPVK

TGRENRAITGFSMGGREAIYIGLMRPDLFAYVGGACPAPGITPGKDMFMEHPGCMQES

EMKFRDVGPEPNVFMITGGTNDGVVGTFPKQYSDILTRNGVDQRLPVYP"

Coding Sequence Nucleotides 529–2898

TABLE 10-continued

Nucleotide and Deduced Amino Acid Sequence for Ruminococcus sp. Xylanase (Xyn1) See also SEQ ID NO:15 and 16 signal peptide   encoded at nucleotides 529–627
mature peptide   encoded at nucleotides 628–2895

```
   1 gatctttttc ataagtatgc ccccattatt aagtttttta gatgcttgcc tataatttcc
  61 cttctggttt tgtgaacttc ttaacggtca gagttcacac tttctttata tattgtctat
 121 attataatgt atattgtagt aataatatac caaaattttc ctttaagtaa caatatcttt
 181 accctattta gcaattttta acgatatttt ataatttgat tattttaaa ctatacagtg
 241 taaatactat tatttaaaaa gtccaccaaa aatgtaaaat acaatgatat cttaaacgta
 301 aaaacctgta caatgattgt tcatcttttt acattattgt tatatatcgt cttggtatag
 361 tcagcaattt ttagtcaaga tatacaaggt ccgcaaattt taacttgcaa ttaacaggtc
 421 agatgttta taatgatatc atagaaataa aaggagcact tggctcctta tggggattac
 481 tgaaatcata agtttgcttt ttttctaaaa acaaaggag tgattgaagt gaaaaaaaca
 541 gttaaacaat tcatcagcag tgccgttaca gcgttaatgg tggctgcaag cctgcctgcc
 601 gttccttccg tgaacgcagc cgacgcccag cagagaggca atatcggcgg tttcgattac
 661 gaaatgtgga accagaacgg tcagggacag gtatcaatga cgcctaaggc aggctctttc
 721 acctgctcat ggagcaacat tgaaaacttc ctcgcacgta tgggcaagaa ctacgacagc
 781 cagaaaaaga actacaaggc tttcggagac attaccctct cctacgacgt agagtacacc
 841 cccaagggca actcttatat gtgcgtatac ggctggacga ggaaccctct catgaaatac
 901 tacatcgtcg aaggctgggg cgactggcgt ccacccggaa atgacggcga aaacaagggt
 961 acagttaccc tgaacggcaa cacctacgat atccgcaaaa caatgcgtta taatcagcca
1021 tctctggacg gcacggctac attccctcag tactggagcg tacgtcagaa gagcggttca
1081 cagaataata ccaccaacta tatgaaggt actatcacg tatccaagca ctttgacgca
1141 tggtcaaagg caggtctgga tatgagcggt actctctacg aggtatccct caacatcgag
1201 ggctacagat caagcggaaa cgctaacgtt aaagctatct cattcgacgg cagtataccc
1261 gagcccacaa gcgagcccgt aactcagccc gttgtcaagg cagagcctga cgcaaacggc
1321 tactacttca aagaaaaatt cgagagcggc gcaggcgact ggtcagcccg cggaacagga
1381 gctaaggtaa caagctctga cggattcaac ggttcaaagg catactggt atcaggacgc
1441 ggcgacaact ggcacggcgc acagctcaca ctcgactcaa gtgctttcac agcaggcgaa
1501 acatacagct tcggcgcact tgtaaagcag gacggcgagt cctcaacagc tatgaagctc
1561 actctccagt ataacgacgc aagcggcaca gccaattacg ataaggtggc agagttcaca
1621 gctccaaagg gtgaatgggt agacctttcc aatacatcgt tcactatccc gtcaggcgct
1681 tcagacctca ttctctatgt tgaagctccc gacagcctta cggattctta tatcgacaac
1741 gctttcggcg gcatcaagaa cacatctcct cttgaagatg tcggaagcca tactatcagc
1801 actccgggca gcgagacaac aacagtcaca actgcatcaa ataagggtat cagaggcgat
1861 atcaacggcg acggcgttat caactcattc gaccttgctc ctctcagaag aggcattctc
1921 aagatgatgt caggcagcgg ctcgactccc gaaaatgctg acgtaaacgg cgacggcact
1981 gtaaatgttg cagacctcct gcttctccag aagtttatac tcggtatgga gaagtcattc
2041 cccgatcctg taacaactac cacgaccaag ccgataacaa caactaccga gaagatagtt
2101 accacaacta cttcttcatc ttcttcaagc tcaggcaaga acctcaatgc agatatccgt
2161 aaggatatgc ctacttcagt tcccggcgga aacgaaaaga gcggcggctg caaggtcgag
2221 aagaagacat acaactgcaa gttcacaggc ggtcagaaga gctgcaacgt tatcctgcct
2281 cctaactaca gcgcaagcaa gcagtaccct gttatgtacg ttctccacgg tatcggcgga
2341 aacgagggaa gcatggtaag cggcatgggc gttcaggagc ttcttgcagg acttaccgca
2401 aacggcaagg cagaggaaat gataatcgtt ctcccgagcc agtacaccag caagaacggc
2461 aatcagggcg gcgcttcgg aatcaatcag gaagtatgcg cagcttacga taacttcctc
2521 tatgatatct cagacagcct tatcccattc atcgaggcta actatcccgt taagacaggc
2581 agagaaaacc gtgctatcac aggcttctca atgggcgac gtgaagctat ctatatcggt
2641 cttatgcgtc ccgacctctt cgcttacgtt ggcggagctt gccctgcacc cggtatcacc
2701 ccaggcaagg atatgttcat ggagcaccca ggctgtatgc aggagagcga aatgaagttc
2761 agagacgttg gacctgagcc gaatgtattc atgataacag cggcacaaa cgacggcgtc
2821 gtaggaacat tccccaagca gtacagcgat atccttacaa gaaacagcgt tgaccaacgt
2881 ttaccagtct atccctaacg gcggacacga cgcaggctct gtaaagcctc atctctacac
2941 attcatgaga tacgcattca aataatgata tagttgacat atgaaggaca gcgctttatg
3001 cgctgtcttt ctttttgtgc aaaaagaaaa gccatttgag cttttgaagc tcaaatggct
3061 tatatttata atagtatagc ttattctgtt ctgagagcct ccaca
```

TABLE 11

Composition of basal diet in broiler feeding experiments

| Ingredient | Amount (%) |
| --- | --- |
| Wheat | 63.41 |
| Soybean meal (49%) | 31.85 |
| Fat | 0.50 |
| Salt | 0.44 |
| Limestone | 1.67 |
| Dical | 1.52 |
| Vitamins | 0.25 |
| Methionine | 0.24 |
| Trace minerals | 0.06 |
| Lysine | 0.05 |
| Calculated analysis | |
| Crude protein | 22.48 |
| Energy, ME, kcal/kg | 2853 |

TABLE 11-continued

Composition of basal diet in broiler feeding experiments

| Ingredient | Amount (%) |
|---|---|
| Lysine | 1.22 |
| Methionine | 0.58 |

TABLE 12

Improvement in Performance Expressed as Percent Relative to Control

| | Control | Feruloyl Esterase | Xylanase A | Xylanase A + Feruloyl Esterase Z |
|---|---|---|---|---|
| Gain | 100 | 97 | 107 | 115 |
| Feed Efficiency | 100 | 104 | 95 | 90 |

TABLE 13 cDNA sequence for xylanase of Orpinomyces Strain PC-2. See also SEQ ID NO:25 and 26

```
GGCACGAGGA AATTTTTTTT ACTGGTTAAA AAAAAATTAT AAAACTAAAT AAATAAAAAA    60

AATATTTTTT GAAATATATT AAAATAGGAA AAAAAA ATG AGA ACT ATT AAA TTT    114
                                    Met Arg Thr Ile Lys Phe
                                     1                  5

TTA TTC GCA TTA GCT ATT ACA ACC GTT GCT AAG GCC CAA TGG GGT GGA    162
Leu Phe Ala Leu Ala Ile Thr Thr Val Ala Lys Ala Gln Trp Gly Gly
            10                  15                  20

AAC GGT GGT GCC TCT GCT GGT CAA AGA TTA AGC GTT GGT GGT GGT CAA    210
Asn Gly Gly Ala Ser Ala Gly Gln Arg Leu Ser Val Gly Gly Gly Gln
        25                  30                  35

AAC CAA CAT AAA GGT GTT TTT GAT GGC TTC AGT TAT GAA ATC TGG TTA    258
Asn Gln His Lys Gly Val Phe Asp Gly Phe Ser Tyr Glu Ile Trp Leu
    40                  45                  50

GAT AAC ACC GGT GGT AGT GGT TCC ATG ACC CTT GGT AAA GGT GCA ACC    306
Asp Asn Thr Gly Gly Ser Gly Ser Met Thr Leu Gly Lys Gly Ala Thr
55                  60                  65                  70

TTC AAG GCT GAA TGG AGT GCA GCT GTT AAC CGT GGT AAC TTC CTT GCC    354
Phe Lys Ala Glu Trp Ser Ala Ala Val Asn Arg Gly Asn Phe Leu Ala
                75                  80                  85

CGT CGT GGT CTT GAT TTC GGT TCT ACC AAA AAG GCA ACC GCT TAC GAA    402
Arg Arg Gly Leu Asp Phe Gly Ser Thr Lys Lys Ala Thr Ala Tyr Glu
            90                  95                 100

TAC ATC GGA TTG GAT TAT GAA GCA AGT TAC AGA CAA ACT GCC AGC GCA    450
Tyr Ile Gly Leu Asp Tyr Glu Ala Ser Tyr Arg Gln Thr Ala Ser Ala
        105                 110                 115

AGT GGT AAC TCC CGT CTT TGT GTA TAC GGC TGG TTC CAA AAC CGT GGA    498
Ser Gly Asn Ser Arg Leu Cys Val Tyr Gly Trp Phe Gln Asn Arg Gly
    120                 125                 130

GTT CAA GGC GTA CCT TTG GTA GAA TAC TAC ATC ATT GAA GAT TGG GTT    546
Val Gln Gly Val Pro Leu Val Glu Tyr Tyr Ile Ile Glu Asp Trp Val
135                 140                 145                 150

GAC TGG GTA CCA GAT GCA CAA GGA AAA ATG GTA ACC ATC GAT GGT GCA    594
Asp Trp Val Pro Asp Ala Gln Gly Lys Met Val Thr Ile Asp Gly Ala
                155                 160                 165

CAA TAT AAG ATT TTC CAA ATG GAT CAC ACT GGT CCA ACT ATC AAT GGT    642
Gln Tyr Lys Ile Phe Gln Met Asp His Thr Gly Pro Thr Ile Asn Gly
            170                 175                 180

GGT AAT GAA ACC TTT AAG CAA TAC TTC AGT GTC CGT CAA CAA AAG AGA    690
Gly Asn Glu Thr Phe Lys Gln Tyr Phe Ser Val Arg Gln Gln Lys Arg
        185                 190                 195

ACT TCT GGT CAT ATT ACT GTA TCA GAT CAC TTT AAG GCA TGG TCC AAT    738
Thr Ser Gly His Ile Thr Val Ser Asp His Phe Lys Ala Trp Ser Asn
    200                 205                 210

CAA GGT TGG GGT ATT GGA AAC CTC TAT GAA GTT GCA TTG AAC GCA GAA    786
```

TABLE 13-continued cDNA sequence for xylanase of Orpinomyces Strain
PC-2. See also SEQ ID NO:25 and 26

| | | | | | | | | | | | | | | |
|---|---|---|---|---|---|---|---|---|---|---|---|---|---|---|
| Gln | Gly | Trp | Gly | Ile | Gly | Asn | Leu | Tyr | Glu | Val | Ala | Leu | Asn | Ala | Glu |
| 215 | | | | 220 | | | | 225 | | | | 230 | | | |

| GGT | TGG | CAA | AGT | AGT | GGT | GTC | GCT | GAC | GTC | CCC | AAG | TTG | GAT | GTC | TAC | 834 |
|---|---|---|---|---|---|---|---|---|---|---|---|---|---|---|---|---|
| Gly | Trp | Gln | Ser | Ser | Gly | Val | Ala | Asp | Val | Pro | Lys | Leu | Asp | Val | Tyr | |
| | | | | 235 | | | | 240 | | | | 245 | | | | |

| ACC | ACC | AAA | CAA | GGT | TCT | GCT | CCT | CGT | ACT | ACC | ACC | ACT | ACC | CGT | 882 |
|---|---|---|---|---|---|---|---|---|---|---|---|---|---|---|---|
| Thr | Thr | Lys | Gln | Gly | Ser | Ala | Pro | Arg | Thr | Thr | Thr | Thr | Thr | Arg | |
| | | | 250 | | | | 255 | | | | | 260 | | | |

| ACT | ACT | ACC | CGT | ACT | ACT | ACA | AAA | ACA | CTT | CCA | ACC | ACT | AAT | AAA | AAA | 930 |
|---|---|---|---|---|---|---|---|---|---|---|---|---|---|---|---|---|
| Thr | Thr | Thr | Arg | Thr | Thr | Thr | Lys | Thr | Leu | Pro | Thr | Thr | Asn | Lys | Lys | |
| | | 265 | | | | 270 | | | | | 275 | | | | | |

| TGT | TCT | GCC | AAG | ATT | ACT | GCC | CAA | GGT | TAC | AAG | TGT | TGT | AGT | GAT | CCA | 978 |
|---|---|---|---|---|---|---|---|---|---|---|---|---|---|---|---|---|
| Cys | Ser | Ala | Lys | Ile | Thr | Ala | Gln | Gly | Tyr | Lys | Cys | Cys | Ser | Asp | Pro | |
| 280 | | | | 285 | | | | 290 | | | | | | | | |

| AAT | TGT | GTT | GTT | TAC | TAC | ACT | GAT | GAA | GAT | GGT | ACC | TGG | GGT | GTT | GAA | 1026 |
|---|---|---|---|---|---|---|---|---|---|---|---|---|---|---|---|---|
| Asn | Cys | Val | Val | Tyr | Tyr | Thr | Asp | Glu | Asp | Gly | Thr | Trp | Gly | Val | Glu | |
| 295 | | | | 300 | | | | 305 | | | | | | | 310 | |

| AAC | AAT | CAA | TGG | TGT | GGA | TGT | GGT | GTT | GAA | GCA | TGT | TCT | GGC | AAG | ATT | 1074 |
|---|---|---|---|---|---|---|---|---|---|---|---|---|---|---|---|---|
| Asn | Asn | Gln | Trp | Cys | Gly | Cys | Gly | Val | Glu | Ala | Cys | Ser | Gly | Lys | Ile | |
| | | | | 315 | | | | 320 | | | | | 325 | | | |

| ACT | GCC | CAA | GGT | TAC | AAG | TGT | TGT | AGT | GAT | CCA | AAG | TGT | GTT | GTT | TAC | 1122 |
|---|---|---|---|---|---|---|---|---|---|---|---|---|---|---|---|---|
| Thr | Ala | Gln | Gly | Tyr | Lys | Cys | Cys | Ser | Asp | Pro | Lys | Cys | Val | Val | Tyr | |
| | | 330 | | | | | 335 | | | | | 340 | | | | |

| TAC | ACT | GAT | GAC | GAT | GGT | AAA | TGG | GGT | GTT | GAA | AAC | AAC | GAA | TGG | TGT | 1170 |
|---|---|---|---|---|---|---|---|---|---|---|---|---|---|---|---|---|
| Tyr | Thr | Asp | Asp | Asp | Gly | Lys | Trp | Gly | Val | Glu | Asn | Asn | Glu | Trp | Cys | |
| | | | 345 | | | | 350 | | | | 355 | | | | | |

| GGT | TGT | GGT | TTA | TAA | GCAGAAAAAT | ACTAATTTAG | TAAAAAAAA | AAAAA | 1221 |
|---|---|---|---|---|---|---|---|---|---|
| Gly | Cys | Gly | Leu | | | | | | |
| | | 360 | | | | | | | |

What is claimed is:

1. A method for increasing free ferulic acid content of a plant-derived composition, said method comprising the step of contacting a plant-derived composition with a phenolic acid esterase wherein said phenolic acid esterase comprises the amino acid sequence of SEQ ID NO:18, amino acids 1 to 530 or wherein the phenolic acid esterase consists of an amino acid sequence selected from the group consisting of amino acids 795 to 1077 of SEQ ID NO:12, amino acids 546 to 789 of SEQ ID NO:16, amino acids 20 to 286 of SEQ ID NO:14, amino acids 20 to 307 of SEQ ID NO:14, and amino acids 20 to 421 of SEQ ID NO:14.

2. The method of claim 1, wherein said phenolic acid esterase is a feruloyl esterase.

3. The method of claim 2, wherein the feruloyl esterase comprises the amino acid sequence of SEQ ID NO:18, amino acids 1 to 530.

4. The method of claim 2, wherein the feruloyl esterase consists of the amino acid sequence of SEQ ID NO:12, amino acids 795 to 1077.

5. The method of claim 2, wherein the feruloyl esterase consists of the amino acid sequence of SEQ ID NO:16, amino acids 546 to 789.

6. The method of claim 2, wherein the feruloyl esterase consists of the amino acid sequence of SEQ ID NO:14, amino acids 20 to 286.

7. The method of claim 2, wherein the feruloyl esterase consists of the amino acid sequence of SEQ ID NO:14, amino acids 20 to 307.

8. The method of claim 2, wherein the feruloyl esterase consists of the amino acid sequence of SEQ ID NO:14, amino acids 20 to 421.

9. The method of claim 1, wherein the plant-derived composition is an edible composition.

10. The method of claim 9, wherein the edible composition is a dry composition.

11. The method of claim 9, wherein the edible composition is a liquid composition.

12. The method of claim 9, further comprising the step of contacting the edible composition with a xylanase.

13. The method of claim 12, wherein the xylanase is derived from Orpinomyces PC-2.

14. The method of claim 13, wherein the phenolic acid esterase comprises the amino acid sequence of SEQ ID NO:18, amino acids 1 to 530.

15. The method of claim 9, wherein the phenolic acid esterase consists of the amino acid sequence of SEQ ID NO:12, amino acids 795 to 1077.

16. The method of claim 9, wherein the phenolic acid esterase consists of the amino acid sequence of SEQ ID NO:16, amino acids 546 to 789.

17. The method of claim 9, wherein the phenolic acid esterase consists of the amino acid sequence of SEQ ID NO:14, amino acids 20 to 286.

18. The method of claim 9, wherein the phenolic acid esterase consists of the amino acid sequence of SEQ ID NO:14, amino acids 20 to 307.

19. The method of claim 9, wherein the phenolic acid esterase consists of the amino acid sequence of SEQ ID NO:14, amino acids 20 to 421.

20. The method of claim 12, wherein the xylanase is derived from Orpinomyces.

21. The method of claim 9, wherein the phenolic acid esterase is present in the edible composition at a ratio of from 0.1 to 200 U/kg dry weight of the edible composition.

22. The method of claim 21, wherein the phenolic acid esterase is present in the edible composition at a ratio of from 20 to 50 U/kg dry weight of the edible composition.

23. The method of claim 12, wherein the xylanase is present in the edible composition at a ratio of from 100 to 25,000 U/kg dry weight of the edible composition.

24. The method of claim 12, wherein the xylanase is present in the edible composition at a ratio of from 500 to 10,000 U/kg dry weight of the edible composition.

25. The method of claim 9, wherein said edible composition is for human consumption.

26. The method of claim 12, wherein edible composition is for animal consumption.

27. The method of claim 26, wherein said edible composition is for porcine, bovine, equine or ovine consumption.

28. The method of claim 1, wherein the plant-derived composition is a pulping composition and wherein a phenolic acid esterase is added to the pulping composition at a ratio of from 0.1 to 200 U/kg dry weight.

29. The method of claim 28, wherein the phenolic acid esterase is added at a ratio of from 10 to 100 U/kg dry weight in the pulping composition.

30. The method of claim 29, wherein the method further comprises the step of contacting the pulping composition with a xylanase at a ratio of from 100 to [about] 25,000 U/kg dry weight of plant-derived composition in the pulping composition.

31. The method of claim 30, wherein the xylanase is added at a ratio of from 500 to 10,000 U/kg dry weight in the pulping composition.

32. The method of claim 28, wherein the phenolic acid esterase is a ferulic acid esterase.

33. The method of claim 30, wherein the xylanase is a xylanase of an Orpinomyces species.

34. The method of claim 33, wherein the phenolic acid esterase comprises an amino acid sequence as given in SEQ ID NO:18, amino acids 1–530.

35. The method of claim 9, wherein said phenolic acid esterase is a feruloyl esterase derived from Orpinomyces PC-2, *Clostridium thermocellum*, or a Ruminococcus species.

36. The method of claim 9, wherein the phenolic acid esterase is derived from Trichoderma, Streptomyces, Bacillus, Aureobasidium, Penicillium, Neocallimastix or Humicola.

* * * * *

SEQUENCE LISTING

<160> NUMBER OF SEQ ID NOS: 26

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:
     oligonucleotide used in polymerase chain reaction.

<400> SEQUENCE: 1
taggatcccc tgtagcagaa aatccttc                                        28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:
     oligonucleotide used in polymerase chain reaction.

<400> SEQUENCE: 2
tacatatgcc tgtagcagaa aatccttc                                        28

<210> SEQ ID NO 3

```
<211> LENGTH: 32
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 3
gaggaagctt ttacatggaa gaaatatgga ag                              32

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 4
tacatatgct tgtcacaata agcagtaca                                  29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 5
taggatccct tgtcacaata agcagtaca                                  29

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 6
gaggaagctt ttagttgttg gcaacgcaat a                               31

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 7
gaggaagctt acttccacac attaaaatc                                  29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 8
gaggaagctt agtttccatc cctcgtcaa                                  29

<210> SEQ ID NO 9
<211> LENGTH: 29
```

```
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 9
gaggaagctt agtcataatc ttccgcttc                                          29

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 10
gaggaagctt aaacgccaaa agtgaaccag tc                                      32

<210> SEQ ID NO 11
<211> LENGTH: 3507
<212> TYPE: DNA
<213> ORGANISM: Clostridium thermocellum
<220> FEATURE:
<221> NAME/KEY: CDS
<222> LOCATION: (200)..(3430)

<400> SEQUENCE: 11
taagaaactt taaaacaccc tttataaaaa tacaaagaat tacaggcaat tatagtgtaa         60
tgtggatttt aactaaaatg gaaggaggaa tgtaattcgt aatagatatt atgatataat        120
ttgtttagag catgcttaag tttatttaaa tttaattat aaattaaatt aaaaattaaa        180
atttaaaagg aggttgctt atg aaa aac aag aga gtt ttg gca aaa ata acg        232
                     Met Lys Asn Lys Arg Val Leu Ala Lys Ile Thr
                       1               5                  10 gct ctt gtg gta ttg ctg gga gtg ttt ttt gta tta ccg tca aac ata         280
Ala Leu Val Val Leu Leu Gly Val Phe Phe Val Leu Pro Ser Asn Ile
             15                  20                  25 agt cag cta tat gct gat tat gaa gtg gtt cat gac act ttt gaa gtt         328
Ser Gln Leu Tyr Ala Asp Tyr Glu Val Val His Asp Thr Phe Glu Val
         30                  35                  40 aac ttt gac gga tgg tgt aac ttg gga gtc gac aca tat tta acg gca         376
Asn Phe Asp Gly Trp Cys Asn Leu Gly Val Asp Thr Tyr Leu Thr Ala
     45                  50                  55 gtt gaa aat gaa gga aac aac ggt aca aga ggt atg atg gta ata aat         424
Val Glu Asn Glu Gly Asn Asn Gly Thr Arg Gly Met Met Val Ile Asn
 60                  65                  70                  75 cgc tcc agt gcg agt gac ggt gcg tat tcg gaa aaa ggt ttc tat ctc         472
Arg Ser Ser Ala Ser Asp Gly Ala Tyr Ser Glu Lys Gly Phe Tyr Leu
                 80                  85                  90 gac ggt ggt gta gaa tac aag tac agt gtt ttt gta aaa cac aac ggg         520
Asp Gly Gly Val Glu Tyr Lys Tyr Ser Val Phe Val Lys His Asn Gly
             95                 100                 105 acc ggc acc gaa act ttc aaa ctt tct gtg tcc tat ttg gat tcg gaa         568
Thr Gly Thr Glu Thr Phe Lys Leu Ser Val Ser Tyr Leu Asp Ser Glu
        110                 115                 120 aca gaa gaa gaa aat aag gaa gta att gca aca aag gat gtt gtg gcc         616
Thr Glu Glu Glu Asn Lys Glu Val Ile Ala Thr Lys Asp Val Val Ala
    125                 130                 135 gga gaa tgg act gag att tcg gca aaa tac aaa gca ccc aaa act gca         664
Gly Glu Trp Thr Glu Ile Ser Ala Lys Tyr Lys Ala Pro Lys Thr Ala
140                 145                 150                 155
```

```
gtg aat att act ttg tca att aca acc gac agc act gta gat ttc att      712
Val Asn Ile Thr Leu Ser Ile Thr Thr Asp Ser Thr Val Asp Phe Ile
            160                 165                 170 ttt gac gat gta acc ata acc cgt aaa gga atg gct gag gca aac aca      760
Phe Asp Asp Val Thr Ile Thr Arg Lys Gly Met Ala Glu Ala Asn Thr
                175                 180                 185 gta tat gca gca aac gct gtg ctg aaa gat atg tat gca aac tat ttc      808
Val Tyr Ala Ala Asn Ala Val Leu Lys Asp Met Tyr Ala Asn Tyr Phe
            190                 195                 200 aga gtt ggt tcg gta ctt aac tcc gga acg gta aac aat tca tca ata      856
Arg Val Gly Ser Val Leu Asn Ser Gly Thr Val Asn Asn Ser Ser Ile
        205                 210                 215 aag gcc ttg att tta aga gag ttt aac agt att acc tgt gaa aat gaa      904
Lys Ala Leu Ile Leu Arg Glu Phe Asn Ser Ile Thr Cys Glu Asn Glu
220                 225                 230                 235 atg aag cct gat gcc aca ctg gtt caa tca gga tca acc aat aca aat      952
Met Lys Pro Asp Ala Thr Leu Val Gln Ser Gly Ser Thr Asn Thr Asn
                240                 245                 250 atc agg gtt tct ctt aat cgt gca gca agt att tta aac ttc tgt gca     1000
Ile Arg Val Ser Leu Asn Arg Ala Ala Ser Ile Leu Asn Phe Cys Ala
            255                 260                 265 caa aat aat ata gcc gtc aga ggt cat aca ctg gtt tgg cac agc cag     1048
Gln Asn Asn Ile Ala Val Arg Gly His Thr Leu Val Trp His Ser Gln
        270                 275                 280 aca cct caa tgg ttt ttc aaa gac aat ttc cag gac aac gga aac tgg     1096
Thr Pro Gln Trp Phe Phe Lys Asp Asn Phe Gln Asp Asn Gly Asn Trp
    285                 290                 295 gtt tcc caa tca gtt atg gac cag cgt ttg gaa agc tac ata aaa aat     1144
Val Ser Gln Ser Val Met Asp Gln Arg Leu Glu Ser Tyr Ile Lys Asn
300                 305                 310                 315 atg ttt gct gaa atc caa aga cag tat ccg tct ttg aat ctt tat gcc     1192
Met Phe Ala Glu Ile Gln Arg Gln Tyr Pro Ser Leu Asn Leu Tyr Ala
                320                 325                 330 tat gac gtt gta aat gag gca gta agt gat gat gca aac agg acc aga     1240
Tyr Asp Val Val Asn Glu Ala Val Ser Asp Asp Ala Asn Arg Thr Arg
            335                 340                 345 tat tat ggc ggg gcg agg gaa cct gga tac gga aat ggt aga tct cca     1288
Tyr Tyr Gly Gly Ala Arg Glu Pro Gly Tyr Gly Asn Gly Arg Ser Pro
        350                 355                 360 tgg gtt cag atc tac gga gac aac aaa ttt att gag aaa gca ttt aca     1336
Trp Val Gln Ile Tyr Gly Asp Asn Lys Phe Ile Glu Lys Ala Phe Thr
    365                 370                 375 tat gca aga aaa tat gct ccg gca aat tgt aag ctt tac tac aac gat     1384
Tyr Ala Arg Lys Tyr Ala Pro Ala Asn Cys Lys Leu Tyr Tyr Asn Asp
380                 385                 390                 395 tac aac gaa tat tgg gat cat aag aga gac tgt att gcc tca att tgt     1432
Tyr Asn Glu Tyr Trp Asp His Lys Arg Asp Cys Ile Ala Ser Ile Cys
                400                 405                 410 gca aac ttg tac aac aag ggc ttg ctt gac ggt gtg gga atg cag tcc     1480
Ala Asn Leu Tyr Asn Lys Gly Leu Leu Asp Gly Val Gly Met Gln Ser
            415                 420                 425 cat att aat gcg gat atg aat gga ttc tca ggt ata caa aat tat aaa     1528
His Ile Asn Ala Asp Met Asn Gly Phe Ser Gly Ile Gln Asn Tyr Lys
        430                 435                 440 gca gct ttg cag aaa tat ata aat atc ggt tgt gat gtc caa att acc     1576
Ala Ala Leu Gln Lys Tyr Ile Asn Ile Gly Cys Asp Val Gln Ile Thr
    445                 450                 455 gag ctt gat att agt aca gaa aac ggc aaa ttt agc tta cag cag cag     1624
Glu Leu Asp Ile Ser Thr Glu Asn Gly Lys Phe Ser Leu Gln Gln Gln
```

```
                460                 465                 470                 475
gct gat aaa tat aaa gct gtt ttc cag gca gct gtt gat ata aac aga       1672
Ala Asp Lys Tyr Lys Ala Val Phe Gln Ala Ala Val Asp Ile Asn Arg
                480                 485                 490 acc tcc agc aaa gga aag gtt acg gct gtc tgt gta tgg gga cct aat       1720
Thr Ser Ser Lys Gly Lys Val Thr Ala Val Cys Val Trp Gly Pro Asn
            495                 500                 505 gac gcc aat act tgg ctc ggt tca caa aat gca cct ctt ttg ttt aac       1768
Asp Ala Asn Thr Trp Leu Gly Ser Gln Asn Ala Pro Leu Leu Phe Asn
        510                 515                 520 gca aac aat caa ccg aaa ccg gca tac aat gcg gtt gca tcc att att       1816
Ala Asn Asn Gln Pro Lys Pro Ala Tyr Asn Ala Val Ala Ser Ile Ile
    525                 530                 535 cct cag tcc gaa tgg ggc gac ggt aac aat ccg gcc ggc ggc gga gga       1864
Pro Gln Ser Glu Trp Gly Asp Gly Asn Asn Pro Ala Gly Gly Gly Gly
540                 545                 550                 555 gga ggc aaa ccg gaa gag ccg gat gca aac gga tat tat tat cat gac       1912
Gly Gly Lys Pro Glu Glu Pro Asp Ala Asn Gly Tyr Tyr Tyr His Asp
                560                 565                 570 act ttt gaa gga agc gta gga cag tgg aca gcc aga gga cct gcg gaa       1960
Thr Phe Glu Gly Ser Val Gly Gln Trp Thr Ala Arg Gly Pro Ala Glu
            575                 580                 585 gtt ctg ctt agc gga aga acg gct tac aaa ggt tca gaa tca ctc ttg       2008
Val Leu Leu Ser Gly Arg Thr Ala Tyr Lys Gly Ser Glu Ser Leu Leu
        590                 595                 600 gta agg aac cgt acg gca gca tgg aac gga gca caa cgg gcg ctg aat       2056
Val Arg Asn Arg Thr Ala Ala Trp Asn Gly Ala Gln Arg Ala Leu Asn
    605                 610                 615 ccc aga acg ttt gtt ccc gga aac aca tat tgt ttc agc gta gtg gca       2104
Pro Arg Thr Phe Val Pro Gly Asn Thr Tyr Cys Phe Ser Val Val Ala
620                 625                 630                 635 tcg ttt att gaa ggt gcg tct tcc aca aca ttc tgc atg aag ctg caa       2152
Ser Phe Ile Glu Gly Ala Ser Ser Thr Thr Phe Cys Met Lys Leu Gln
                640                 645                 650 tac gta gac gga agc ggc act caa cgg tat gat acc ata gat atg aaa       2200
Tyr Val Asp Gly Ser Gly Thr Gln Arg Tyr Asp Thr Ile Asp Met Lys
            655                 660                 665 act gtg ggt cca aat cag tgg gtt cac ctg tac aat ccg caa tac aga       2248
Thr Val Gly Pro Asn Gln Trp Val His Leu Tyr Asn Pro Gln Tyr Arg
        670                 675                 680 att cct tcc gat gca aca gat atg tat gtt tat gtg gaa aca gcg gat       2296
Ile Pro Ser Asp Ala Thr Asp Met Tyr Val Tyr Val Glu Thr Ala Asp
    685                 690                 695 gac acc att aac ttc tac ata gat gag gca atc gga gcg gtt gcc gga       2344
Asp Thr Ile Asn Phe Tyr Ile Asp Glu Ala Ile Gly Ala Val Ala Gly
700                 705                 710                 715 act gta atc gaa gga cct gct cca cag cct aca cag cct ccg gta ctg       2392
Thr Val Ile Glu Gly Pro Ala Pro Gln Pro Thr Gln Pro Pro Val Leu
                720                 725                 730 ctt ggc gat gta aac ggt gat gga acc att aac tca act gac ttg aca       2440
Leu Gly Asp Val Asn Gly Asp Gly Thr Ile Asn Ser Thr Asp Leu Thr
            735                 740                 745 atg tta aag aga agc gtg ttg agg gca atc acc ctt acc gac gat gca       2488
Met Leu Lys Arg Ser Val Leu Arg Ala Ile Thr Leu Thr Asp Asp Ala
        750                 755                 760 aag gct aga gca gac gtt gac aag aat gga tcg ata aac agc act gat       2536
Lys Ala Arg Ala Asp Val Asp Lys Asn Gly Ser Ile Asn Ser Thr Asp
    765                 770                 775 gtt tta ctt ctt tca cgc tac ctt tta aga gta atc gac aaa ttt cct       2584
```

-continued

| | | | | | | | | | | | | | |
|---|---|---|---|---|---|---|---|---|---|---|---|---|---|
| Val | Leu | Leu | Leu | Ser | Arg | Tyr | Leu | Leu | Arg | Val | Ile | Asp | Lys | Phe | Pro |
| 780 | | | | | 785 | | | | 790 | | | | | 795 |

```
gta gca gaa aat cct tct tct tct ttt aaa tat gag tcg gcc gtg caa        2632
Val Ala Glu Asn Pro Ser Ser Ser Phe Lys Tyr Glu Ser Ala Val Gln
            800                 805                 810 tat cgg ccg gct cct gat tct tat tta aac cct tgt ccg cag gcg gga        2680
Tyr Arg Pro Ala Pro Asp Ser Tyr Leu Asn Pro Cys Pro Gln Ala Gly
                815                 820                 825 aga att gtc aag gaa aca tat aca gga ata aac gga act aag agt ctt        2728
Arg Ile Val Lys Glu Thr Tyr Thr Gly Ile Asn Gly Thr Lys Ser Leu
            830                 835                 840 aat gta tat ctt cca tac ggt tat gat ccg aac aaa aaa tat aac att        2776
Asn Val Tyr Leu Pro Tyr Gly Tyr Asp Pro Asn Lys Lys Tyr Asn Ile
        845                 850                 855 ttc tac ctt atg cat ggc ggc ggt gaa aat gag aat acg att ttc agc        2824
Phe Tyr Leu Met His Gly Gly Gly Glu Asn Glu Asn Thr Ile Phe Ser
860                 865                 870                 875 aac gat gtt aaa ttg caa aat atc ctt gac cac gcg att atg aac ggt        2872
Asn Asp Val Lys Leu Gln Asn Ile Leu Asp His Ala Ile Met Asn Gly
                880                 885                 890 gaa ctt gag cct ttg att gta gta aca ccc act ttc aac ggc gga aac        2920
Glu Leu Glu Pro Leu Ile Val Val Thr Pro Thr Phe Asn Gly Gly Asn
            895                 900                 905 tgc acg gcc caa aac ttt tat cag gaa ttc agg caa aat gtc att cct        2968
Cys Thr Ala Gln Asn Phe Tyr Gln Glu Phe Arg Gln Asn Val Ile Pro
            910                 915                 920 ttt gtg gaa agc aag tac tct act tat gca gaa tca aca acc cca cag        3016
Phe Val Glu Ser Lys Tyr Ser Thr Tyr Ala Glu Ser Thr Thr Pro Gln
    925                 930                 935 gga ata gcc gct tca aga atg cac aga ggt ttc ggc gga ttc tca atg        3064
Gly Ile Ala Ala Ser Arg Met His Arg Gly Phe Gly Gly Phe Ser Met
940                 945                 950                 955 gga gga ttg aca aca tgg tat gta atg gtt aac tgc ctt gat tac gtt        3112
Gly Gly Leu Thr Thr Trp Tyr Val Met Val Asn Cys Leu Asp Tyr Val
                960                 965                 970 gca tat ttt atg cct tta agc ggt gac tac tgg tat gga aac agt ccg        3160
Ala Tyr Phe Met Pro Leu Ser Gly Asp Tyr Trp Tyr Gly Asn Ser Pro
            975                 980                 985 cag gat aag gct aat tca att gct gaa gca att aac aga tcc gga ctt        3208
Gln Asp Lys Ala Asn Ser Ile Ala Glu Ala Ile Asn Arg Ser Gly Leu
        990                 995                 1000 tca aag agg gag tat ttc gta ttt gcg gcc acc ggt tcc gac cat att        3256
Ser Lys Arg Glu Tyr Phe Val Phe Ala Ala Thr Gly Ser Asp His Ile
    1005                1010                1015 gca tat gct aat atg aat cct caa att gaa gct atg aag gct ttg ccg        3304
Ala Tyr Ala Asn Met Asn Pro Gln Ile Glu Ala Met Lys Ala Leu Pro
1020                1025                1030                1035 cat ttt gat tat act tcg gat ttt tcc aaa ggt aat ttt tac ttt ctt        3352
His Phe Asp Tyr Thr Ser Asp Phe Ser Lys Gly Asn Phe Tyr Phe Leu
                1040                1045                1050 gta gct ccg ggc gcc act cac tgg tgg gga tac gta aga cat tat att        3400
Val Ala Pro Gly Ala Thr His Trp Trp Gly Tyr Val Arg His Tyr Ile
            1055                1060                1065 tat gat gca ctt cca tat ttc ttc cat gaa tgaatgagaa agaaaaacat         3450
Tyr Asp Ala Leu Pro Tyr Phe Phe His Glu
        1070                1075 gattgagttt gtaatcaata aaaaaggaa ttttttagtg gtgtccaggt tattgaa           3507
```

<210> SEQ ID NO 12

```
<211> LENGTH: 1077
<212> TYPE: PRT
<213> ORGANISM: Clostridium thermocellum

<400> SEQUENCE: 12

Met Lys Asn Lys Arg Val Leu Ala Lys Ile Thr Ala Leu Val Val Leu
 1               5                  10                  15

Leu Gly Val Phe Phe Val Leu Pro Ser Asn Ile Ser Gln Leu Tyr Ala
             20                  25                  30

Asp Tyr Glu Val Val His Asp Thr Phe Glu Val Asn Phe Asp Gly Trp
         35                  40                  45

Cys Asn Leu Gly Val Asp Thr Tyr Leu Thr Ala Val Glu Asn Glu Gly
     50                  55                  60

Asn Asn Gly Thr Arg Gly Met Met Val Ile Asn Arg Ser Ser Ala Ser
 65                  70                  75                  80

Asp Gly Ala Tyr Ser Glu Lys Gly Phe Tyr Leu Asp Gly Gly Val Glu
                 85                  90                  95

Tyr Lys Tyr Ser Val Phe Val Lys His Asn Gly Thr Gly Thr Glu Thr
            100                 105                 110

Phe Lys Leu Ser Val Ser Tyr Leu Asp Ser Glu Thr Glu Glu Glu Asn
        115                 120                 125

Lys Glu Val Ile Ala Thr Lys Asp Val Val Ala Gly Glu Trp Thr Glu
130                 135                 140

Ile Ser Ala Lys Tyr Lys Ala Pro Lys Thr Ala Val Asn Ile Thr Leu
145                 150                 155                 160

Ser Ile Thr Thr Asp Ser Thr Val Asp Phe Ile Phe Asp Asp Val Thr
                165                 170                 175

Ile Thr Arg Lys Gly Met Ala Glu Ala Asn Thr Val Tyr Ala Ala Asn
            180                 185                 190

Ala Val Leu Lys Asp Met Tyr Ala Asn Tyr Phe Arg Val Gly Ser Val
        195                 200                 205

Leu Asn Ser Gly Thr Val Asn Asn Ser Ser Ile Lys Ala Leu Ile Leu
    210                 215                 220

Arg Glu Phe Asn Ser Ile Thr Cys Glu Asn Glu Met Lys Pro Asp Ala
225                 230                 235                 240

Thr Leu Val Gln Ser Gly Ser Thr Asn Thr Asn Ile Arg Val Ser Leu
                245                 250                 255

Asn Arg Ala Ala Ser Ile Leu Asn Phe Cys Ala Gln Asn Asn Ile Ala
            260                 265                 270

Val Arg Gly His Thr Leu Val Trp His Ser Gln Thr Pro Gln Trp Phe
        275                 280                 285

Phe Lys Asp Asn Phe Gln Asp Asn Gly Asn Trp Val Ser Gln Ser Val
    290                 295                 300

Met Asp Gln Arg Leu Glu Ser Tyr Ile Lys Asn Met Phe Ala Glu Ile
305                 310                 315                 320

Gln Arg Gln Tyr Pro Ser Leu Asn Leu Tyr Ala Tyr Asp Val Val Asn
                325                 330                 335

Glu Ala Val Ser Asp Asp Ala Asn Arg Thr Arg Tyr Tyr Gly Gly Ala
            340                 345                 350

Arg Glu Pro Gly Tyr Gly Asn Gly Arg Ser Pro Trp Val Gln Ile Tyr
        355                 360                 365

Gly Asp Asn Lys Phe Ile Glu Lys Ala Phe Thr Tyr Ala Arg Lys Tyr
    370                 375                 380

Ala Pro Ala Asn Cys Lys Leu Tyr Tyr Asn Asp Tyr Asn Glu Tyr Trp
```

-continued

```
385                 390                 395                 400

Asp His Lys Arg Asp Cys Ile Ala Ser Ile Cys Ala Asn Leu Tyr Asn
                405                 410                 415

Lys Gly Leu Leu Asp Gly Val Gly Met Gln Ser His Ile Asn Ala Asp
            420                 425                 430

Met Asn Gly Phe Ser Gly Ile Gln Asn Tyr Lys Ala Ala Leu Gln Lys
            435                 440                 445

Tyr Ile Asn Ile Gly Cys Asp Val Gln Ile Thr Glu Leu Asp Ile Ser
        450                 455                 460

Thr Glu Asn Gly Lys Phe Ser Leu Gln Gln Ala Asp Lys Tyr Lys
465                 470                 475                 480

Ala Val Phe Gln Ala Ala Val Asp Ile Asn Arg Thr Ser Ser Lys Gly
                485                 490                 495

Lys Val Thr Ala Val Cys Val Trp Gly Pro Asn Asp Ala Asn Thr Trp
            500                 505                 510

Leu Gly Ser Gln Asn Ala Pro Leu Leu Phe Asn Ala Asn Asn Gln Pro
        515                 520                 525

Lys Pro Ala Tyr Asn Ala Val Ala Ser Ile Ile Pro Gln Ser Glu Trp
        530                 535                 540

Gly Asp Gly Asn Asn Pro Ala Gly Gly Gly Gly Gly Lys Pro Glu
545                 550                 555                 560

Glu Pro Asp Ala Asn Gly Tyr Tyr His Asp Thr Phe Glu Gly Ser
                565                 570                 575

Val Gly Gln Trp Thr Ala Arg Gly Pro Ala Glu Val Leu Leu Ser Gly
            580                 585                 590

Arg Thr Ala Tyr Lys Gly Ser Glu Ser Leu Leu Val Arg Asn Arg Thr
        595                 600                 605

Ala Ala Trp Asn Gly Ala Gln Arg Ala Leu Asn Pro Arg Thr Phe Val
    610                 615                 620

Pro Gly Asn Thr Tyr Cys Phe Ser Val Val Ala Ser Phe Ile Glu Gly
625                 630                 635                 640

Ala Ser Ser Thr Thr Phe Cys Met Lys Leu Gln Tyr Val Asp Gly Ser
                645                 650                 655

Gly Thr Gln Arg Tyr Asp Thr Ile Asp Met Lys Thr Val Gly Pro Asn
            660                 665                 670

Gln Trp Val His Leu Tyr Asn Pro Gln Tyr Arg Ile Pro Ser Asp Ala
        675                 680                 685

Thr Asp Met Tyr Val Tyr Val Glu Thr Ala Asp Asp Thr Ile Asn Phe
    690                 695                 700

Tyr Ile Asp Glu Ala Ile Gly Ala Val Ala Gly Thr Val Ile Glu Gly
705                 710                 715                 720

Pro Ala Pro Gln Pro Thr Gln Pro Val Leu Leu Gly Asp Val Asn
                725                 730                 735

Gly Asp Gly Thr Ile Asn Ser Thr Asp Leu Thr Met Leu Lys Arg Ser
            740                 745                 750

Val Leu Arg Ala Ile Thr Leu Thr Asp Ala Lys Ala Arg Ala Asp
        755                 760                 765

Val Asp Lys Asn Gly Ser Ile Asn Ser Thr Asp Val Leu Leu Leu Ser
    770                 775                 780

Arg Tyr Leu Leu Arg Val Ile Asp Lys Phe Pro Val Ala Glu Asn Pro
785                 790                 795                 800

Ser Ser Ser Phe Lys Tyr Glu Ser Ala Val Gln Tyr Arg Pro Ala Pro
                805                 810                 815
```

-continued

```
Asp Ser Tyr Leu Asn Pro Cys Pro Gln Ala Gly Arg Ile Val Lys Glu
        820                 825                 830
Thr Tyr Thr Gly Ile Asn Gly Thr Lys Ser Leu Asn Val Tyr Leu Pro
        835                 840                 845
Tyr Gly Tyr Asp Pro Asn Lys Lys Tyr Asn Ile Phe Tyr Leu Met His
    850                 855                 860
Gly Gly Gly Glu Asn Glu Asn Thr Ile Phe Ser Asn Asp Val Lys Leu
865                 870                 875                 880
Gln Asn Ile Leu Asp His Ala Ile Met Asn Gly Glu Leu Glu Pro Leu
                885                 890                 895
Ile Val Val Thr Pro Thr Phe Asn Gly Gly Asn Cys Thr Ala Gln Asn
                900                 905                 910
Phe Tyr Gln Glu Phe Arg Gln Asn Val Ile Pro Phe Val Glu Ser Lys
            915                 920                 925
Tyr Ser Thr Tyr Ala Glu Ser Thr Thr Pro Gln Gly Ile Ala Ala Ser
    930                 935                 940
Arg Met His Arg Gly Phe Gly Phe Ser Met Gly Gly Leu Thr Thr
945                 950                 955                 960
Trp Tyr Val Met Val Asn Cys Leu Asp Tyr Val Ala Tyr Phe Met Pro
                965                 970                 975
Leu Ser Gly Asp Tyr Trp Tyr Gly Asn Ser Pro Gln Asp Lys Ala Asn
            980                 985                 990
Ser Ile Ala Glu Ala Ile Asn Arg Ser Gly Leu Ser Lys Arg Glu Tyr
        995                 1000                1005
Phe Val Phe Ala Ala Thr Gly Ser Asp His Ile Ala Tyr Ala Asn Met
    1010                1015                1020
Asn Pro Gln Ile Glu Ala Met Lys Ala Leu Pro His Phe Asp Tyr Thr
1025                1030                1035                1040
Ser Asp Phe Ser Lys Gly Asn Phe Tyr Phe Leu Val Ala Pro Gly Ala
                1045                1050                1055
Thr His Trp Trp Gly Tyr Val Arg His Tyr Ile Tyr Asp Ala Leu Pro
            1060                1065                1070
Tyr Phe Phe His Glu
        1075
```

<210> SEQ ID NO 13
<211> LENGTH: 2722
<212> TYPE: DNA
<213> ORGANISM: Clostridium thermocellum
<220> FEATURE:
<221> NAME/KEY: CDS
<222> LOCATION: (101)..(2611)

<400> SEQUENCE: 13

```
atatataaat aagggtatta attctgcaaa aagaaaagtg tttgctacat gaggtccatt      60 aattttatt  ttatatcata aatcaaaaag gaggagaaac atg tca aga aaa ctt     115
                                             Met Ser Arg Lys Leu
                                              1               5 ttc agt gta tta ctt gtt ggc ttg atg ctt atg aca tcg ttg ctt gtc     163
Phe Ser Val Leu Leu Val Gly Leu Met Leu Met Thr Ser Leu Leu Val
             10                  15                  20 aca ata agc agt aca tca gcg gca tcc ttg cca acc atg ccg cct tcg     211
Thr Ile Ser Ser Thr Ser Ala Ala Ser Leu Pro Thr Met Pro Pro Ser
         25                  30                  35 gga tat gac cag gta agg aac ggc gtt ccg aga ggg cag gtc gta aat     259
Gly Tyr Asp Gln Val Arg Asn Gly Val Pro Arg Gly Gln Val Val Asn
```

```
                   40                  45                  50
att tct tat ttc tcc acg gcc acc aac agt acc agg ccg gca aga gtt    307
Ile Ser Tyr Phe Ser Thr Ala Thr Asn Ser Thr Arg Pro Ala Arg Val
         55                  60                  65 tat ttg ccg ccg gga tat tca aag gac aaa aaa tac agt gtt ttg tat    355
Tyr Leu Pro Pro Gly Tyr Ser Lys Asp Lys Lys Tyr Ser Val Leu Tyr
 70                  75                  80                  85 ctc tta cac ggc ata ggc ggt agt gaa aac gac tgg ttc gaa ggg gga    403
Leu Leu His Gly Ile Gly Gly Ser Glu Asn Asp Trp Phe Glu Gly Gly
                 90                  95                 100 ggc aga gcc aat gtt att gcc gac aat ctg att gcc gag gga aaa atc    451
Gly Arg Ala Asn Val Ile Ala Asp Asn Leu Ile Ala Glu Gly Lys Ile
            105                 110                 115 aag ccc ctg ata att gta aca ccg aat act aac gcc gcc ggt ccg gga    499
Lys Pro Leu Ile Ile Val Thr Pro Asn Thr Asn Ala Ala Gly Pro Gly
        120                 125                 130 ata gcg gac ggt tat gaa aat ttc aca aaa gat ttg ctc aac agt ctt    547
Ile Ala Asp Gly Tyr Glu Asn Phe Thr Lys Asp Leu Leu Asn Ser Leu
    135                 140                 145 att ccc tat atc gaa tct aac tat tca gtc tac acc gac cgc gaa cat    595
Ile Pro Tyr Ile Glu Ser Asn Tyr Ser Val Tyr Thr Asp Arg Glu His
150                 155                 160                 165 cgg gcg att gca gga ctt tca atg ggt gga gga caa tcg ttt aat att    643
Arg Ala Ile Ala Gly Leu Ser Met Gly Gly Gly Gln Ser Phe Asn Ile
                170                 175                 180 gga ttg acc aat ctc gat aaa ttt gcc tat att ggc ccg att tca gcg    691
Gly Leu Thr Asn Leu Asp Lys Phe Ala Tyr Ile Gly Pro Ile Ser Ala
            185                 190                 195 gct cca aac act tat cca aat gag agg ctt ttt cct gac gga gga aaa    739
Ala Pro Asn Thr Tyr Pro Asn Glu Arg Leu Phe Pro Asp Gly Gly Lys
        200                 205                 210 gct gca agg gag aaa ttg aaa ctg ctc ttt att gcc tgc gga acc aat    787
Ala Ala Arg Glu Lys Leu Lys Leu Leu Phe Ile Ala Cys Gly Thr Asn
    215                 220                 225 gac agt ctg ata ggt ttt gga cag aga gta cat gaa tat tgc gtt gcc    835
Asp Ser Leu Ile Gly Phe Gly Gln Arg Val His Glu Tyr Cys Val Ala
230                 235                 240                 245 aac aac att aac cat gtc tat tgg ctt att cag ggc gga gga cac gat    883
Asn Asn Ile Asn His Val Tyr Trp Leu Ile Gln Gly Gly Gly His Asp
                250                 255                 260 ttt aat gtg tgg aag ccc gga ttg tgg aat ttc ctt caa atg gca gat    931
Phe Asn Val Trp Lys Pro Gly Leu Trp Asn Phe Leu Gln Met Ala Asp
            265                 270                 275 gaa gcc gga ttg acg agg gat gga aac act ccg gtt ccg aca ccc agt    979
Glu Ala Gly Leu Thr Arg Asp Gly Asn Thr Pro Val Pro Thr Pro Ser
        280                 285                 290 cca aag ccg gct aac aca cgt att gaa gcg gaa gat tat gac ggt att   1027
Pro Lys Pro Ala Asn Thr Arg Ile Glu Ala Glu Asp Tyr Asp Gly Ile
    295                 300                 305 aat tct tca agt att gag ata ata ggt gtt cca cct gaa gga ggc aga   1075
Asn Ser Ser Ser Ile Glu Ile Ile Gly Val Pro Pro Glu Gly Gly Arg
310                 315                 320                 325 gga ata ggt tat att acc agt ggt gat tat ctg gta tac aag agt ata   1123
Gly Ile Gly Tyr Ile Thr Ser Gly Asp Tyr Leu Val Tyr Lys Ser Ile
                330                 335                 340 gac ttt gga aac gga gca acg tcg ttt aag gcc aag gtt gca aat gca   1171
Asp Phe Gly Asn Gly Ala Thr Ser Phe Lys Ala Lys Val Ala Asn Ala
            345                 350                 355 aat act tcc aat att gaa ctt aga tta aac ggt ccg aat ggt act ctc   1219
```

```
Asn Thr Ser Asn Ile Glu Leu Arg Leu Asn Gly Pro Asn Gly Thr Leu
            360                 365                 370 ata ggc aca ctc tcg gta aaa tcc aca gga gat tgg aat aca tat gag        1267
Ile Gly Thr Leu Ser Val Lys Ser Thr Gly Asp Trp Asn Thr Tyr Glu
        375                 380                 385 gag caa act tgc agc att agc aaa gtc acc gga ata aat gat ttg tac        1315
Glu Gln Thr Cys Ser Ile Ser Lys Val Thr Gly Ile Asn Asp Leu Tyr
390                 395                 400                 405 ttg gta ttc aaa ggc cct gta aac ata gac tgg ttc act ttt ggc gtt        1363
Leu Val Phe Lys Gly Pro Val Asn Ile Asp Trp Phe Thr Phe Gly Val
                410                 415                 420 gaa agc agt tcc aca ggt ctg ggg gat tta aat ggt gac gga aat att        1411
Glu Ser Ser Ser Thr Gly Leu Gly Asp Leu Asn Gly Asp Gly Asn Ile
            425                 430                 435 aac tcg tcg gac ctt cag gcg tta aag agg cat ttg ctc ggt ata tca        1459
Asn Ser Ser Asp Leu Gln Ala Leu Lys Arg His Leu Leu Gly Ile Ser
        440                 445                 450 ccg ctt acg gga gag gct ctt tta aga gcg gat gta aat agg agc ggc        1507
Pro Leu Thr Gly Glu Ala Leu Leu Arg Ala Asp Val Asn Arg Ser Gly
    455                 460                 465 aaa gtg gat tct act gac tat tca gtg ctg aaa aga tat ata ctc cgc        1555
Lys Val Asp Ser Thr Asp Tyr Ser Val Leu Lys Arg Tyr Ile Leu Arg
470                 475                 480                 485 att att aca gag ttc ccc gga caa ggt gat gta cag aca ccc aat ccg        1603
Ile Ile Thr Glu Phe Pro Gly Gln Gly Asp Val Gln Thr Pro Asn Pro
                490                 495                 500 tct gtt act ccg aca caa act cct atc ccc acg att tcg gga aat gct        1651
Ser Val Thr Pro Thr Gln Thr Pro Ile Pro Thr Ile Ser Gly Asn Ala
            505                 510                 515 ctt agg gat tat gcg gag gca agg gga ata aaa atc gga aca tgt gtc        1699
Leu Arg Asp Tyr Ala Glu Ala Arg Gly Ile Lys Ile Gly Thr Cys Val
        520                 525                 530 aac tat ccg ttt tac aac aat tca gat cca acc tac aac agc att ttg        1747
Asn Tyr Pro Phe Tyr Asn Asn Ser Asp Pro Thr Tyr Asn Ser Ile Leu
    535                 540                 545 caa aga gaa ttt tca atg gtt gta tgt gaa aat gaa atg aag ttt gat        1795
Gln Arg Glu Phe Ser Met Val Val Cys Glu Asn Glu Met Lys Phe Asp
550                 555                 560                 565 gct ttg cag ccg aga caa aac gtt ttt gat ttt tcg aaa gga gac cag        1843
Ala Leu Gln Pro Arg Gln Asn Val Phe Asp Phe Ser Lys Gly Asp Gln
                570                 575                 580 ttg ctt gct ttt gca gaa aga aac ggt atg cag atg agg gga cat acg        1891
Leu Leu Ala Phe Ala Glu Arg Asn Gly Met Gln Met Arg Gly His Thr
            585                 590                 595 ttg att tgg cac aat caa aac ccg tca tgg ctt aca aac ggt aac tgg        1939
Leu Ile Trp His Asn Gln Asn Pro Ser Trp Leu Thr Asn Gly Asn Trp
        600                 605                 610 aac cgg gat tcg ctg ctt gcg gta atg aaa aat cac att acc act gtt        1987
Asn Arg Asp Ser Leu Leu Ala Val Met Lys Asn His Ile Thr Thr Val
    615                 620                 625 atg acc cat tac aaa ggt aaa att gtt gag tgg gat gtg gca aac gaa        2035
Met Thr His Tyr Lys Gly Lys Ile Val Glu Trp Asp Val Ala Asn Glu
630                 635                 640                 645 tgt atg gat gat tcc ggc aac ggc tta aga agc agc ata tgg aga aat        2083
Cys Met Asp Asp Ser Gly Asn Gly Leu Arg Ser Ser Ile Trp Arg Asn
                650                 655                 660 gta atc ggt cag gac tac ctt gac tat gct ttc agg tat gca aga gaa        2131
Val Ile Gly Gln Asp Tyr Leu Asp Tyr Ala Phe Arg Tyr Ala Arg Glu
            665                 670                 675
```

-continued

```
gca gat ccc gat gca ctt ctt ttc tac aat gat tat aat att gaa gac      2179
Ala Asp Pro Asp Ala Leu Leu Phe Tyr Asn Asp Tyr Asn Ile Glu Asp
            680                 685                 690 ttg ggt cca aag tcc aat gcg gta ttt aac atg att aaa agt atg aag      2227
Leu Gly Pro Lys Ser Asn Ala Val Phe Asn Met Ile Lys Ser Met Lys
695                 700                 705 gaa aga ggt gtg ccg att gac gga gta gga ttc caa tgc cac ttt atc      2275
Glu Arg Gly Val Pro Ile Asp Gly Val Gly Phe Gln Cys His Phe Ile
710                 715                 720                 725 aat gga atg agc ccc gag tac ctt gcc agc att gat caa aat att aag      2323
Asn Gly Met Ser Pro Glu Tyr Leu Ala Ser Ile Asp Gln Asn Ile Lys
            730                 735                 740 aga tat gcg gaa ata ggc gtt ata gta tcc ttt acc gaa ata gat ata      2371
Arg Tyr Ala Glu Ile Gly Val Ile Val Ser Phe Thr Glu Ile Asp Ile
        745                 750                 755 cgc ata cct cag tcg gaa aac ccg gca act gca ttc cag gta cag gca      2419
Arg Ile Pro Gln Ser Glu Asn Pro Ala Thr Ala Phe Gln Val Gln Ala
    760                 765                 770 aac aac tat aag gaa ctt atg aaa att tgt ctg gca aac ccc aat tgc      2467
Asn Asn Tyr Lys Glu Leu Met Lys Ile Cys Leu Ala Asn Pro Asn Cys
775                 780                 785 aat acc ttt gta atg tgg gga ttc aca gat aaa tac aca tgg att ccg      2515
Asn Thr Phe Val Met Trp Gly Phe Thr Asp Lys Tyr Thr Trp Ile Pro
790                 795                 800                 805 gga act ttc cca gga tat ggc aat cca ttg att tat gac agc aat tac      2563
Gly Thr Phe Pro Gly Tyr Gly Asn Pro Leu Ile Tyr Asp Ser Asn Tyr
            810                 815                 820 aat ccg aaa ccg gca tac aat gca ata aag gaa gct ctt atg ggc tat      2611
Asn Pro Lys Pro Ala Tyr Asn Ala Ile Lys Glu Ala Leu Met Gly Tyr
        825                 830                 835 tgataattcc gaaaagctga gcagataatg atgccgtaaa gccggcttct gaattaagag    2671
ccggctttac ggagatatac ttttacggc agaatacctg ttatttccat g              2722
```

<210> SEQ ID NO 14
<211> LENGTH: 837
<212> TYPE: PRT
<213> ORGANISM: Clostridium thermocellum

<400> SEQUENCE: 14

```
Met Ser Arg Lys Leu Phe Ser Val Leu Leu Val Gly Leu Met Leu Met
 1               5                  10                  15

Thr Ser Leu Leu Val Thr Ile Ser Ser Thr Ser Ala Ala Ser Leu Pro
            20                  25                  30

Thr Met Pro Pro Ser Gly Tyr Asp Gln Val Arg Asn Gly Val Pro Arg
        35                  40                  45

Gly Gln Val Val Asn Ile Ser Tyr Phe Ser Thr Ala Thr Asn Ser Thr
    50                  55                  60

Arg Pro Ala Arg Val Tyr Leu Pro Pro Gly Tyr Ser Lys Asp Lys Lys
65                  70                  75                  80

Tyr Ser Val Leu Tyr Leu Leu His Gly Ile Gly Gly Ser Glu Asn Asp
                85                  90                  95

Trp Phe Glu Gly Gly Arg Ala Asn Val Ile Ala Asp Asn Leu Ile
            100                 105                 110

Ala Glu Gly Lys Ile Lys Pro Leu Ile Ile Val Thr Pro Asn Thr Asn
        115                 120                 125

Ala Ala Gly Pro Gly Ile Ala Asp Gly Tyr Glu Asn Phe Thr Lys Asp
    130                 135                 140
```

-continued

```
Leu Leu Asn Ser Leu Ile Pro Tyr Ile Glu Ser Asn Tyr Ser Val Tyr
145                 150                 155                 160

Thr Asp Arg Glu His Arg Ala Ile Ala Gly Leu Ser Met Gly Gly Gly
                165                 170                 175

Gln Ser Phe Asn Ile Gly Leu Thr Asn Leu Asp Lys Phe Ala Tyr Ile
            180                 185                 190

Gly Pro Ile Ser Ala Ala Pro Asn Thr Tyr Pro Asn Glu Arg Leu Phe
        195                 200                 205

Pro Asp Gly Gly Lys Ala Ala Arg Glu Lys Leu Lys Leu Leu Phe Ile
    210                 215                 220

Ala Cys Gly Thr Asn Asp Ser Leu Ile Gly Phe Gly Gln Arg Val His
225                 230                 235                 240

Glu Tyr Cys Val Ala Asn Ile Asn His Val Tyr Trp Leu Ile Gln
                245                 250                 255

Gly Gly Gly His Asp Phe Asn Val Trp Lys Pro Gly Leu Trp Asn Phe
            260                 265                 270

Leu Gln Met Ala Asp Glu Ala Gly Leu Thr Arg Asp Gly Asn Thr Pro
        275                 280                 285

Val Pro Thr Pro Ser Pro Lys Pro Ala Asn Thr Arg Ile Glu Ala Glu
    290                 295                 300

Asp Tyr Asp Gly Ile Asn Ser Ser Ile Glu Ile Gly Val Pro
305                 310                 315                 320

Pro Glu Gly Gly Arg Gly Ile Gly Tyr Ile Thr Ser Gly Asp Tyr Leu
                325                 330                 335

Val Tyr Lys Ser Ile Asp Phe Gly Asn Gly Ala Thr Ser Phe Lys Ala
            340                 345                 350

Lys Val Ala Asn Ala Asn Thr Ser Asn Ile Glu Leu Arg Leu Asn Gly
        355                 360                 365

Pro Asn Gly Thr Leu Ile Gly Thr Leu Ser Val Lys Ser Thr Gly Asp
    370                 375                 380

Trp Asn Thr Tyr Glu Glu Gln Thr Cys Ser Ile Ser Lys Val Thr Gly
385                 390                 395                 400

Ile Asn Asp Leu Tyr Leu Val Phe Lys Gly Pro Val Asn Ile Asp Trp
                405                 410                 415

Phe Thr Phe Gly Val Glu Ser Ser Thr Gly Leu Gly Asp Leu Asn
            420                 425                 430

Gly Asp Gly Asn Ile Asn Ser Ser Asp Leu Gln Ala Leu Lys Arg His
        435                 440                 445

Leu Leu Gly Ile Ser Pro Leu Thr Gly Glu Ala Leu Leu Arg Ala Asp
    450                 455                 460

Val Asn Arg Ser Gly Lys Val Asp Ser Thr Asp Tyr Ser Val Leu Lys
465                 470                 475                 480

Arg Tyr Ile Leu Arg Ile Ile Thr Glu Phe Pro Gly Gln Gly Asp Val
                485                 490                 495

Gln Thr Pro Asn Pro Ser Val Thr Pro Thr Gln Thr Pro Ile Pro Thr
            500                 505                 510

Ile Ser Gly Asn Ala Leu Arg Asp Tyr Ala Glu Ala Arg Gly Ile Lys
        515                 520                 525

Ile Gly Thr Cys Val Asn Tyr Pro Phe Tyr Asn Asn Ser Asp Pro Thr
    530                 535                 540

Tyr Asn Ser Ile Leu Gln Arg Glu Phe Ser Met Val Val Cys Glu Asn
545                 550                 555                 560

Glu Met Lys Phe Asp Ala Leu Gln Pro Arg Gln Asn Val Phe Asp Phe
```

```
                565                   570                   575
Ser Lys Gly Asp Gln Leu Leu Ala Phe Ala Glu Arg Asn Gly Met Gln
                580                   585                   590

Met Arg Gly His Thr Leu Ile Trp His Asn Gln Asn Pro Ser Trp Leu
            595                   600                   605

Thr Asn Gly Asn Trp Asn Arg Asp Ser Leu Leu Ala Val Met Lys Asn
        610                   615                   620

His Ile Thr Thr Val Met Thr His Tyr Lys Gly Lys Ile Val Glu Trp
625                   630                   635                   640

Asp Val Ala Asn Glu Cys Met Asp Ser Gly Asn Gly Leu Arg Ser
                    645                   650                   655

Ser Ile Trp Arg Asn Val Ile Gly Gln Asp Tyr Leu Asp Tyr Ala Phe
                660                   665                   670

Arg Tyr Ala Arg Glu Ala Asp Pro Asp Ala Leu Leu Phe Tyr Asn Asp
            675                   680                   685

Tyr Asn Ile Glu Asp Leu Gly Pro Lys Ser Asn Ala Val Phe Asn Met
        690                   695                   700

Ile Lys Ser Met Lys Glu Arg Gly Val Pro Ile Asp Gly Val Gly Phe
705                   710                   715                   720

Gln Cys His Phe Ile Asn Gly Met Ser Pro Glu Tyr Leu Ala Ser Ile
                    725                   730                   735

Asp Gln Asn Ile Lys Arg Tyr Ala Glu Ile Gly Val Ile Val Ser Phe
                740                   745                   750

Thr Glu Ile Asp Ile Arg Ile Pro Gln Ser Glu Asn Pro Ala Thr Ala
            755                   760                   765

Phe Gln Val Gln Ala Asn Asn Tyr Lys Glu Leu Met Lys Ile Cys Leu
        770                   775                   780

Ala Asn Pro Asn Cys Asn Thr Phe Val Met Trp Gly Phe Thr Asp Lys
785                   790                   795                   800

Tyr Thr Trp Ile Pro Gly Thr Phe Pro Gly Tyr Gly Asn Pro Leu Ile
                    805                   810                   815

Tyr Asp Ser Asn Tyr Asn Pro Lys Pro Ala Tyr Asn Ala Ile Lys Glu
                820                   825                   830

Ala Leu Met Gly Tyr
            835

<210> SEQ ID NO 15
<211> LENGTH: 3105
<212> TYPE: DNA
<213> ORGANISM: Ruminococcus sp.
<220> FEATURE:
<221> NAME/KEY: CDS
<222> LOCATION: (529)..(2895)

<400> SEQUENCE: 15 gatcttttc  ataagtatgc  cccattatt  aagtttttta  gatgcttgcc  tataatttcc      60
cttctggttt  tgtgaacttc  ttaacggtca  gagttcacac  tttctttata  tattgtctat    120
attataatgt  atattgtagt  aataatatac  caaaatttc  ctttaagtaa  caatatcttt    180
accctattta  gcaattttta  acgatatttt  ataatttgat  tattttaaa  ctatacagtg    240 taaatactat  tatttaaaaa  gtccaccaaa  aatgtaaaat  acaatgatat  cttaaacgta    300
aaaacctgta  caatgattgt  tcatcttttt  acattattgt  tatatatcgt  cttggtatag    360
tcagcaattt  ttagtcaaga  tatacaaggt  ccgcaaattt  taacttgcaa  ttaacaggtc    420
agatgtttta  taatgatatc  atagaaataa  aaggagcact  tggctcctta  tggggattac    480
```

-continued

```
tgaaatcata agtttgcttt ttttctaaaa aacaaaggag tgattgaa gtg aaa aaa      537
                                                  Val Lys Lys
                                                    1 aca gtt aaa caa ttc atc agc agt gcc gtt aca gcg tta atg gtg gct      585
Thr Val Lys Gln Phe Ile Ser Ser Ala Val Thr Ala Leu Met Val Ala
      5                  10                  15 gca agc ctg cct gcc gtt cct tcc gtg aac gca gcc gac gcc cag cag      633
Ala Ser Leu Pro Ala Val Pro Ser Val Asn Ala Ala Asp Ala Gln Gln
 20                  25                  30                  35 aga ggc aat atc ggc ggt ttc gat tac gaa atg tgg aac cag aac ggt      681
Arg Gly Asn Ile Gly Gly Phe Asp Tyr Glu Met Trp Asn Gln Asn Gly
                 40                  45                  50 cag gga cag gta tca atg acg cct aag gca ggc tct ttc acc tgc tca      729
Gln Gly Gln Val Ser Met Thr Pro Lys Ala Gly Ser Phe Thr Cys Ser
             55                  60                  65 tgg agc aac att gaa aac ttc ctc gca cgt atg ggc aag aac tac gac      777
Trp Ser Asn Ile Glu Asn Phe Leu Ala Arg Met Gly Lys Asn Tyr Asp
         70                  75                  80 agc cag aaa aag aac tac aag gct ttc gga gac att acc ctc tcc tac      825
Ser Gln Lys Lys Asn Tyr Lys Ala Phe Gly Asp Ile Thr Leu Ser Tyr
     85                  90                  95 gac gta gag tac acc ccc aag ggc aac tct tat atg tgc gta tac ggc      873
Asp Val Glu Tyr Thr Pro Lys Gly Asn Ser Tyr Met Cys Val Tyr Gly
100                 105                 110                 115 tgg acg agg aac cct ctc atg gaa tac tac atc gtc gaa ggc tgg ggc      921
Trp Thr Arg Asn Pro Leu Met Glu Tyr Tyr Ile Val Glu Gly Trp Gly
                120                 125                 130 gac tgg cgt cca ccc gga aat gac ggc gaa aac aag ggt aca gtt acc      969
Asp Trp Arg Pro Pro Gly Asn Asp Gly Glu Asn Lys Gly Thr Val Thr
            135                 140                 145 ctg aac ggc aac acc tac gat atc cgc aaa aca atg cgt tat aat cag     1017
Leu Asn Gly Asn Thr Tyr Asp Ile Arg Lys Thr Met Arg Tyr Asn Gln
        150                 155                 160 cca tct ctg gac ggc acg gct aca ttc cct cag tac tgg agc gta cgt     1065
Pro Ser Leu Asp Gly Thr Ala Thr Phe Pro Gln Tyr Trp Ser Val Arg
    165                 170                 175 cag aag agc ggt tca cag aat aat acc acc aac tat atg aag ggt act     1113
Gln Lys Ser Gly Ser Gln Asn Asn Thr Thr Asn Tyr Met Lys Gly Thr
180                 185                 190                 195 atc agc gta tcc aag cac ttt gac gca tgg tca aag gca ggt ctg gat     1161
Ile Ser Val Ser Lys His Phe Asp Ala Trp Ser Lys Ala Gly Leu Asp
                200                 205                 210 atg agc ggt act ctc tac gag gta tcc ctc aac atc gag ggc tac aga     1209
Met Ser Gly Thr Leu Tyr Glu Val Ser Leu Asn Ile Glu Gly Tyr Arg
            215                 220                 225 tca agc gga aac gct aac gtt aaa gct atc tca ttc gac ggc agt ata     1257
Ser Ser Gly Asn Ala Asn Val Lys Ala Ile Ser Phe Asp Gly Ser Ile
        230                 235                 240 ccc gag ccc aca agc gag ccc gta act cag ccc gtt gtc aag gca gag     1305
Pro Glu Pro Thr Ser Glu Pro Val Thr Gln Pro Val Val Lys Ala Glu
    245                 250                 255 cct gac gca aac ggc tac tac ttc aaa gaa aaa ttc gag agc ggc gca     1353
Pro Asp Ala Asn Gly Tyr Tyr Phe Lys Glu Lys Phe Glu Ser Gly Ala
260                 265                 270                 275 ggc gac tgg tca gcc cgc gga aca gga gct aag gta aca agc tct gac     1401
Gly Asp Trp Ser Ala Arg Gly Thr Gly Ala Lys Val Thr Ser Ser Asp
                280                 285                 290 gga ttc aac ggt tca aag ggc ata ctg gta tca gga cgc ggc gac aac     1449
Gly Phe Asn Gly Ser Lys Gly Ile Leu Val Ser Gly Arg Gly Asp Asn
```

```
                       295                  300                  305
tgg cac ggc gca cag ctc aca ctc gac tca agt gct ttc aca gca ggc      1497
Trp His Gly Ala Gln Leu Thr Leu Asp Ser Ser Ala Phe Thr Ala Gly
        310                  315                  320 gaa aca tac agc ttc ggc gca ctt gta aag cag gac ggc gag tcc tca      1545
Glu Thr Tyr Ser Phe Gly Ala Leu Val Lys Gln Asp Gly Glu Ser Ser
    325                  330                  335 aca gct atg aag ctc act ctc cag tat aac gac gca agc ggc aca gcc      1593
Thr Ala Met Lys Leu Thr Leu Gln Tyr Asn Asp Ala Ser Gly Thr Ala
340                  345                  350                  355 aat tac gat aag gtg gca gag ttc aca gct cca aag ggt gaa tgg gta      1641
Asn Tyr Asp Lys Val Ala Glu Phe Thr Ala Pro Lys Gly Glu Trp Val
                360                  365                  370 gac ctt tcc aat aca tcg ttc act atc ccg tca ggc gct tca gac ctc      1689
Asp Leu Ser Asn Thr Ser Phe Thr Ile Pro Ser Gly Ala Ser Asp Leu
            375                  380                  385 att ctc tat gtt gaa gct ccc gac agc ctt acg gat ttc tat atc gac      1737
Ile Leu Tyr Val Glu Ala Pro Asp Ser Leu Thr Asp Phe Tyr Ile Asp
        390                  395                  400 aac gct ttc ggc ggc atc aag aac aca tct cct ctt gaa gat gtc gga      1785
Asn Ala Phe Gly Gly Ile Lys Asn Thr Ser Pro Leu Glu Asp Val Gly
    405                  410                  415 agc cat act atc agc act ccg ggc agc gag aca aca aca gtc aca act      1833
Ser His Thr Ile Ser Thr Pro Gly Ser Glu Thr Thr Thr Val Thr Thr
420                  425                  430                  435 gca tca aat aag ggt atc aga ggc gat atc aac ggc gac ggc gtt atc      1881
Ala Ser Asn Lys Gly Ile Arg Gly Asp Ile Asn Gly Asp Gly Val Ile
                440                  445                  450 aac tca ttc gac ctt gct cct ctc aga aga ggc att ctc aag atg atg      1929
Asn Ser Phe Asp Leu Ala Pro Leu Arg Arg Gly Ile Leu Lys Met Met
            455                  460                  465 tca ggc agc ggc tcg act ccc gaa aat gct gac gta aac ggc gac ggc      1977
Ser Gly Ser Gly Ser Thr Pro Glu Asn Ala Asp Val Asn Gly Asp Gly
        470                  475                  480 act gta aat gtt gca gac ctc ctg ctt ctc cag aag ttt ata ctc ggt      2025
Thr Val Asn Val Ala Asp Leu Leu Leu Leu Gln Lys Phe Ile Leu Gly
    485                  490                  495 atg gag aag tca ttc ccc gat cct gta aca act acc acg acc aag ccg      2073
Met Glu Lys Ser Phe Pro Asp Pro Val Thr Thr Thr Thr Thr Lys Pro
500                  505                  510                  515 ata aca aca act acc gag aag ata gtt acc aca act act tct tca tct      2121
Ile Thr Thr Thr Thr Glu Lys Ile Val Thr Thr Thr Thr Ser Ser Ser
                520                  525                  530 tct tca agc tca ggc aag aac ctc aat gca gat atc cgc aag gat atg      2169
Ser Ser Ser Ser Gly Lys Asn Leu Asn Ala Asp Ile Arg Lys Asp Met
            535                  540                  545 cct act tca gtt ccc ggc gga aac gaa aag agc ggc ggc tgc aag gtc      2217
Pro Thr Ser Val Pro Gly Gly Asn Glu Lys Ser Gly Gly Cys Lys Val
        550                  555                  560 gag aag aag aca tac aac tgc aag ttc aca ggc ggt cag aag agc tgc      2265
Glu Lys Lys Thr Tyr Asn Cys Lys Phe Thr Gly Gly Gln Lys Ser Cys
    565                  570                  575 aac gtt atc ctg cct cct aac tac agc gca agc aag cag tac cct gtt      2313
Asn Val Ile Leu Pro Pro Asn Tyr Ser Ala Ser Lys Gln Tyr Pro Val
580                  585                  590                  595 atg tac gtt ctc cac ggt atc ggc gga aac gag gga agc atg gta agc      2361
Met Tyr Val Leu His Gly Ile Gly Gly Asn Glu Gly Ser Met Val Ser
                600                  605                  610 ggc atg ggc gtt cag gag ctt ctt gca gga ctt acc gca aac ggc aag      2409
Gly Met Gly Val Gln Glu Leu Leu Ala Gly Leu Thr Ala Asn Gly Lys
```

-continued

```
Gly Met Gly Val Gln Glu Leu Leu Ala Gly Leu Thr Ala Asn Gly Lys
            615                 620                 625 gca gag gaa atg ata atc gtt ctc ccg agc cag tac acc agc aag aac      2457
Ala Glu Glu Met Ile Ile Val Leu Pro Ser Gln Tyr Thr Ser Lys Asn
        630                 635                 640 ggc aat cag ggc ggc ggc ttc gga atc aat cag gaa gta tgc gca gct      2505
Gly Asn Gln Gly Gly Gly Phe Gly Ile Asn Gln Glu Val Cys Ala Ala
    645                 650                 655 tac gat aac ttc ctc tat gat atc tca gac agc ctt atc cca ttc atc      2553
Tyr Asp Asn Phe Leu Tyr Asp Ile Ser Asp Ser Leu Ile Pro Phe Ile
660                 665                 670                 675 gag gct aac tat ccc gtt aag aca ggc aga gaa aac cgt gct atc aca      2601
Glu Ala Asn Tyr Pro Val Lys Thr Gly Arg Glu Asn Arg Ala Ile Thr
                680                 685                 690 ggc ttc tca atg ggc gga cgt gaa gct atc tat atc ggt ctt atg cgt      2649
Gly Phe Ser Met Gly Gly Arg Glu Ala Ile Tyr Ile Gly Leu Met Arg
            695                 700                 705 ccc gac ctc ttc gct tac gtt ggc gga gct tgc cct gca ccc ggt atc      2697
Pro Asp Leu Phe Ala Tyr Val Gly Gly Ala Cys Pro Ala Pro Gly Ile
        710                 715                 720 acc cca ggc aag gat atg ttc atg gag cac cca ggc tgt atg cag gag      2745
Thr Pro Gly Lys Asp Met Phe Met Glu His Pro Gly Cys Met Gln Glu
    725                 730                 735 agc gaa atg aag ttc aga gac gtt gga cct gag ccg aat gta ttc atg      2793
Ser Glu Met Lys Phe Arg Asp Val Gly Pro Glu Pro Asn Val Phe Met
740                 745                 750                 755 ata aca ggc ggc aca aac gac ggc gtc gta gga aca ttc ccc aag cag      2841
Ile Thr Gly Gly Thr Asn Asp Gly Val Val Gly Thr Phe Pro Lys Gln
                760                 765                 770 tac agc gat atc ctt aca aga aac ggc gtt gac caa cgt tta cca gtc      2889
Tyr Ser Asp Ile Leu Thr Arg Asn Gly Val Asp Gln Arg Leu Pro Val
            775                 780                 785 tat ccc taacggcgga cacgacgcag gctctgtaaa gcctcatctc tacacattca       2945
Tyr Pro tgagatacgc attcaaataa tgatatagtt gacatatgaa ggacagcgct ttatgcgctg    3005
tctttctttt tgtgcaaaaa gaaaagccat ttgagctttt gaagctcaaa tggcttatat    3065
ttataatagt atagcttatt ctgttctgag agcctccaca                          3105

<210> SEQ ID NO 16
<211> LENGTH: 789
<212> TYPE: PRT
<213> ORGANISM: Ruminococcus sp.

<400> SEQUENCE: 16

Val Lys Lys Thr Val Lys Gln Phe Ile Ser Ser Ala Val Thr Ala Leu
 1               5                  10                  15

Met Val Ala Ala Ser Leu Pro Ala Val Pro Ser Val Asn Ala Ala Asp
            20                  25                  30

Ala Gln Gln Arg Gly Asn Ile Gly Gly Phe Asp Tyr Glu Met Trp Asn
        35                  40                  45

Gln Asn Gly Gln Gly Gln Val Ser Met Thr Pro Lys Ala Gly Ser Phe
    50                  55                  60

Thr Cys Ser Trp Ser Asn Ile Glu Asn Phe Leu Ala Arg Met Gly Lys
65                  70                  75                  80

Asn Tyr Asp Ser Gln Lys Lys Asn Tyr Lys Ala Phe Gly Asp Ile Thr
                85                  90                  95

Leu Ser Tyr Asp Val Glu Tyr Thr Pro Lys Gly Asn Ser Tyr Met Cys
```

-continued

```
                   100                 105                 110
Val Tyr Gly Trp Thr Arg Asn Pro Leu Met Glu Tyr Tyr Ile Val Glu
                115                 120                 125
Gly Trp Gly Asp Trp Arg Pro Pro Gly Asn Asp Gly Glu Asn Lys Gly
    130                 135                 140
Thr Val Thr Leu Asn Gly Asn Thr Tyr Asp Ile Arg Lys Thr Met Arg
145                 150                 155                 160
Tyr Asn Gln Pro Ser Leu Asp Gly Thr Ala Thr Phe Pro Gln Tyr Trp
                165                 170                 175
Ser Val Arg Gln Lys Ser Gly Ser Gln Asn Asn Thr Thr Asn Tyr Met
                180                 185                 190
Lys Gly Thr Ile Ser Val Ser Lys His Phe Asp Ala Trp Ser Lys Ala
                195                 200                 205
Gly Leu Asp Met Ser Gly Thr Leu Tyr Glu Val Ser Leu Asn Ile Glu
    210                 215                 220
Gly Tyr Arg Ser Ser Gly Asn Ala Asn Val Lys Ala Ile Ser Phe Asp
225                 230                 235                 240
Gly Ser Ile Pro Glu Pro Thr Ser Glu Pro Val Thr Gln Pro Val Val
                245                 250                 255
Lys Ala Glu Pro Asp Ala Asn Gly Tyr Tyr Phe Lys Glu Lys Phe Glu
                260                 265                 270
Ser Gly Ala Gly Asp Trp Ser Ala Arg Gly Thr Gly Ala Lys Val Thr
                275                 280                 285
Ser Ser Asp Gly Phe Asn Gly Ser Lys Gly Ile Leu Val Ser Gly Arg
    290                 295                 300
Gly Asp Asn Trp His Gly Ala Gln Leu Thr Leu Asp Ser Ser Ala Phe
305                 310                 315                 320
Thr Ala Gly Glu Thr Tyr Ser Phe Gly Ala Leu Val Lys Gln Asp Gly
                325                 330                 335
Glu Ser Ser Thr Ala Met Lys Leu Thr Leu Gln Tyr Asn Asp Ala Ser
                340                 345                 350
Gly Thr Ala Asn Tyr Asp Lys Val Ala Glu Phe Thr Ala Pro Lys Gly
                355                 360                 365
Glu Trp Val Asp Leu Ser Asn Thr Ser Phe Thr Ile Pro Ser Gly Ala
    370                 375                 380
Ser Asp Leu Ile Leu Tyr Val Glu Ala Pro Asp Ser Leu Thr Asp Phe
385                 390                 395                 400
Tyr Ile Asp Asn Ala Phe Gly Gly Ile Lys Asn Thr Ser Pro Leu Glu
                405                 410                 415
Asp Val Gly Ser His Thr Ile Ser Thr Pro Gly Ser Glu Thr Thr Thr
                420                 425                 430
Val Thr Thr Ala Ser Asn Lys Gly Ile Arg Gly Asp Ile Asn Gly Asp
    435                 440                 445
Gly Val Ile Asn Ser Phe Asp Leu Ala Pro Leu Arg Arg Gly Ile Leu
    450                 455                 460
Lys Met Met Ser Gly Gly Ser Thr Pro Glu Asn Ala Asp Val Asn
465                 470                 475                 480
Gly Asp Gly Thr Val Asn Val Ala Asp Leu Leu Leu Leu Gln Lys Phe
                485                 490                 495
Ile Leu Gly Met Glu Lys Ser Phe Pro Asp Pro Val Thr Thr Thr Thr
                500                 505                 510
Thr Lys Pro Ile Thr Thr Thr Glu Lys Ile Val Thr Thr Thr Thr
    515                 520                 525
```

```
Ser Ser Ser Ser Ser Ser Gly Lys Asn Leu Asn Ala Asp Ile Arg
    530                 535                 540

Lys Asp Met Pro Thr Ser Val Pro Gly Gly Asn Glu Lys Ser Gly Gly
545                 550                 555                 560

Cys Lys Val Glu Lys Lys Thr Tyr Asn Cys Lys Phe Thr Gly Gly Gln
                565                 570                 575

Lys Ser Cys Asn Val Ile Leu Pro Pro Asn Tyr Ser Ala Ser Lys Gln
            580                 585                 590

Tyr Pro Val Met Tyr Val Leu His Gly Ile Gly Asn Glu Gly Ser
                595                 600                 605

Met Val Ser Gly Met Gly Val Gln Glu Leu Leu Ala Gly Leu Thr Ala
    610                 615                 620

Asn Gly Lys Ala Glu Glu Met Ile Ile Val Leu Pro Ser Gln Tyr Thr
625                 630                 635                 640

Ser Lys Asn Gly Asn Gln Gly Gly Phe Gly Ile Asn Gln Glu Val
                645                 650                 655

Cys Ala Ala Tyr Asp Asn Phe Leu Tyr Asp Ile Ser Asp Ser Leu Ile
                660                 665                 670

Pro Phe Ile Glu Ala Asn Tyr Pro Val Lys Thr Gly Arg Glu Asn Arg
            675                 680                 685

Ala Ile Thr Gly Phe Ser Met Gly Gly Arg Glu Ala Ile Tyr Ile Gly
    690                 695                 700

Leu Met Arg Pro Asp Leu Phe Ala Tyr Val Gly Gly Ala Cys Pro Ala
705                 710                 715                 720

Pro Gly Ile Thr Pro Gly Lys Asp Met Phe Met Glu His Pro Gly Cys
                725                 730                 735

Met Gln Glu Ser Glu Met Lys Phe Arg Asp Val Gly Pro Glu Pro Asn
                740                 745                 750

Val Phe Met Ile Thr Gly Gly Thr Asn Asp Gly Val Val Gly Thr Phe
            755                 760                 765

Pro Lys Gln Tyr Ser Asp Ile Leu Thr Arg Asn Gly Val Asp Gln Arg
        770                 775                 780

Leu Pro Val Tyr Pro
785

<210> SEQ ID NO 17
<211> LENGTH: 1662
<212> TYPE: DNA
<213> ORGANISM: Orpinomyces sp. PC-2
<220> FEATURE:
<221> NAME/KEY: CDS
<222> LOCATION: (1)..(1590)

<400> SEQUENCE: 17 gtt gtt tct tgt gaa act act tac ggt att act tta cgt gat act aag     48
Val Val Ser Cys Glu Thr Thr Tyr Gly Ile Thr Leu Arg Asp Thr Lys
  1               5                  10                  15 gaa aaa ttc act gta ttc aaa gac ggt tcc gct gct act gat att gtt    96
Glu Lys Phe Thr Val Phe Lys Asp Gly Ser Ala Ala Thr Asp Ile Val
             20                  25                  30 gaa tca gaa gat ggt tcc gtt tct tgg att gct act gct gcc ggt ggt   144
Glu Ser Glu Asp Gly Ser Val Ser Trp Ile Ala Thr Ala Ala Gly Gly
         35                  40                  45 gct ggt ggt ggt gtt gcc ttc tat gtt aag gct aac aag gaa gaa att   192
Ala Gly Gly Gly Val Ala Phe Tyr Val Lys Ala Asn Lys Glu Glu Ile
     50                  55                  60
```

```
aac att gct aac tat gaa tct atc gat att gaa atg gaa tac act cca         240
Asn Ile Ala Asn Tyr Glu Ser Ile Asp Ile Glu Met Glu Tyr Thr Pro
 65                  70                  75                  80 gtt gaa aac aaa tgg aat gat gct gct aag aac cca agt ttc tgt atg         288
Val Glu Asn Lys Trp Asn Asp Ala Ala Lys Asn Pro Ser Phe Cys Met
                 85                  90                  95 aga att ctt cca tgg gat tcc act ggt atg ttc ggt ggt tac gaa gat         336
Arg Ile Leu Pro Trp Asp Ser Thr Gly Met Phe Gly Gly Tyr Glu Asp
            100                 105                 110 ctt gaa tac ttc gat act cca gca aaa tct ggt aat ttc aaa tac act         384
Leu Glu Tyr Phe Asp Thr Pro Ala Lys Ser Gly Asn Phe Lys Tyr Thr
        115                 120                 125 att aag att cct tcc ttc ttt gct gat aag att tta tct agc tct gat         432
Ile Lys Ile Pro Ser Phe Phe Ala Asp Lys Ile Leu Ser Ser Ser Asp
    130                 135                 140 ctc gat tct atc tta agt ttt gct atc aag ttc aac gat tat gaa aga         480
Leu Asp Ser Ile Leu Ser Phe Ala Ile Lys Phe Asn Asp Tyr Glu Arg
145                 150                 155                 160 ggt aac acg gac ggt gac caa att aag att caa tta aag aat gtt aaa         528
Gly Asn Thr Asp Gly Asp Gln Ile Lys Ile Gln Leu Lys Asn Val Lys
                165                 170                 175 ttc aac cca aag gaa aat gct cca gaa gat aag gct ttc gat gat ggt         576
Phe Asn Pro Lys Glu Asn Ala Pro Glu Asp Lys Ala Phe Asp Asp Gly
            180                 185                 190 tta agg gat tct caa cgt ggt act gtc gtt gaa atg aaa tac tca tct         624
Leu Arg Asp Ser Gln Arg Gly Thr Val Val Glu Met Lys Tyr Ser Ser
        195                 200                 205 aga gat tac acc gtc aag gaa tct gaa gct gac aaa tac gaa aag cac         672
Arg Asp Tyr Thr Val Lys Glu Ser Glu Ala Asp Lys Tyr Glu Lys His
    210                 215                 220 gct tgg gtt tac ctt cca gct ggt tat gaa gct gat aac aag gat aag         720
Ala Trp Val Tyr Leu Pro Ala Gly Tyr Glu Ala Asp Asn Lys Asp Lys
225                 230                 235                 240 aaa tac cca tta gtt gtt tta ctt cac ggt tat ggt caa aat gaa aac         768
Lys Tyr Pro Leu Val Val Leu Leu His Gly Tyr Gly Gln Asn Glu Asn
                245                 250                 255 act tgg ggt ctt tcc aac aag ggt cgt ggt ggt aag atc aag ggt tac         816
Thr Trp Gly Leu Ser Asn Lys Gly Arg Gly Gly Lys Ile Lys Gly Tyr
            260                 265                 270 atg gac aga ggt atg gct agt ggt aat gtt gaa aag ttt gtt ctt gtt         864
Met Asp Arg Gly Met Ala Ser Gly Asn Val Glu Lys Phe Val Leu Val
        275                 280                 285 gcc gct act ggt gtt gcc agt aag aat tgg ggt cca aac ggt tct ggt         912
Ala Ala Thr Gly Val Ala Ser Lys Asn Trp Gly Pro Asn Gly Ser Gly
    290                 295                 300 gtt gat ctt gat ggt ttc aat gct ttc ggt ggt gaa ctc aga aac gat         960
Val Asp Leu Asp Gly Phe Asn Ala Phe Gly Gly Glu Leu Arg Asn Asp
305                 310                 315                 320 tta ctc cca tac att aga gct cac ttc aat gtt aag gtc gat cgt gat        1008
Leu Leu Pro Tyr Ile Arg Ala His Phe Asn Val Lys Val Asp Arg Asp
                325                 330                 335 cac act gct tta gct ggt ctt tcc atg ggt ggt ggt caa act atc agt        1056
His Thr Ala Leu Ala Gly Leu Ser Met Gly Gly Gly Gln Thr Ile Ser
            340                 345                 350 att ggt att ggt gaa act ctt gat gaa atc agt aac tac ggt tct ttc        1104
Ile Gly Ile Gly Glu Thr Leu Asp Glu Ile Ser Asn Tyr Gly Ser Phe
        355                 360                 365 tct cca gct tta ttc caa act gct gaa gaa ttc ttc ggt aag gtt aag        1152
Ser Pro Ala Leu Phe Gln Thr Ala Glu Glu Phe Phe Gly Lys Val Lys
    370                 375                 380
```

```
ggt aac ttc aag gaa gaa ctt aga att cac aac ctt tac atg act tgt      1200
Gly Asn Phe Lys Glu Glu Leu Arg Ile His Asn Leu Tyr Met Thr Cys
385                 390                 395                 400 ggt gat gct gat act tta gtt tac gat act tac cca agt tac gtt gaa      1248
Gly Asp Ala Asp Thr Leu Val Tyr Asp Thr Tyr Pro Ser Tyr Val Glu
                405                 410                 415 gct tta aag aat tgg gat gct gtt gaa ttc atg aag gaa tac act tac      1296
Ala Leu Lys Asn Trp Asp Ala Val Glu Phe Met Lys Glu Tyr Thr Tyr
            420                 425                 430 cca ggt ggt act cac gat ttc cca gtt tgg tac aga ggt ttc aac gaa      1344
Pro Gly Gly Thr His Asp Phe Pro Val Trp Tyr Arg Gly Phe Asn Glu
        435                 440                 445 ttc att caa att gtt ttc aaa aat caa aaa gtt aag gaa gaa cca att      1392
Phe Ile Gln Ile Val Phe Lys Asn Gln Lys Val Lys Glu Glu Pro Ile
    450                 455                 460 cat gct gat cca gta gaa gac cca tct gat gaa cca gtt agt gtt gat      1440
His Ala Asp Pro Val Glu Asp Pro Ser Asp Glu Pro Val Ser Val Asp
465                 470                 475                 480 cca tct gtt tct gtc gaa gaa cca aat gac agt gaa tct tcc tct gaa      1488
Pro Ser Val Ser Val Glu Glu Pro Asn Asp Ser Glu Ser Ser Ser Glu
                485                 490                 495 gat gaa cca gtg gtt aaa aaa act att aag cac acc att gct aag aag      1536
Asp Glu Pro Val Val Lys Lys Thr Ile Lys His Thr Ile Ala Lys Lys
            500                 505                 510 aag cca tct aag act aga act gtt acc aag aag gtc att aag aag aag      1584
Lys Pro Ser Lys Thr Arg Thr Val Thr Lys Lys Val Ile Lys Lys Lys
        515                 520                 525 aat aac taagaaagtt tagttagtac agtagtgtaa aaaaaaaaa aaaatcaaaa        1640
Asn Asn
    530 agaaactcgt gccgaattcg at                                             1662

<210> SEQ ID NO 18
<211> LENGTH: 530
<212> TYPE: PRT
<213> ORGANISM: Orpinomyces sp. PC-2

<400> SEQUENCE: 18

Val Val Ser Cys Glu Thr Thr Tyr Gly Ile Thr Leu Arg Asp Thr Lys
 1               5                  10                  15

Glu Lys Phe Thr Val Phe Lys Asp Gly Ser Ala Ala Thr Asp Ile Val
            20                  25                  30

Glu Ser Glu Asp Gly Ser Val Ser Trp Ile Ala Thr Ala Ala Gly Gly
        35                  40                  45

Ala Gly Gly Val Ala Phe Tyr Val Lys Ala Asn Lys Glu Glu Ile
    50                  55                  60

Asn Ile Ala Asn Tyr Glu Ser Ile Asp Ile Glu Met Glu Tyr Thr Pro
65                  70                  75                  80

Val Glu Asn Lys Trp Asn Asp Ala Ala Lys Asn Pro Ser Phe Cys Met
                85                  90                  95

Arg Ile Leu Pro Trp Asp Ser Thr Gly Met Phe Gly Gly Tyr Glu Asp
            100                 105                 110

Leu Glu Tyr Phe Asp Thr Pro Ala Lys Ser Gly Asn Phe Lys Tyr Thr
        115                 120                 125

Ile Lys Ile Pro Ser Phe Phe Ala Asp Lys Ile Leu Ser Ser Ser Asp
    130                 135                 140

Leu Asp Ser Ile Leu Ser Phe Ala Ile Lys Phe Asn Asp Tyr Glu Arg
```

```
                 145                 150                 155                 160
Gly Asn Thr Asp Gly Asp Gln Ile Lys Ile Gln Leu Lys Asn Val Lys
                165                 170                 175

Phe Asn Pro Lys Glu Asn Ala Pro Glu Asp Lys Ala Phe Asp Asp Gly
                180                 185                 190

Leu Arg Asp Ser Gln Arg Gly Thr Val Val Glu Met Lys Tyr Ser Ser
                195                 200                 205

Arg Asp Tyr Thr Val Lys Glu Ser Glu Ala Asp Lys Tyr Glu Lys His
                210                 215                 220

Ala Trp Val Tyr Leu Pro Ala Gly Tyr Glu Ala Asp Asn Lys Asp Lys
225                 230                 235                 240

Lys Tyr Pro Leu Val Val Leu Leu His Gly Tyr Gly Gln Asn Glu Asn
                245                 250                 255

Thr Trp Gly Leu Ser Asn Lys Gly Arg Gly Lys Ile Lys Gly Tyr
                260                 265                 270

Met Asp Arg Gly Met Ala Ser Gly Asn Val Glu Lys Phe Val Leu Val
                275                 280                 285

Ala Ala Thr Gly Val Ala Ser Lys Asn Trp Gly Pro Asn Gly Ser Gly
                290                 295                 300

Val Asp Leu Asp Gly Phe Asn Ala Phe Gly Gly Glu Leu Arg Asn Asp
305                 310                 315                 320

Leu Leu Pro Tyr Ile Arg Ala His Phe Asn Val Lys Val Asp Arg Asp
                325                 330                 335

His Thr Ala Leu Ala Gly Leu Ser Met Gly Gly Gly Gln Thr Ile Ser
                340                 345                 350

Ile Gly Ile Gly Glu Thr Leu Asp Glu Ile Ser Asn Tyr Gly Ser Phe
                355                 360                 365

Ser Pro Ala Leu Phe Gln Thr Ala Glu Phe Phe Gly Lys Val Lys
                370                 375                 380

Gly Asn Phe Lys Glu Glu Leu Arg Ile His Asn Leu Tyr Met Thr Cys
385                 390                 395                 400

Gly Asp Ala Asp Thr Leu Val Tyr Asp Thr Tyr Pro Ser Tyr Val Glu
                405                 410                 415

Ala Leu Lys Asn Trp Asp Ala Val Glu Phe Met Lys Glu Tyr Thr Tyr
                420                 425                 430

Pro Gly Gly Thr His Asp Phe Pro Val Trp Tyr Arg Gly Phe Asn Glu
                435                 440                 445

Phe Ile Gln Ile Val Phe Lys Asn Gln Lys Val Lys Glu Glu Pro Ile
450                 455                 460

His Ala Asp Pro Val Glu Asp Pro Ser Asp Glu Pro Val Ser Val Asp
465                 470                 475                 480

Pro Ser Val Ser Val Glu Glu Pro Asn Asp Ser Glu Ser Ser Ser Glu
                485                 490                 495

Asp Glu Pro Val Val Lys Lys Thr Ile Lys His Thr Ile Ala Lys Lys
                500                 505                 510

Lys Pro Ser Lys Thr Arg Thr Val Thr Lys Lys Val Ile Lys Lys Lys
                515                 520                 525

Asn Asn
    530

<210> SEQ ID NO 19
<211> LENGTH: 400
<212> TYPE: PRT
<213> ORGANISM: Escherichia coli
```

-continued

```
<400> SEQUENCE: 19

Met Val Met Glu Leu Asn Glu Arg Asn Ile Thr Met Asn Ile Lys Ile
  1               5                  10                  15

Ala Ala Leu Thr Leu Ala Ile Ala Ser Gly Ile Ser Ala Gln Trp Ala
             20                  25                  30

Ile Ala Ala Asp Met Pro Ala Ser Pro Ala Pro Thr Ile Pro Val Lys
         35                  40                  45

Gln Tyr Val Thr Gln Val Asn Ala Asp Asn Ser Val Thr Phe Arg Tyr
     50                  55                  60

Phe Ala Pro Gly Ala Lys Asn Val Ser Val Val Gly Val Pro Val
 65                  70                  75                  80

Pro Asp Asn Ile His Pro Met Thr Lys Asp Glu Ala Gly Val Trp Ser
                 85                  90                  95

Trp Arg Thr Pro Ile Leu Lys Gly Asn Leu Tyr Glu Tyr Phe Phe Asn
                100                 105                 110

Val Asp Gly Val Arg Ser Ile Asp Thr Gly Thr Ala Met Thr Asn Pro
            115                 120                 125

Gln Arg Gln Val Asn Ser Ser Met Ile Leu Val Pro Gly Ser Tyr Leu
        130                 135                 140

Asp Thr Arg Ser Val Ala His Gly Asp Leu Ile Ala Ile Thr Tyr His
145                 150                 155                 160

Ser Asn Ala Leu Gln Ser Glu Arg Gln Met Tyr Val Trp Thr Pro Pro
                165                 170                 175

Gly Tyr Thr Gly Met Gly Glu Pro Leu Pro Val Leu Tyr Phe Tyr His
            180                 185                 190

Gly Phe Gly Asp Thr Gly Arg Ser Ala Ile Asp Gln Gly Arg Ile Pro
        195                 200                 205

Gln Ile Met Asp Asn Leu Leu Ala Glu Gly Lys Ile Lys Pro Met Leu
    210                 215                 220

Val Val Ile Pro Asp Thr Glu Thr Asp Ala Lys Gly Ile Ile Pro Glu
225                 230                 235                 240

Asp Phe Val Pro Gln Glu Arg Arg Lys Val Phe Tyr Pro Leu Asn Ala
                245                 250                 255

Lys Ala Ala Asp Arg Glu Leu Met Asn Asp Ile Ile Pro Leu Ile Ser
            260                 265                 270

Lys Arg Phe Asn Val Arg Lys Asp Ala Asp Gly Arg Ala Leu Ala Gly
        275                 280                 285

Leu Ser Gln Gly Gly Tyr Gln Ala Leu Val Ser Gly Met Asn His Leu
    290                 295                 300

Glu Ser Phe Gly Trp Leu Ala Thr Phe Ser Gly Val Thr Thr Thr Thr
305                 310                 315                 320

Val Pro Asp Glu Gly Val Ala Ala Arg Leu Asn Asp Pro Ala Ala Ile
                325                 330                 335

Asn Gln Gln Leu Arg Asn Phe Thr Val Val Gly Asp Lys Asp Val
            340                 345                 350

Val Thr Gly Lys Asp Ile Ala Gly Leu Lys Thr Glu Leu Glu Gln Lys
        355                 360                 365

Lys Ile Asn Phe Asp Tyr Gln Glu Tyr Pro Gly Leu Asn His Glu Met
    370                 375                 380

Asp Val Trp Arg Pro Ala Tyr Ala Ala Phe Val Gln Lys Leu Phe Lys
385                 390                 395                 400
```

-continued

```
<210> SEQ ID NO 20
<211> LENGTH: 721
<212> TYPE: PRT
<213> ORGANISM: Aspergillus fumigatus

<400> SEQUENCE: 20

Met Gly Ala Phe Arg Trp Leu Ser Ile Ala Ala Ala Ser Thr Ala
 1               5                  10                  15

Leu Ala Leu Thr Pro Glu Gln Leu Ile Thr Ala Pro Arg Arg Ser Glu
                 20                  25                  30

Ala Ile Pro Asp Pro Ser Gly Lys Val Ala Val Phe Ser Thr Ser Gln
             35                  40                  45

Tyr Ser Phe Glu Thr His Lys Arg Thr Ser Trp Trp Ser Leu Leu Asp
 50                  55                  60

Leu Lys Thr Gly Gln Thr Lys Val Leu Thr Asn Asp Ser Ser Val Ser
 65                  70                  75                  80

Glu Ile Val Trp Leu Ser Asp Ser Ile Leu Tyr Val Asn Ser Thr
                 85                  90                  95

Asn Ala Asp Ile Pro Gly Gly Val Glu Leu Trp Val Thr Gln Ala Ser
            100                 105                 110

Ser Phe Ala Lys Gly Tyr Lys Ala Ala Ser Leu Pro Ala Ser Phe Ser
        115                 120                 125

Gly Leu Lys Ala Ala Lys Thr Lys Ser Gly Asp Ile Arg Phe Val Ala
    130                 135                 140

Tyr Gly Gln Ser Tyr Pro Asn Gly Thr Ala Tyr Asn Glu Glu Leu Ala
145                 150                 155                 160

Thr Ala Pro Leu Ser Ser Ala Arg Ile Tyr Asp Ser Ile Tyr Val Arg
                165                 170                 175

His Trp Asp Tyr Trp Leu Ser Thr Thr Phe Asn Ala Val Phe Ser Gly
            180                 185                 190

Thr Leu Lys Lys Gly His Gly Lys Asn Gly Tyr Ser Leu Asp Gly Glu
        195                 200                 205

Leu Lys Asn Leu Val Ser Pro Val Lys Asn Ala Glu Ser Pro Tyr Pro
    210                 215                 220

Pro Phe Gly Gly Ala Ser Asp Tyr Asp Leu Ser Pro Asp Gly Lys Trp
225                 230                 235                 240

Val Ala Phe Lys Ser Lys Ala Pro Glu Leu Pro Lys Ala Asn Phe Thr
                245                 250                 255

Thr Ser Tyr Ile Tyr Leu Val Pro His Asp Ala Ser Glu Thr Ala Arg
            260                 265                 270

Pro Ile Asn Gly Pro Asp Ser Pro Gly Thr Pro Lys Gly Ile Lys Gly
        275                 280                 285

Asp Ser Ser Pro Val Phe Ser Pro Asn Gly Asp Lys Leu Ala Tyr
    290                 295                 300

Phe Gln Met Arg Asp Glu Thr Tyr Glu Ser Asp Arg Ala Leu Leu Tyr
305                 310                 315                 320

Val Tyr Ser Leu Gly Ser Lys Lys Thr Ile Pro Ser Val Ala Gly Asp
                325                 330                 335

Trp Asp Arg Ser Pro Asp Ser Val Lys Trp Thr Pro Asp Gly Lys Thr
            340                 345                 350

Leu Ile Val Gly Ser Glu Asp Leu Gly Arg Thr Arg Leu Phe Ser Leu
        355                 360                 365

Pro Ala Asn Ala Lys Asp Asp Tyr Lys Pro Lys Asn Phe Thr Asp Gly
    370                 375                 380
```

```
Gly Ser Val Ser Ala Tyr Tyr Phe Leu Pro Asp Ser Ser Leu Leu Val
385                 390                 395                 400

Thr Gly Ser Ala Leu Trp Thr Asn Trp Asn Val Tyr Thr Ala Lys Pro
                405                 410                 415

Glu Lys Gly Val Ile Lys Lys Ile Ala Ser Ala Asn Glu Ile Asp Pro
            420                 425                 430

Glu Leu Lys Gly Leu Gly Pro Ser Asp Ile Ser Glu Phe Tyr Phe Gln
            435                 440                 445

Gly Asn Phe Thr Asp Ile His Ala Trp Val Ile Tyr Pro Glu Asn Phe
        450                 455                 460

Asp Lys Ser Lys Lys Tyr Pro Leu Ile Phe Phe Ile His Gly Gly Pro
465                 470                 475                 480

Gln Gly Asn Trp Ala Asp Gly Trp Ser Thr Arg Trp Asn Pro Lys Ala
                485                 490                 495

Trp Ala Asp Gln Gly Tyr Val Val Ala Pro Asn Pro Thr Gly Ser
            500                 505                 510

Thr Gly Phe Gly Gln Ala Leu Thr Thr Ala Ile Gln Asn Asn Trp Gly
            515                 520                 525

Gly Ala Pro Tyr Asp Asp Leu Val Lys Cys Trp Glu Tyr Val His Glu
        530                 535                 540

Asn Leu Asp Tyr Val Asp Thr Asp His Gly Val Ala Ala Gly Ala Ser
545                 550                 555                 560

Tyr Gly Gly Phe Met Ile Asn Trp Ile Gln Gly Ser Pro Leu Gly Arg
                565                 570                 575

Lys Phe Lys Ala Leu Val Ser His Asp Gly Thr Phe Val Ala Asp Ala
                580                 585                 590

Lys Val Ser Thr Glu Glu Leu Trp Phe Met Gln Arg Glu Phe Asn Gly
                595                 600                 605

Thr Phe Trp Asp Ala Arg Asp Asn Tyr Arg Arg Trp Asp Pro Ser Ala
        610                 615                 620

Pro Glu Arg Ile Leu Gln Phe Ala Thr Pro Met Leu Val Ile His Ser
625                 630                 635                 640

Asp Lys Asp Tyr Arg Leu Pro Val Ala Glu Gly Leu Ser Leu Phe Asn
                645                 650                 655

Val Leu Gln Glu Arg Gly Val Pro Ser Arg Phe Leu Asn Phe Pro Asp
                660                 665                 670

Glu Asn His Trp Val Val Asn Pro Glu Asn Ser Leu Val Trp His Gln
            675                 680                 685

Gln Ala Leu Gly Trp Ile Asn Lys Tyr Ser Gly Val Glu Lys Ser Asn
        690                 695                 700

Pro Asn Ala Val Ser Leu Glu Asp Thr Val Val Pro Val Val Asn Tyr
705                 710                 715                 720

Asn

<210> SEQ ID NO 21
<211> LENGTH: 20
<212> TYPE: PRT
<213> ORGANISM: Orpinomyces sp. PC-2
<220> FEATURE:
<223> OTHER INFORMATION: Description of Artificial Sequence:N-terminal
      amino acid sequence of a feruloyl esterase of
      Orpinomyces PC-2.

<400> SEQUENCE: 21

Glu Thr Thr Tyr Gly Ile Thr Leu Arg Asp Thr Lys Glu Lys Phe Thr
1               5                   10                  15
```

Val Phe Lys Asp
            20

<210> SEQ ID NO 22
<211> LENGTH: 400
<212> TYPE: PRT
<213> ORGANISM: Escherichia coli

<400> SEQUENCE: 22

Met Val Met Glu Leu Asn Glu Arg Asn Ile Thr Met Asn Ile Lys Ile
 1               5                  10                  15

Ala Ala Leu Thr Leu Ala Ile Ala Ser Gly Ile Ser Ala Gln Trp Ala
                20                  25                  30

Ile Ala Ala Asp Met Pro Ala Ser Pro Ala Pro Thr Ile Pro Val Lys
            35                  40                  45

Gln Tyr Val Thr Gln Val Asn Ala Asp Asn Ser Val Thr Phe Arg Tyr
        50                  55                  60

Phe Ala Pro Gly Ala Lys Asn Val Ser Val Val Gly Val Pro Val
 65                  70                  75                  80

Pro Asp Asn Ile His Pro Met Thr Lys Asp Glu Ala Gly Val Trp Ser
                85                  90                  95

Trp Arg Thr Pro Ile Leu Lys Gly Asn Leu Tyr Glu Tyr Phe Phe Asn
                100                 105                 110

Val Asp Gly Val Arg Ser Ile Asp Thr Gly Thr Ala Met Thr Asn Pro
            115                 120                 125

Gln Arg Gln Val Asn Ser Ser Met Ile Leu Val Pro Gly Ser Tyr Leu
        130                 135                 140

Asp Thr Arg Ser Val Ala His Gly Asp Leu Ile Ala Ile Thr Tyr His
145                 150                 155                 160

Ser Asn Ala Leu Gln Ser Glu Arg Gln Met Tyr Val Trp Thr Pro Pro
                165                 170                 175

Gly Tyr Thr Gly Met Gly Glu Pro Leu Pro Val Leu Tyr Phe Tyr His
            180                 185                 190

Gly Phe Gly Asp Thr Gly Arg Ser Ala Ile Asp Gln Gly Arg Ile Pro
        195                 200                 205

Gln Ile Met Asp Asn Leu Leu Ala Glu Gly Lys Ile Lys Pro Met Leu
    210                 215                 220

Val Val Ile Pro Asp Thr Glu Thr Asp Ala Lys Gly Ile Ile Pro Glu
225                 230                 235                 240

Asp Phe Val Pro Gln Glu Arg Arg Lys Val Phe Tyr Pro Leu Asn Ala
                245                 250                 255

Lys Ala Ala Asp Arg Glu Leu Met Asn Asp Ile Ile Pro Leu Ile Ser
            260                 265                 270

Lys Arg Phe Asn Val Arg Lys Asp Ala Asp Gly Arg Ala Leu Ala Gly
        275                 280                 285

Leu Ser Gln Gly Gly Tyr Gln Ala Leu Val Ser Gly Met Asn His Leu
    290                 295                 300

Glu Ser Phe Gly Trp Leu Ala Thr Phe Ser Gly Val Thr Thr Thr Thr
305                 310                 315                 320

Val Pro Asp Glu Gly Val Ala Ala Arg Leu Asn Asp Pro Ala Ala Ile
                325                 330                 335

Asn Gln Gln Leu Arg Asn Phe Thr Val Val Gly Asp Lys Asp Val
            340                 345                 350

Val Thr Gly Lys Asp Ile Ala Gly Leu Lys Thr Glu Leu Glu Gln Lys

```
              355                 360                 365
Lys Ile Asn Phe Asp Tyr Gln Glu Tyr Pro Gly Leu Asn His Glu Met
        370                 375                 380

Asp Val Trp Arg Pro Ala Tyr Ala Ala Phe Val Gln Lys Leu Phe Lys
385                 390                 395                 400

<210> SEQ ID NO 23
<211> LENGTH: 2364
<212> TYPE: DNA
<213> ORGANISM: Clostridium stercorarium
<220> FEATURE:
<221> NAME/KEY: CDS
<222> LOCATION: (440)..(1975)

<400> SEQUENCE: 23
aagcttaatt tgtttggtat accttgcttt atgttcaatc acgttctcgt cattaaacaa      60
cccatataag ctgctccctg accggaaagt tgaacattga ttcttgcatt ccgaatctgc     120
tccaataaaa catttctgaa tttcgagacg gcaaaaaatg atgccgcttc catttcaaca     180
gtaacacagc cttctgcaat cctttcgtc agcttccttt aaatttttaag tttgtctatt     240 gacaaaacta aaaactgtaa ttactataaa aatataacta ataaattaca ttttttaacat    300 cattatgggg tactggtaaa gacgtgatag ttattaataa atttaacaaa taataacaca     360
ctgctatctt cgaccgtaaa tttactatgt ctctaatgta atatgacata ataatataa      420 gtaaaggagg taaagtttt atg aag cgt aag gtt aag aag atg gca gct atg      472
                      Met Lys Arg Lys Val Lys Lys Met Ala Ala Met
                       1               5                  10 gca acg agt ata att atg gct atc atg atc atc cta cat agt ata cca       520
Ala Thr Ser Ile Ile Met Ala Ile Met Ile Ile Leu His Ser Ile Pro
                15                  20                  25 gta ctc gcc ggg cga ata att tac gac aat gag aca ggc aca cat gga       568
Val Leu Ala Gly Arg Ile Ile Tyr Asp Asn Glu Thr Gly Thr His Gly
        30                  35                  40 ggc tac gac tat gag ctc tgg aaa gac tac gga aat acg att atg gaa       616
Gly Tyr Asp Tyr Glu Leu Trp Lys Asp Tyr Gly Asn Thr Ile Met Glu
    45                  50                  55 ctt aac gac ggt ggt act ttt agt tgt caa tgg agt aat atc ggt aat       664
Leu Asn Asp Gly Gly Thr Phe Ser Cys Gln Trp Ser Asn Ile Gly Asn
60                  65                  70                  75 gca cta ttt aga aaa ggg aga aaa ttt aat tcc gac aaa acc tat caa       712
Ala Leu Phe Arg Lys Gly Arg Lys Phe Asn Ser Asp Lys Thr Tyr Gln
                80                  85                  90 gaa tta gga gac ata gta gtt gaa tat ggc tgt gat tac aat cca aac       760
Glu Leu Gly Asp Ile Val Val Glu Tyr Gly Cys Asp Tyr Asn Pro Asn
            95                 100                 105 gga aat tcc tat ttg tgt gtt tac ggt tgg aca aga aat cca ctg gtt       808
Gly Asn Ser Tyr Leu Cys Val Tyr Gly Trp Thr Arg Asn Pro Leu Val
        110                 115                 120 gaa tat tac att gta gaa agc tgg ggc agc tgg cgt cca cct gga gca       856
Glu Tyr Tyr Ile Val Glu Ser Trp Gly Ser Trp Arg Pro Pro Gly Ala
    125                 130                 135 aca ccc aaa gga acc atc aca cag tgg atg gca ggt act tat gaa ata       904
Thr Pro Lys Gly Thr Ile Thr Gln Trp Met Ala Gly Thr Tyr Glu Ile
140                 145                 150                 155 tat gaa act acc cgg gta aat cag cct tcc atc gat gga act gcg aca       952
Tyr Glu Thr Thr Arg Val Asn Gln Pro Ser Ile Asp Gly Thr Ala Thr
                160                 165                 170 ttc caa caa tat tgg agt gtt cgt aca tcc aag aga aca agc gga aca      1000
Phe Gln Gln Tyr Trp Ser Val Arg Thr Ser Lys Arg Thr Ser Gly Thr
```

-continued

```
                   175                 180                 185
ata tct gtc act gaa cat ttt aaa cag tgg gaa aga atg ggc atg cga    1048
Ile Ser Val Thr Glu His Phe Lys Gln Trp Glu Arg Met Gly Met Arg
            190                 195                 200 atg ggt aag atg tat gaa gtt gct ctt acc gtt gaa ggt tat cag agc    1096
Met Gly Lys Met Tyr Glu Val Ala Leu Thr Val Glu Gly Tyr Gln Ser
        205                 210                 215 agt ggg tac gct aat gta tac aag aat gaa atc aga ata ggt gca aat    1144
Ser Gly Tyr Ala Asn Val Tyr Lys Asn Glu Ile Arg Ile Gly Ala Asn
220                 225                 230                 235 cca act cct gcc cca tct caa agc cca att aga aga gat gca ttt tca    1192
Pro Thr Pro Ala Pro Ser Gln Ser Pro Ile Arg Arg Asp Ala Phe Ser
                240                 245                 250 ata atc gaa gcg gaa gaa tat aac agc aca aat tcc tcc act tta caa    1240
Ile Ile Glu Ala Glu Glu Tyr Asn Ser Thr Asn Ser Ser Thr Leu Gln
            255                 260                 265 gtg att gga acg cca aat aat ggc aga gga att ggt tat att gaa aat    1288
Val Ile Gly Thr Pro Asn Asn Gly Arg Gly Ile Gly Tyr Ile Glu Asn
        270                 275                 280 ggt aat acc gta act tac agc aat ata gat ttt ggt agt ggt gca aca    1336
Gly Asn Thr Val Thr Tyr Ser Asn Ile Asp Phe Gly Ser Gly Ala Thr
285                 290                 295 ggg ttc tct gca act gtt gca acg gag gtt aat acc tca att caa atc    1384
Gly Phe Ser Ala Thr Val Ala Thr Glu Val Asn Thr Ser Ile Gln Ile
300                 305                 310                 315 cgt tct gac agt cct acc gga act cta ctt ggt acc tta tat gta agt    1432
Arg Ser Asp Ser Pro Thr Gly Thr Leu Leu Gly Thr Leu Tyr Val Ser
                320                 325                 330 tct acc ggc agc tgg aat aca tat caa acc gta tct aca aac atc agc    1480
Ser Thr Gly Ser Trp Asn Thr Tyr Gln Thr Val Ser Thr Asn Ile Ser
            335                 340                 345 aaa att acc ggc gtt cat gat att gta ttg gta ttc tca ggt cca gtc    1528
Lys Ile Thr Gly Val His Asp Ile Val Leu Val Phe Ser Gly Pro Val
        350                 355                 360 aat gtg gac aac ttc ata ttt agc aga agt tca cca gtg cct gca cct    1576
Asn Val Asp Asn Phe Ile Phe Ser Arg Ser Ser Pro Val Pro Ala Pro
365                 370                 375 ggt gat aac aca aga gac gca tat tct atc att cag gcc gag gat tat    1624
Gly Asp Asn Thr Arg Asp Ala Tyr Ser Ile Ile Gln Ala Glu Asp Tyr
380                 385                 390                 395 gac agc agt tat ggt ccc aac ctt caa atc ttt agc tta cca ggt ggt    1672
Asp Ser Ser Tyr Gly Pro Asn Leu Gln Ile Phe Ser Leu Pro Gly Gly
                400                 405                 410 ggc agc gcc att ggc tat att gaa aat ggt tat tcc act acc tat aaa    1720
Gly Ser Ala Ile Gly Tyr Ile Glu Asn Gly Tyr Ser Thr Thr Tyr Lys
            415                 420                 425 aat att gat ttt ggt gac ggc gca acg tcc gta aca gca aga gta gct    1768
Asn Ile Asp Phe Gly Asp Gly Ala Thr Ser Val Thr Ala Arg Val Ala
        430                 435                 440 acc cag aat gct act acc att cag gta aga ttg gga agt cca tcg ggt    1816
Thr Gln Asn Ala Thr Thr Ile Gln Val Arg Leu Gly Ser Pro Ser Gly
            445                 450                 455 aca tta ctt gga aca att tac gtg ggg tcc aca gga agc ttt gat act    1864
Thr Leu Leu Gly Thr Ile Tyr Val Gly Ser Thr Gly Ser Phe Asp Thr
460                 465                 470                 475 tat agg gat gta tcc gct acc att agt aat act gcg ggt gta aaa gat    1912
Tyr Arg Asp Val Ser Ala Thr Ile Ser Asn Thr Ala Gly Val Lys Asp
                480                 485                 490 att gtt ctt gta ttc tca ggt cct gtt aat gtt gac tgg ttt gta ttc    1960
```

```
Ile Val Leu Val Phe Ser Gly Pro Val Asn Val Asp Trp Phe Val Phe
                495             500             505 tca aaa tca gga act taagggtata gaccctaatg tggagtacaa aatctggtat     2015
Ser Lys Ser Gly Thr
        510 ggcatatata aaaaaagact tggaattgta ccagtgcgac atataatggc tttgtaaaat    2075 attctgatta aaacggaatg tttaaggata ggaaaagaaa gtattctttt cctgtctttt    2135 ttatgtaacc ttaaaaatta cagccaatta ttcaataaaa taatttctgt aaatcagtta    2195 ttcttgaacc aatattaaaa gaatttcccc aaggtcttta atgtctggcc ggattacatt    2255 atcttctcct gtcattttaa aaaacagtta aatcaagctt ttgtcgcaat agaatgaatt    2315 attatttggg attccaaacc aaagacatat cattaagcag ttgtaaaaa               2364
```

<210> SEQ ID NO 24
<211> LENGTH: 512
<212> TYPE: PRT
<213> ORGANISM: Clostridium stercorarium

<400> SEQUENCE: 24

```
Met Lys Arg Lys Val Lys Lys Met Ala Ala Met Ala Thr Ser Ile Ile
 1               5                  10                  15

Met Ala Ile Met Ile Ile Leu His Ser Ile Pro Val Leu Ala Gly Arg
            20                  25                  30

Ile Ile Tyr Asp Asn Glu Thr Gly Thr His Gly Gly Tyr Asp Tyr Glu
        35                  40                  45

Leu Trp Lys Asp Tyr Gly Asn Thr Ile Met Glu Leu Asn Asp Gly Gly
    50                  55                  60

Thr Phe Ser Cys Gln Trp Ser Asn Ile Gly Asn Ala Leu Phe Arg Lys
65                  70                  75                  80

Gly Arg Lys Phe Asn Ser Asp Lys Thr Tyr Gln Glu Leu Gly Asp Ile
                85                  90                  95

Val Val Glu Tyr Gly Cys Asp Tyr Asn Pro Asn Gly Asn Ser Tyr Leu
            100                 105                 110

Cys Val Tyr Gly Trp Thr Arg Asn Pro Leu Val Glu Tyr Tyr Ile Val
        115                 120                 125

Glu Ser Trp Gly Ser Trp Arg Pro Pro Gly Ala Thr Pro Lys Gly Thr
    130                 135                 140

Ile Thr Gln Trp Met Ala Gly Thr Tyr Glu Ile Tyr Glu Thr Thr Arg
145                 150                 155                 160

Val Asn Gln Pro Ser Ile Asp Gly Thr Ala Thr Phe Gln Gln Tyr Trp
                165                 170                 175

Ser Val Arg Thr Ser Lys Arg Thr Ser Gly Thr Ile Ser Val Thr Glu
            180                 185                 190

His Phe Lys Gln Trp Glu Arg Met Gly Met Arg Met Gly Lys Met Tyr
        195                 200                 205

Glu Val Ala Leu Thr Val Glu Gly Tyr Gln Ser Ser Gly Tyr Ala Asn
    210                 215                 220

Val Tyr Lys Asn Glu Ile Arg Ile Gly Ala Asn Pro Thr Pro Ala Pro
225                 230                 235                 240

Ser Gln Ser Pro Ile Arg Arg Asp Ala Phe Ser Ile Glu Ala Glu
                245                 250                 255

Glu Tyr Asn Ser Thr Asn Ser Ser Thr Leu Gln Val Ile Gly Thr Pro
            260                 265                 270

Asn Asn Gly Arg Gly Ile Gly Tyr Ile Glu Asn Gly Asn Thr Val Thr
```

|     |     |     |     | 275 |     |     |     |     | 280 |     |     |     |     | 285 |     |     |
| --- | --- | --- | --- | --- | --- | --- | --- | --- | --- | --- | --- | --- | --- | --- | --- | --- |
| Tyr | Ser | Asn | Ile | Asp | Phe | Gly | Ser | Gly | Ala | Thr | Gly | Phe | Ser | Ala | Thr |
|     |     |     | 290 |     |     |     |     | 295 |     |     |     |     | 300 |     |     |

Val Ala Thr Glu Val Asn Thr Ser Ile Gln Ile Arg Ser Asp Ser Pro
305             310             315             320

Thr Gly Thr Leu Leu Gly Thr Leu Tyr Val Ser Ser Thr Gly Ser Trp
            325             330             335

Asn Thr Tyr Gln Thr Val Ser Thr Asn Ile Ser Lys Ile Thr Gly Val
            340             345             350

His Asp Ile Val Leu Val Phe Ser Gly Pro Val Asn Val Asp Asn Phe
            355             360             365

Ile Phe Ser Arg Ser Ser Pro Val Pro Ala Pro Gly Asp Asn Thr Arg
            370             375             380

Asp Ala Tyr Ser Ile Ile Gln Ala Glu Asp Tyr Asp Ser Ser Tyr Gly
385             390             395             400

Pro Asn Leu Gln Ile Phe Ser Leu Pro Gly Gly Ser Ala Ile Gly
            405             410             415

Tyr Ile Glu Asn Gly Tyr Ser Thr Thr Tyr Lys Asn Ile Asp Phe Gly
            420             425             430

Asp Gly Ala Thr Ser Val Thr Ala Arg Val Ala Thr Gln Asn Ala Thr
            435             440             445

Thr Ile Gln Val Arg Leu Gly Ser Pro Ser Gly Thr Leu Leu Gly Thr
            450             455             460

Ile Tyr Val Gly Ser Thr Gly Ser Phe Asp Thr Tyr Arg Asp Val Ser
465             470             475             480

Ala Thr Ile Ser Asn Thr Ala Gly Val Lys Asp Ile Val Leu Val Phe
            485             490             495

Ser Gly Pro Val Asn Val Asp Trp Phe Val Phe Ser Lys Ser Gly Thr
            500             505             510

```
<210> SEQ ID NO 25
<211> LENGTH: 1221
<212> TYPE: DNA
<213> ORGANISM: Orpinomyces sp. PC-2
<220> FEATURE:
<221> NAME/KEY: CDS
<222> LOCATION: (97)..(1182)

<400> SEQUENCE: 25
```

| ggcacgagga | aattttttt | actggttaaa | aaaaaattat | aaaactaaat | aaataaaaaa |       | 60  |
| --- | --- | --- | --- | --- | --- | --- | --- |
| aatatttttt | gaaatatatt | aaaataggaa | aaaaaa atg aga act att aaa ttt |  |  |  | 114 |
|  |  |  | Met Arg Thr Ile Lys Phe |  |  |  |
|  |  |  | 1 | 5 |  |  |  |

| tta ttc gca tta gct att aca acc gtt gct aag gcc caa tgg ggt gga |  | 162 |
| --- | --- | --- |
| Leu Phe Ala Leu Ala Ile Thr Thr Val Ala Lys Ala Gln Trp Gly Gly |  |  |
|  10         15         20 |  |  |

| aac ggt ggt gcc tct gct ggt caa aga tta agc gtt ggt ggt ggt caa |  | 210 |
| --- | --- | --- |
| Asn Gly Gly Ala Ser Ala Gly Gln Arg Leu Ser Val Gly Gly Gly Gln |  |  |
| 25             30             35 |  |  |

| aac caa cat aaa ggt gtt ttt gat ggc ttc agt tat gaa atc tgg tta |  | 258 |
| --- | --- | --- |
| Asn Gln His Lys Gly Val Phe Asp Gly Phe Ser Tyr Glu Ile Trp Leu |  |  |
| 40             45             50 |  |  |

| gat aac acc ggt ggt agt ggt tcc atg acc ctt ggt aaa ggt gca acc |  | 306 |
| --- | --- | --- |
| Asp Asn Thr Gly Gly Ser Gly Ser Met Thr Leu Gly Lys Gly Ala Thr |  |  |
| 55             60             65             70 |  |  |

| ttc aag gct gaa tgg agt gca gct gtt aac cgt ggt aac ttc ctt gcc |  | 354 |
| --- | --- | --- |
| Phe Lys Ala Glu Trp Ser Ala Ala Val Asn Arg Gly Asn Phe Leu Ala |  |  |

```
                       75                  80                  85
cgt cgt ggt ctt gat ttc ggt tct acc aaa aag gca acc gct tac gaa        402
Arg Arg Gly Leu Asp Phe Gly Ser Thr Lys Lys Ala Thr Ala Tyr Glu
            90                  95                 100 tac atc gga ttg gat tat gaa gca agt tac aga caa act gcc agc gca        450
Tyr Ile Gly Leu Asp Tyr Glu Ala Ser Tyr Arg Gln Thr Ala Ser Ala
           105                 110                 115 agt ggt aac tcc cgt ctt tgt gta tac ggc tgg ttc caa aac cgt gga        498
Ser Gly Asn Ser Arg Leu Cys Val Tyr Gly Trp Phe Gln Asn Arg Gly
        120                 125                 130 gtt caa ggc gta cct ttg gta gaa tac tac atc att gaa gat tgg gtt        546
Val Gln Gly Val Pro Leu Val Glu Tyr Tyr Ile Ile Glu Asp Trp Val
135                 140                 145                 150 gac tgg gta cca gat gca caa gga aaa atg gta acc atc gat ggt gca        594
Asp Trp Val Pro Asp Ala Gln Gly Lys Met Val Thr Ile Asp Gly Ala
                155                 160                 165 caa tat aag att ttc caa atg gat cac act ggt cca act atc aat ggt        642
Gln Tyr Lys Ile Phe Gln Met Asp His Thr Gly Pro Thr Ile Asn Gly
            170                 175                 180 ggt aat gaa acc ttt aag caa tac ttc agt gtc cgt caa caa aag aga        690
Gly Asn Glu Thr Phe Lys Gln Tyr Phe Ser Val Arg Gln Gln Lys Arg
        185                 190                 195 act tct ggt cat att act gta tca gat cac ttt aag gca tgg tcc aat        738
Thr Ser Gly His Ile Thr Val Ser Asp His Phe Lys Ala Trp Ser Asn
    200                 205                 210 caa ggt tgg ggt att gga aac ctc tat gaa gtt gca ttg aac gca gaa        786
Gln Gly Trp Gly Ile Gly Asn Leu Tyr Glu Val Ala Leu Asn Ala Glu
215                 220                 225                 230 ggt tgg caa agt agt ggt gtc gct gac gtc ccc aag ttg gat gtc tac        834
Gly Trp Gln Ser Ser Gly Val Ala Asp Val Pro Lys Leu Asp Val Tyr
                235                 240                 245 acc acc aaa caa ggt tct gct cct cgt act acc acc act acc cgt            882
Thr Thr Lys Gln Gly Ser Ala Pro Arg Thr Thr Thr Thr Thr Arg
            250                 255                 260 act act acc cgt act act aca aaa aca ctt cca acc act aat aaa aaa        930
Thr Thr Thr Arg Thr Thr Thr Lys Thr Leu Pro Thr Thr Asn Lys Lys
        265                 270                 275 tgt tct gcc aag att act gcc caa ggt tac aag tgt tgt agt gat cca        978
Cys Ser Ala Lys Ile Thr Ala Gln Gly Tyr Lys Cys Cys Ser Asp Pro
    280                 285                 290 aat tgt gtt gtt tac tac act gat gaa gat ggt acc tgg ggt gtt gaa       1026
Asn Cys Val Val Tyr Tyr Thr Asp Glu Asp Gly Thr Trp Gly Val Glu
295                 300                 305                 310 aac aat caa tgg tgt gga tgt ggt gtt gaa gca tgt tct ggc aag att       1074
Asn Asn Gln Trp Cys Gly Cys Gly Val Glu Ala Cys Ser Gly Lys Ile
                315                 320                 325 act gcc caa ggt tac aag tgt tgt agt gat cca aag tgt gtt gtt tac       1122
Thr Ala Gln Gly Tyr Lys Cys Cys Ser Asp Pro Lys Cys Val Val Tyr
            330                 335                 340 tac act gat gac gat ggt aaa tgg ggt gtt gaa aac aac gaa tgg tgt       1170
Tyr Thr Asp Asp Asp Gly Lys Trp Gly Val Glu Asn Asn Glu Trp Cys
        345                 350                 355 ggt tgt ggt tta taagcagaaa aatactaatt tagtaaaaaa aaaaaaaaa            1221
Gly Cys Gly Leu
    360

<210> SEQ ID NO 26
<211> LENGTH: 362
<212> TYPE: PRT
<213> ORGANISM: Orpinomyces sp. PC-2
```

-continued

```
<400> SEQUENCE: 26

Met Arg Thr Ile Lys Phe Leu Phe Ala Leu Ala Ile Thr Thr Val Ala
 1               5                  10                  15

Lys Ala Gln Trp Gly Gly Asn Gly Gly Ala Ser Ala Gly Gln Arg Leu
             20                  25                  30

Ser Val Gly Gly Gly Gln Asn Gln His Lys Gly Val Phe Asp Gly Phe
             35                  40                  45

Ser Tyr Glu Ile Trp Leu Asp Asn Thr Gly Gly Ser Gly Ser Met Thr
         50                  55                  60

Leu Gly Lys Gly Ala Thr Phe Lys Ala Glu Trp Ser Ala Ala Val Asn
 65                  70                  75                  80

Arg Gly Asn Phe Leu Ala Arg Arg Gly Leu Asp Phe Gly Ser Thr Lys
                 85                  90                  95

Lys Ala Thr Ala Tyr Glu Tyr Ile Gly Leu Asp Tyr Glu Ala Ser Tyr
                100                 105                 110

Arg Gln Thr Ala Ser Ala Ser Gly Asn Ser Arg Leu Cys Val Tyr Gly
            115                 120                 125

Trp Phe Gln Asn Arg Gly Val Gln Gly Val Pro Leu Val Glu Tyr Tyr
130                 135                 140

Ile Ile Glu Asp Trp Val Asp Trp Val Pro Asp Ala Gln Gly Lys Met
145                 150                 155                 160

Val Thr Ile Asp Gly Ala Gln Tyr Lys Ile Phe Gln Met Asp His Thr
                165                 170                 175

Gly Pro Thr Ile Asn Gly Gly Asn Glu Thr Phe Lys Gln Tyr Phe Ser
                180                 185                 190

Val Arg Gln Gln Lys Arg Thr Ser Gly His Ile Thr Val Ser Asp His
            195                 200                 205

Phe Lys Ala Trp Ser Asn Gln Gly Trp Gly Ile Gly Asn Leu Tyr Glu
        210                 215                 220

Val Ala Leu Asn Ala Glu Gly Trp Gln Ser Ser Gly Val Ala Asp Val
225                 230                 235                 240

Pro Lys Leu Asp Val Tyr Thr Thr Lys Gln Gly Ser Ala Pro Arg Thr
                245                 250                 255

Thr Thr Thr Thr Thr Arg Thr Thr Thr Arg Thr Thr Thr Lys Thr Leu
                260                 265                 270

Pro Thr Thr Asn Lys Lys Cys Ser Ala Lys Ile Thr Ala Gln Gly Tyr
            275                 280                 285

Lys Cys Cys Ser Asp Pro Asn Cys Val Val Tyr Tyr Thr Asp Glu Asp
        290                 295                 300

Gly Thr Trp Gly Val Glu Asn Asn Gln Trp Cys Gly Cys Gly Val Glu
305                 310                 315                 320

Ala Cys Ser Gly Lys Ile Thr Ala Gln Gly Tyr Lys Cys Cys Ser Asp
                325                 330                 335

Pro Lys Cys Val Val Tyr Tyr Thr Asp Asp Asp Gly Lys Trp Gly Val
            340                 345                 350

Glu Asn Asn Glu Trp Cys Gly Cys Gly Leu
            355                 360
```